(12) United States Patent
Boudreaux

(10) Patent No.: US 8,322,589 B2
(45) Date of Patent: Dec. 4, 2012

(54) SURGICAL STAPLING INSTRUMENTS

(75) Inventor: Chad P. Boudreaux, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 29 days.

(21) Appl. No.: 12/830,013

(22) Filed: Jul. 2, 2010

(65) Prior Publication Data
US 2010/0308100 A1    Dec. 9, 2010

Related U.S. Application Data

(62) Division of application No. 11/821,277, filed on Jun. 22, 2007, now Pat. No. 7,753,245.

(51) Int. Cl.
*A61B 17/068* (2006.01)
(52) U.S. Cl. .................... 227/175.4; 227/176.1
(58) Field of Classification Search ............... 227/175.1, 227/175.4, 176.1
See application file for complete search history.

(56) References Cited

U.S. PATENT DOCUMENTS

| | | | |
|---|---|---|---|
| 2,853,074 A | 9/1958 | Olson | |
| 2,959,974 A | 11/1960 | Emrick | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| RE28,932 E | 8/1976 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |

(Continued)

FOREIGN PATENT DOCUMENTS

CA    2458946 A1    3/2003

(Continued)

OTHER PUBLICATIONS

Partial European Search Report, Application 11163523.1. dated Aug. 4, 2011 (2 pages).

(Continued)

*Primary Examiner* — Sameh H. Tawfik
*Assistant Examiner* — Michelle Lopez

(57) ABSTRACT

A surgical instrument including a shaft, an end effector movable relative to the shaft, a locking mechanism configured to engage the shaft and/or end effector to fix the relative relationship between the shaft and end effector, and a closure system configured to close the end effector and engage the locking mechanism to prevent it from becoming unlocked. The instrument can further include a firing drive comprising a trigger, a firing member, and a pawl, where the pawl is rotatable between a first position in which the pawl is disengaged from the firing member and a second position in which the trigger can advance the pawl and firing member toward the end effector. The instrument can also include a reel, a band, where the band can be wound around the reel to retract the firing member, and a return mechanism for selectively engaging the trigger with the firing member and the reel.

20 Claims, 63 Drawing Sheets

U.S. PATENT DOCUMENTS

| | | |
|---|---|---|
| 4,506,671 A | 3/1985 | Green |
| 4,522,327 A | 6/1985 | Korthoff et al. |
| 4,530,453 A | 7/1985 | Green |
| 4,565,109 A | 1/1986 | Tsay |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,941,623 A | 7/1990 | Pruitt |
| 4,944,443 A | 7/1990 | Oddsen et al. |
| 4,973,274 A | 11/1990 | Hirukawa |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,209,747 A | 5/1993 | Knoepfler |
| 5,211,649 A | 5/1993 | Kohler et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,271,543 A | 12/1993 | Grant et al. |
| 5,282,806 A | 2/1994 | Haber et al. |
| 5,282,829 A | 2/1994 | Hermes |
| 5,304,204 A | 4/1994 | Bregen |
| 5,307,976 A | 5/1994 | Olson et al. |
| 5,312,024 A | 5/1994 | Grant et al. |
| 5,318,221 A | 6/1994 | Green et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,383,888 A | 1/1995 | Zvenyatsky et al. |
| 5,397,324 A | 3/1995 | Carroll et al. |
| 5,405,072 A | 4/1995 | Zlock et al. |
| 5,413,268 A | 5/1995 | Green et al. |
| 5,413,272 A | 5/1995 | Green et al. |
| 5,417,203 A | 5/1995 | Tovey et al. |
| 5,417,361 A | 5/1995 | Williamson, IV |
| 5,425,745 A | 6/1995 | Green et al. |
| 5,431,654 A | 7/1995 | Nic |
| 5,437,681 A | 8/1995 | Meade et al. |
| 5,456,401 A | 10/1995 | Green et al. |
| 5,465,894 A | 11/1995 | Clark et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,514,157 A | 5/1996 | Nicholas et al. |
| 5,520,700 A | 5/1996 | Beyar et al. |
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,609,601 A | 3/1997 | Kolesa et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |

| | | | | | | |
|---|---|---|---|---|---|---|
| 5,709,334 | A | 1/1998 | Sorrentino et al. | 6,250,532 B1 | 6/2001 | Green et al. |
| 5,711,472 | A | 1/1998 | Bryan | 6,264,086 B1 | 7/2001 | McGuckin, Jr. |
| 5,713,505 | A | 2/1998 | Huitema | 6,264,087 B1 | 7/2001 | Whitman |
| 5,715,987 | A | 2/1998 | Kelley et al. | 6,273,897 B1 | 8/2001 | Dalessandro et al. |
| 5,715,988 | A | 2/1998 | Palmer | 6,302,311 B1 | 10/2001 | Adams et al. |
| 5,716,366 | A | 2/1998 | Yates | 6,315,184 B1 | 11/2001 | Whitman |
| 5,718,359 | A | 2/1998 | Palmer et al. | 6,330,965 B1 | 12/2001 | Milliman et al. |
| 5,718,360 | A | 2/1998 | Green et al. | 6,370,981 B2 | 4/2002 | Watarai |
| 5,725,536 | A | 3/1998 | Oberlin et al. | 6,387,113 B1 | 5/2002 | Hawkins et al. |
| 5,725,554 | A | 3/1998 | Simon et al. | RE37,814 E | 8/2002 | Allgeyer |
| 5,730,758 | A | 3/1998 | Allgeyer | 6,436,107 B1 | 8/2002 | Wang et al. |
| 5,732,821 | A | 3/1998 | Stone et al. | 6,439,439 B1 | 8/2002 | Rickard et al. |
| 5,732,871 | A | 3/1998 | Clark et al. | 6,439,446 B1 | 8/2002 | Perry et al. |
| 5,732,872 | A | 3/1998 | Bolduc et al. | 6,443,973 B1 | 9/2002 | Whitman |
| 5,735,445 | A | 4/1998 | Vidal et al. | 6,488,196 B1 | 12/2002 | Fenton, Jr. |
| 5,743,456 | A | 4/1998 | Jones et al. | 6,488,197 B1 | 12/2002 | Whitman |
| 5,752,644 | A | 5/1998 | Bolanos et al. | 6,491,201 B1 | 12/2002 | Whitman |
| 5,758,814 | A | 6/1998 | Gallagher et al. | 6,505,768 B2 | 1/2003 | Whitman |
| 5,762,255 | A | 6/1998 | Chrisman et al. | 6,517,565 B1 | 2/2003 | Whitman et al. |
| 5,762,256 | A | 6/1998 | Mastri et al. | 6,569,171 B2 | 5/2003 | DeGuillebon et al. |
| 5,779,130 | A | 7/1998 | Alesi et al. | 6,578,751 B2 | 6/2003 | Hartwick |
| 5,779,131 | A | 7/1998 | Knodel et al. | 6,588,643 B2 | 7/2003 | Bolduc et al. |
| 5,779,132 | A | 7/1998 | Knodel et al. | 6,601,749 B2 | 8/2003 | Sullivan et al. |
| 5,782,396 | A | 7/1998 | Mastri et al. | 6,616,686 B2 | 9/2003 | Coleman et al. |
| 5,782,397 | A | 7/1998 | Koukline | 6,619,529 B2 | 9/2003 | Green et al. |
| 5,785,232 | A | 7/1998 | Vidal et al. | 6,629,630 B2 | 10/2003 | Adams |
| 5,794,834 | A | 8/1998 | Hamblin et al. | 6,629,988 B2 | 10/2003 | Weadock |
| 5,797,536 | A | 8/1998 | Smith et al. | 6,644,532 B2 | 11/2003 | Green et al. |
| 5,797,537 | A | 8/1998 | Oberlin et al. | 6,669,073 B2 | 12/2003 | Milliman et al. |
| 5,797,538 | A | 8/1998 | Heaton et al. | 6,681,978 B2 | 1/2004 | Geiste et al. |
| 5,799,857 | A | 9/1998 | Robertson et al. | 6,681,979 B2 | 1/2004 | Whitman |
| 5,820,009 | A | 10/1998 | Melling et al. | 6,695,199 B2 | 2/2004 | Whitman |
| 5,826,776 | A | 10/1998 | Schulze et al. | 6,698,643 B2 | 3/2004 | Whitman |
| 5,829,662 | A | 11/1998 | Allen et al. | 6,716,233 B1 | 4/2004 | Whitman |
| 5,833,695 | A | 11/1998 | Yoon | 6,755,338 B2 | 6/2004 | Hahnen et al. |
| 5,836,503 | A | 11/1998 | Ehrenfels et al. | 6,769,594 B2 | 8/2004 | Orban, III |
| 5,836,960 | A | 11/1998 | Kolesa et al. | 6,773,438 B1 | 8/2004 | Knodel et al. |
| 5,839,639 | A | 11/1998 | Sauer et al. | 6,786,382 B1 | 9/2004 | Hoffman |
| 5,855,311 | A | 1/1999 | Hamblin et al. | 6,805,273 B2 | 10/2004 | Bilotti et al. |
| 5,865,361 | A | 2/1999 | Milliman et al. | 6,817,508 B1 | 11/2004 | Racenet et al. |
| 5,868,760 | A | 2/1999 | McGuckin, Jr. | 6,817,509 B2 | 11/2004 | Geiste et al. |
| 5,871,135 | A | 2/1999 | Williamson, IV et al. | 6,817,974 B2 | 11/2004 | Cooper et al. |
| 5,878,937 | A | 3/1999 | Green et al. | 6,830,174 B2 | 12/2004 | Hillstead et al. |
| 5,878,938 | A | 3/1999 | Bittner et al. | 6,843,403 B2 | 1/2005 | Whitman |
| 5,893,506 | A | 4/1999 | Powell | RE38,708 E | 3/2005 | Bolanos et al. |
| 5,894,979 | A | 4/1999 | Powell | 6,866,178 B2 | 3/2005 | Adams et al. |
| 5,897,562 | A | 4/1999 | Bolanos et al. | 6,874,669 B2 | 4/2005 | Adams et al. |
| 5,901,895 | A | 5/1999 | Heaton et al. | 6,877,647 B2 | 4/2005 | Green |
| 5,904,693 | A | 5/1999 | Dicesare et al. | 6,905,057 B2 | 6/2005 | Swayze et al. |
| 5,908,427 | A | 6/1999 | McKean et al. | 6,945,444 B2 | 9/2005 | Gresham et al. |
| 5,911,353 | A | 6/1999 | Bolanos et al. | 6,953,138 B1 | 10/2005 | Dworak et al. |
| 5,915,616 | A | 6/1999 | Viola et al. | 6,953,139 B2 | 10/2005 | Milliman et al. |
| 5,918,791 | A | 7/1999 | Sorrentino et al. | 6,959,851 B2 | 11/2005 | Heinrich |
| 5,919,198 | A | 7/1999 | Graves, Jr. et al. | 6,959,852 B2 | 11/2005 | Shelton, IV et al. |
| 5,937,951 | A | 8/1999 | Izuchukwu et al. | 6,960,107 B1 | 11/2005 | Schaub et al. |
| 5,941,442 | A | 8/1999 | Geiste et al. | 6,964,363 B2 | 11/2005 | Wales et al. |
| 5,954,259 | A | 9/1999 | Viola et al. | 6,978,921 B2 | 12/2005 | Shelton, IV et al. |
| 5,988,479 | A | 11/1999 | Palmer | 6,978,922 B2 | 12/2005 | Bilotti et al. |
| 6,010,054 | A | 1/2000 | Johnson et al. | 6,981,628 B2 | 1/2006 | Wales |
| 6,032,849 | A | 3/2000 | Mastri et al. | 6,986,451 B1 | 1/2006 | Mastri et al. |
| 6,045,560 | A | 4/2000 | McKean et al. | 6,988,649 B2 | 1/2006 | Shelton, IV et al. |
| 6,047,861 | A | 4/2000 | Vidal et al. | 6,988,650 B2 | 1/2006 | Schwemberger et al. |
| 6,050,472 | A | 4/2000 | Shibata | 6,997,931 B2 | 2/2006 | Sauer et al. |
| 6,053,390 | A | 4/2000 | Green et al. | 7,000,818 B2 | 2/2006 | Shelton, IV et al. |
| 6,062,360 | A | 5/2000 | Shields | 7,000,819 B2 | 2/2006 | Swayze et al. |
| 6,079,606 | A | 6/2000 | Milliman et al. | 7,008,435 B2 | 3/2006 | Cummins |
| 6,083,242 | A | 7/2000 | Cook | 7,032,798 B2 | 4/2006 | Whitman et al. |
| 6,086,600 | A | 7/2000 | Kortenbach | 7,032,799 B2 | 4/2006 | Viola et al. |
| 6,099,551 | A | 8/2000 | Gabbay | 7,044,352 B2 | 5/2006 | Shelton, IV et al. |
| 6,102,271 | A | 8/2000 | Longo et al. | 7,044,353 B2 | 5/2006 | Mastri et al. |
| 6,109,500 | A | 8/2000 | Alli et al. | 7,055,730 B2 | 6/2006 | Ehrenfels et al. |
| 6,119,913 | A | 9/2000 | Adams et al. | 7,055,731 B2 | 6/2006 | Shelton, IV et al. |
| 6,126,058 | A | 10/2000 | Adams et al. | 7,056,330 B2 | 6/2006 | Gayton |
| 6,131,789 | A | 10/2000 | Schulze et al. | 7,059,508 B2 | 6/2006 | Shelton, IV et al. |
| 6,155,473 | A | 12/2000 | Tompkins et al. | 7,070,083 B2 | 7/2006 | Jankowski |
| 6,171,330 | B1 | 1/2001 | Benchetrit | 7,077,856 B2 | 7/2006 | Whitman |
| 6,193,129 | B1 | 2/2001 | Bittner et al. | 7,080,769 B2 | 7/2006 | Vresh et al. |
| 6,202,914 | B1 | 3/2001 | Geiste et al. | 7,083,075 B2 | 8/2006 | Swayze et al. |
| 6,241,139 | B1 | 6/2001 | Milliman et al. | 7,090,684 B2 | 8/2006 | McGuckin, Jr. et al. |

| Patent | Date | Inventor |
|---|---|---|
| 7,097,089 B2 | 8/2006 | Marczyk |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,343,920 B2 | 3/2008 | Toby et al. |
| 7,354,447 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,559,450 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,631,793 B2 | 12/2009 | Rethy et al. |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,780,055 B2 | 8/2010 | Scirica et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,845,534 B2 | 12/2010 | Viola et al. |
| 7,845,537 B2 | 12/2010 | Shelton, IV et al. |

| | | |
|---|---|---|
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,909,221 B2 | 3/2011 | Viola et al. |
| 7,922,063 B2 | 4/2011 | Zemlok et al. |
| 7,942,303 B2 | 5/2011 | Shah |
| 7,950,560 B2 | 5/2011 | Zemlok et al. |
| 7,959,050 B2 | 6/2011 | Smith et al. |
| 7,967,180 B2 | 6/2011 | Scirica |
| 8,002,795 B2 | 8/2011 | Beetel |
| D650,074 S | 12/2011 | Hunt et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0145675 A1 | 7/2005 | Hartwick et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0167471 A1 | 7/2006 | Phillips |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0034668 A1 | 2/2007 | Holsten et al. |
| 2007/0073341 A1 | 3/2007 | Smith |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0288044 A1 | 12/2007 | Jinno et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0183193 A1 | 7/2008 | Omori et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |

| | | | | | | |
|---|---|---|---|---|---|---|
| 2009/0255976 A1 | 10/2009 | Marczyk et al. | | 2011/0132965 A1 | 6/2011 | Moore et al. |
| 2009/0255977 A1 | 10/2009 | Zemlok | | 2011/0139852 A1 | 6/2011 | Zingman |
| 2009/0255978 A1 | 10/2009 | Viola et al. | | 2011/0144430 A1 | 6/2011 | Spivey et al. |
| 2009/0289096 A1 | 11/2009 | Shelton, IV et al. | | 2011/0147433 A1 | 6/2011 | Shelton, IV et al. |
| 2009/0308907 A1 | 12/2009 | Nalagatla et al. | | 2011/0147434 A1 | 6/2011 | Hueil et al. |
| 2010/0001036 A1 | 1/2010 | Marczyk et al. | | 2011/0155780 A1 | 6/2011 | Boudreaux |
| 2010/0012704 A1 | 1/2010 | Tarinelli Racenet et al. | | 2011/0155781 A1 | 6/2011 | Swensgard et al. |
| 2010/0032470 A1 | 2/2010 | Hess et al. | | 2011/0155785 A1 | 6/2011 | Laurent et al. |
| 2010/0065605 A1 | 3/2010 | Shelton, IV et al. | | 2011/0155787 A1 | 6/2011 | Baxter, III et al. |
| 2010/0069942 A1 | 3/2010 | Shelton, IV | | 2011/0163147 A1 | 7/2011 | Laurent et al. |
| 2010/0072252 A1 | 3/2010 | Baxter, III et al. | | 2011/0174860 A1 | 7/2011 | Shelton, IV et al. |
| 2010/0072254 A1 | 3/2010 | Aranyi et al. | | 2011/0174863 A1 | 7/2011 | Shelton, IV et al. |
| 2010/0072256 A1 | 3/2010 | Baxter, III et al. | | 2011/0192882 A1 | 8/2011 | Hess et al. |
| 2010/0076474 A1 | 3/2010 | Yates et al. | | 2011/0226837 A1 | 9/2011 | Baxter, III et al. |
| 2010/0076475 A1 | 3/2010 | Yates et al. | | 2011/0233258 A1 | 9/2011 | Boudreaux |
| 2010/0089970 A1 | 4/2010 | Smith et al. | | 2011/0253766 A1 | 10/2011 | Baxter, III et al. |
| 2010/0089972 A1 | 4/2010 | Marczyk | | 2011/0275901 A1 | 11/2011 | Shelton, IV |
| 2010/0089974 A1 | 4/2010 | Shelton, IV | | 2011/0276083 A1 | 11/2011 | Shelton, IV et al. |
| 2010/0096435 A1 | 4/2010 | Fuchs et al. | | 2011/0288573 A1 | 11/2011 | Yates et al. |
| 2010/0108741 A1 | 5/2010 | Hessler et al. | | 2011/0290851 A1 | 12/2011 | Shelton, IV |
| 2010/0127042 A1 | 5/2010 | Shelton, IV | | 2011/0290853 A1 | 12/2011 | Shelton, IV et al. |
| 2010/0133317 A1 | 6/2010 | Shelton, IV et al. | | 2011/0290854 A1 | 12/2011 | Timm et al. |
| 2010/0133318 A1 | 6/2010 | Boudreaux | | 2011/0290855 A1 | 12/2011 | Moore et al. |
| 2010/0163598 A1 | 7/2010 | Belzer | | 2011/0290856 A1 | 12/2011 | Shelton, IV et al. |
| 2010/0179382 A1 | 7/2010 | Shelton, IV et al. | | 2011/0290857 A1 | 12/2011 | Shelton, IV et al. |
| 2010/0181364 A1 | 7/2010 | Shelton, IV et al. | | 2011/0295242 A1 | 12/2011 | Spivey et al. |
| 2010/0193566 A1 | 8/2010 | Scheib et al. | | 2011/0295269 A1 | 12/2011 | Swensgard et al. |
| 2010/0193567 A1 | 8/2010 | Scheib et al. | | 2011/0295270 A1 | 12/2011 | Giordano et al. |
| 2010/0193568 A1 | 8/2010 | Scheib et al. | | 2011/0295295 A1 | 12/2011 | Shelton, IV et al. |
| 2010/0193569 A1 | 8/2010 | Yates et al. | | 2012/0024934 A1 | 2/2012 | Shelton, IV et al. |
| 2010/0198220 A1 | 8/2010 | Boudreaux et al. | | 2012/0024935 A1 | 2/2012 | Shelton, IV et al. |
| 2010/0200637 A1 | 8/2010 | Beetel | | 2012/0024936 A1 | 2/2012 | Baxter, III et al. |
| 2010/0213241 A1 | 8/2010 | Bedi et al. | | 2012/0029272 A1 | 2/2012 | Shelton, IV et al. |
| 2010/0222901 A1 | 9/2010 | Swayze et al. | | 2012/0029544 A1 | 2/2012 | Shelton, IV et al. |
| 2010/0224669 A1 | 9/2010 | Shelton, IV et al. | | 2012/0029547 A1 | 2/2012 | Shelton, IV et al. |
| 2010/0237132 A1 | 9/2010 | Measamer et al. | | 2012/0061448 A1 | 3/2012 | Zingman |
| 2010/0243707 A1 | 9/2010 | Olson et al. | | 2012/0071711 A1 | 3/2012 | Shelton, IV et al. |
| 2010/0243708 A1 | 9/2010 | Aranyi et al. | | 2012/0071866 A1 | 3/2012 | Kerr et al. |
| 2010/0243709 A1 | 9/2010 | Hess et al. | | 2012/0074196 A1 | 3/2012 | Shelton, IV et al. |
| 2010/0264193 A1 | 10/2010 | Huang et al. | | 2012/0074198 A1 | 3/2012 | Huitema et al. |
| 2010/0264194 A1 | 10/2010 | Huang et al. | | 2012/0074200 A1 | 3/2012 | Schmid et al. |
| 2010/0276471 A1 | 11/2010 | Whitman | | 2012/0074201 A1 | 3/2012 | Baxter, III et al. |
| 2010/0294827 A1 | 11/2010 | Boyden et al. | | 2012/0080332 A1 | 4/2012 | Shelton, IV et al. |
| 2010/0294829 A1 | 11/2010 | Giordano et al. | | 2012/0080333 A1 | 4/2012 | Woodard, Jr. et al. |
| 2010/0301095 A1 | 12/2010 | Shelton, IV et al. | | 2012/0080334 A1 | 4/2012 | Shelton, IV et al. |
| 2010/0301096 A1 | 12/2010 | Moore et al. | | 2012/0080335 A1 | 4/2012 | Shelton, IV et al. |
| 2010/0305552 A1 | 12/2010 | Shelton, IV et al. | | 2012/0080336 A1 | 4/2012 | Shelton, IV et al. |
| 2011/0006099 A1 | 1/2011 | Hall et al. | | 2012/0080337 A1 | 4/2012 | Shelton, IV et al. |
| 2011/0006101 A1 | 1/2011 | Hall et al. | | 2012/0080338 A1 | 4/2012 | Shelton, IV et al. |
| 2011/0006103 A1 | 1/2011 | Laurent et al. | | 2012/0080339 A1 | 4/2012 | Shelton, IV et al. |
| 2011/0011914 A1 | 1/2011 | Baxter, III et al. | | 2012/0080340 A1 | 4/2012 | Shelton, IV et al. |
| 2011/0011915 A1 | 1/2011 | Shelton, IV | | 2012/0080344 A1 | 4/2012 | Shelton, IV |
| 2011/0017801 A1 | 1/2011 | Zemlok et al. | | 2012/0080345 A1 | 4/2012 | Morgan et al. |
| 2011/0024477 A1 | 2/2011 | Hall et al. | | 2012/0080477 A1 | 4/2012 | Leimbach et al. |
| 2011/0024478 A1 | 2/2011 | Shelton, IV | | 2012/0080478 A1 | 4/2012 | Morgan et al. |
| 2011/0024479 A1 | 2/2011 | Swensgard et al. | | 2012/0080479 A1 | 4/2012 | Shelton, IV |
| 2011/0036887 A1 | 2/2011 | Zemlok et al. | | 2012/0080480 A1 | 4/2012 | Woodard, Jr. et al. |
| 2011/0042441 A1 | 2/2011 | Shelton, IV et al. | | 2012/0080481 A1 | 4/2012 | Widenhouse et al. |
| 2011/0060363 A1 | 3/2011 | Hess et al. | | 2012/0080482 A1 | 4/2012 | Schall et al. |
| 2011/0062212 A1 | 3/2011 | Shelton, IV et al. | | 2012/0080483 A1 | 4/2012 | Riestenberg et al. |
| 2011/0068145 A1 | 3/2011 | Bedi et al. | | 2012/0080484 A1 | 4/2012 | Morgan et al. |
| 2011/0068148 A1 | 3/2011 | Hall et al. | | 2012/0080485 A1 | 4/2012 | Woodard, Jr. et al. |
| 2011/0084112 A1 | 4/2011 | Kostrzewski | | 2012/0080486 A1 | 4/2012 | Woodard, Jr. et al. |
| 2011/0084113 A1 | 4/2011 | Bedi et al. | | 2012/0080487 A1 | 4/2012 | Woodard, Jr. et al. |
| 2011/0084115 A1 | 4/2011 | Bedi et al. | | 2012/0080488 A1 | 4/2012 | Shelton, IV et al. |
| 2011/0087276 A1 | 4/2011 | Bedi et al. | | 2012/0080489 A1 | 4/2012 | Shelton, IV et al. |
| 2011/0101065 A1 | 5/2011 | Milliman | | 2012/0080490 A1 | 4/2012 | Shelton, IV et al. |
| 2011/0114697 A1 | 5/2011 | Baxter, III et al. | | 2012/0080491 A1 | 4/2012 | Shelton, IV et al. |
| 2011/0114698 A1 | 5/2011 | Baxter, III et al. | | 2012/0080493 A1 | 4/2012 | Shelton, IV et al. |
| 2011/0114699 A1 | 5/2011 | Baxter, III et al. | | 2012/0080496 A1 | 4/2012 | Schall et al. |
| 2011/0114700 A1 | 5/2011 | Baxter, III et al. | | 2012/0080498 A1 | 4/2012 | Shelton, IV et al. |
| 2011/0118761 A1 | 5/2011 | Baxter, III et al. | | 2012/0080499 A1 | 4/2012 | Schall et al. |
| 2011/0121051 A1 | 5/2011 | Shelton, IV et al. | | 2012/0080500 A1 | 4/2012 | Morgan et al. |
| 2011/0121052 A1 | 5/2011 | Shelton, IV et al. | | 2012/0080501 A1 | 4/2012 | Morgan et al. |
| 2011/0125176 A1 | 5/2011 | Yates et al. | | 2012/0080502 A1 | 4/2012 | Morgan et al. |
| 2011/0125177 A1 | 5/2011 | Yates et al. | | 2012/0080503 A1 | 4/2012 | Woodard, Jr. et al. |
| 2011/0132962 A1 | 6/2011 | Hall et al. | | 2012/0083833 A1 | 4/2012 | Shelton, IV et al. |
| 2011/0132963 A1 | 6/2011 | Giordano et al. | | 2012/0083834 A1 | 4/2012 | Shelton, IV et al. |
| 2011/0132964 A1 | 6/2011 | Weisenburgh, II et al. | | | | |

| | | | |
|---|---|---|---|
| 2012/0083835 A1 | 4/2012 | Shelton, IV et al. | |
| 2012/0083836 A1 | 4/2012 | Shelton, IV et al. | |
| 2012/0132450 A1 | 5/2012 | Timm et al. | |

FOREIGN PATENT DOCUMENTS

| | | | |
|---|---|---|---|
| CA | 2512960 A1 | 1/2006 | |
| CA | 2514274 A1 | 1/2006 | |
| CN | 1868411 A | 11/2006 | |
| CN | 1915180 A | 2/2007 | |
| CN | 101095621 A | 1/2008 | |
| DE | 273689 C | 5/1914 | |
| DE | 1775926 A | 1/1972 | |
| DE | 3036217 A1 | 4/1982 | |
| DE | 3210466 A1 | 9/1983 | |
| DE | 9412228 U | 9/1994 | |
| DE | 19509116 A1 | 9/1996 | |
| DE | 19851291 A1 | 1/2000 | |
| DE | 19924311 A1 | 11/2000 | |
| DE | 69328576 T2 | 1/2001 | |
| DE | 10052679 A1 | 5/2001 | |
| DE | 20112837 U1 | 10/2001 | |
| DE | 20121753 U1 | 4/2003 | |
| DE | 10314072 A1 | 10/2004 | |
| DE | 202007003114 U1 | 6/2007 | |
| EP | 0122046 A1 | 10/1984 | |
| EP | 0070230 B1 | 10/1985 | |
| EP | 0387980 B1 | 10/1985 | |
| EP | 0033548 B1 | 5/1986 | |
| EP | 0276104 A2 | 7/1988 | |
| EP | 0248844 B1 | 1/1993 | |
| EP | 0545029 A1 | 6/1993 | |
| EP | 0277959 B1 | 10/1993 | |
| EP | 0233940 B1 | 11/1993 | |
| EP | 0261230 B1 | 11/1993 | |
| EP | 0639349 A2 | 2/1994 | |
| EP | 0324636 B1 | 3/1994 | |
| EP | 0593920 A1 | 4/1994 | |
| EP | 0427949 B1 | 6/1994 | |
| EP | 0523174 B1 | 6/1994 | |
| EP | 0600182 A2 | 6/1994 | |
| EP | 0310431 B1 | 11/1994 | |
| EP | 0375302 B1 | 11/1994 | |
| EP | 0376562 B1 | 11/1994 | |
| EP | 0630612 A1 | 12/1994 | |
| EP | 0634144 A1 | 1/1995 | |
| EP | 0646356 A2 | 4/1995 | |
| EP | 0646357 A1 | 4/1995 | |
| EP | 0653189 A2 | 5/1995 | |
| EP | 0669104 A1 | 8/1995 | |
| EP | 0511470 B1 | 10/1995 | |
| EP | 0679367 A2 | 11/1995 | |
| EP | 0392547 B1 | 12/1995 | |
| EP | 0685204 A1 | 12/1995 | |
| EP | 0364216 B1 | 1/1996 | |
| EP | 0699418 A1 | 3/1996 | |
| EP | 0702937 A1 | 3/1996 | |
| EP | 0705571 A1 | 4/1996 | |
| EP | 0711611 A2 | 5/1996 | |
| EP | 0484677 B2 | 6/1996 | |
| EP | 0541987 B1 | 7/1996 | |
| EP | 0667119 B1 | 7/1996 | |
| EP | 0708618 B1 | 3/1997 | |
| EP | 0770355 A1 | 5/1997 | |
| EP | 0503662 B1 | 6/1997 | |
| EP | 0447121 B1 | 7/1997 | |
| EP | 0625077 B1 | 7/1997 | |
| EP | 0633749 B1 | 8/1997 | |
| EP | 0710090 B1 | 8/1997 | |
| EP | 0578425 B1 | 9/1997 | |
| EP | 0625335 B1 | 11/1997 | |
| EP | 0552423 B1 | 1/1998 | |
| EP | 0592244 B1 | 1/1998 | |
| EP | 0648476 B1 | 1/1998 | |
| EP | 0649290 B1 | 3/1998 | |
| EP | 0598618 B1 | 9/1998 | |
| EP | 0676173 B1 | 9/1998 | |
| EP | 0678007 B1 | 9/1998 | |
| EP | 0603472 B1 | 11/1998 | |
| EP | 0605351 B1 | 11/1998 | |
| EP | 0878169 A1 | 11/1998 | |
| EP | 0879742 A1 | 11/1998 | |
| EP | 0695144 B1 | 12/1998 | |
| EP | 0722296 B1 | 12/1998 | |
| EP | 0760230 B1 | 2/1999 | |
| EP | 0623316 B1 | 3/1999 | |
| EP | 0650701 B1 | 3/1999 | |
| EP | 0537572 B1 | 6/1999 | |
| EP | 0923907 A1 | 6/1999 | |
| EP | 0843906 B1 | 3/2000 | |
| EP | 0552050 B1 | 5/2000 | |
| EP | 0833592 B1 | 5/2000 | |
| EP | 0830094 B1 | 9/2000 | |
| EP | 1034747 A1 | 9/2000 | |
| EP | 1034748 A1 | 9/2000 | |
| EP | 0694290 B1 | 11/2000 | |
| EP | 1050278 A1 | 11/2000 | |
| EP | 1053719 A1 | 11/2000 | |
| EP | 1053720 A1 | 11/2000 | |
| EP | 1055399 A1 | 11/2000 | |
| EP | 1055400 A1 | 11/2000 | |
| EP | 1080694 A1 | 3/2001 | |
| EP | 1090592 A1 | 4/2001 | |
| EP | 1095627 A1 | 5/2001 | |
| EP | 1256318 A1 | 5/2001 | |
| EP | 0806914 B1 | 9/2001 | |
| EP | 0768840 B1 | 12/2001 | |
| EP | 0908152 B1 | 1/2002 | |
| EP | 0872213 B1 | 5/2002 | |
| EP | 0862386 B1 | 6/2002 | |
| EP | 0949886 B1 | 9/2002 | |
| EP | 1238634 A2 | 9/2002 | |
| EP | 0858295 B1 | 12/2002 | |
| EP | 0656188 B1 | 1/2003 | |
| EP | 1284120 A1 | 2/2003 | |
| EP | 1287788 A1 | 3/2003 | |
| EP | 0717966 B1 | 4/2003 | |
| EP | 0869742 B1 | 5/2003 | |
| EP | 0829235 B1 | 6/2003 | |
| EP | 0887046 B1 | 7/2003 | |
| EP | 0852480 B1 | 8/2003 | |
| EP | 0891154 B1 | 9/2003 | |
| EP | 0813843 B1 | 10/2003 | |
| EP | 0873089 B1 | 10/2003 | |
| EP | 0856326 B1 | 11/2003 | |
| EP | 1374788 A1 | 1/2004 | |
| EP | 0741996 B1 | 2/2004 | |
| EP | 0814712 B1 | 2/2004 | |
| EP | 1402837 A1 | 3/2004 | |
| EP | 0705570 B1 | 4/2004 | |
| EP | 0959784 B1 | 4/2004 | |
| EP | 1407719 A2 | 4/2004 | |
| EP | 1086713 B1 | 5/2004 | |
| EP | 0996378 B1 | 6/2004 | |
| EP | 1426012 A1 | 6/2004 | |
| EP | 0833593 B2 | 7/2004 | |
| EP | 1442694 A1 | 8/2004 | |
| EP | 0888749 B1 | 9/2004 | |
| EP | 0959786 B1 | 9/2004 | |
| EP | 1459695 A1 | 9/2004 | |
| EP | 1473819 A1 | 11/2004 | |
| EP | 1477119 A1 | 11/2004 | |
| EP | 1479345 A1 | 11/2004 | |
| EP | 1479347 A1 | 11/2004 | |
| EP | 1479348 A1 | 11/2004 | |
| EP | 0754437 B2 | 12/2004 | |
| EP | 1025807 B1 | 12/2004 | |
| EP | 1001710 B1 | 1/2005 | |
| EP | 1520521 A1 | 4/2005 | |
| EP | 1520523 A1 | 4/2005 | |
| EP | 1520525 A1 | 4/2005 | |
| EP | 1522264 A1 | 4/2005 | |
| EP | 1523942 A2 | 4/2005 | |
| EP | 1550408 A1 | 7/2005 | |
| EP | 1557129 A1 | 7/2005 | |
| EP | 1064883 B1 | 8/2005 | |
| EP | 1067876 B1 | 8/2005 | |
| EP | 0870473 B1 | 9/2005 | |
| EP | 1157666 B1 | 9/2005 | |

| | | | | | | |
|---|---|---|---|---|---|---|
| EP | 0880338 | B1 | 10/2005 | EP | 1702570 B1 | 10/2010 |
| EP | 1158917 | B1 | 11/2005 | EP | 1785098 B1 | 10/2010 |
| EP | 1344498 | B1 | 11/2005 | EP | 1627605 B1 | 12/2010 |
| EP | 1330989 | B1 | 12/2005 | EP | 1813205 B1 | 6/2011 |
| EP | 0771176 | B2 | 1/2006 | EP | 1785102 B1 | 1/2012 |
| EP | 1621138 | A2 | 2/2006 | FR | 999646 A | 2/1952 |
| EP | 1621139 | A2 | 2/2006 | FR | 1112936 A | 3/1956 |
| EP | 1621141 | A2 | 2/2006 | FR | 2765794 A | 1/1999 |
| EP | 1621145 | A2 | 2/2006 | GB | 939929 A | 10/1963 |
| EP | 1621151 | A2 | 2/2006 | GB | 1210522 A | 10/1970 |
| EP | 1034746 | B1 | 3/2006 | GB | 1217159 A | 12/1970 |
| EP | 1632191 | A2 | 3/2006 | GB | 1339394 A | 12/1973 |
| EP | 1065981 | B1 | 5/2006 | GB | 2109241 A | 6/1983 |
| EP | 1082944 | B1 | 5/2006 | GB | 2272159 A | 5/1994 |
| EP | 1652481 | A2 | 5/2006 | GB | 2284242 A | 5/1995 |
| EP | 1382303 | B1 | 6/2006 | GB | 2336214 A | 10/1999 |
| EP | 1253866 | B1 | 7/2006 | GB | 2425903 A | 11/2006 |
| EP | 1943976 | A2 | 7/2006 | JP | 6007357 A | 1/1994 |
| EP | 1032318 | B1 | 8/2006 | JP | 7051273 A | 2/1995 |
| EP | 1045672 | B1 | 8/2006 | JP | 8033641 A | 2/1996 |
| EP | 1617768 | B1 | 8/2006 | JP | 8229050 A | 9/1996 |
| EP | 1693015 | A2 | 8/2006 | JP | 2000033071 A | 2/2000 |
| EP | 1400214 | B1 | 9/2006 | JP | 2000171730 A | 6/2000 |
| EP | 1702567 | A2 | 9/2006 | JP | 2000287987 A | 10/2000 |
| EP | 1129665 | B1 | 11/2006 | JP | 2000325303 A | 11/2000 |
| EP | 1400206 | B1 | 11/2006 | JP | 2001286477 A | 10/2001 |
| EP | 1721568 | A1 | 11/2006 | JP | 2002143078 A | 5/2002 |
| EP | 1256317 | B1 | 12/2006 | JP | 2002369820 A | 12/2002 |
| EP | 1728473 | A1 | 12/2006 | JP | 2005-028149 A | 2/2005 |
| EP | 1728475 | A2 | 12/2006 | JP | 2005505322 T | 2/2005 |
| EP | 1479346 | B1 | 1/2007 | JP | 2005103293 A | 4/2005 |
| EP | 1484024 | B1 | 1/2007 | JP | 2005131163 A | 5/2005 |
| EP | 1754445 | A2 | 2/2007 | JP | 2005131164 A | 5/2005 |
| EP | 1759812 | A1 | 3/2007 | JP | 2005131173 A | 5/2005 |
| EP | 1767163 | A1 | 3/2007 | JP | 2005131211 A | 5/2005 |
| EP | 1769756 | A1 | 4/2007 | JP | 2005131212 A | 5/2005 |
| EP | 1769758 | A1 | 4/2007 | JP | 2005137423 A | 6/2005 |
| EP | 1581128 | B1 | 5/2007 | JP | 2005152416 A | 6/2005 |
| EP | 1785097 | A2 | 5/2007 | JP | 2005524474 A | 8/2005 |
| EP | 1790293 | A2 | 5/2007 | JP | 2006-281405 A | 10/2006 |
| EP | 1800610 | A1 | 6/2007 | RU | 2008830 C1 | 3/1994 |
| EP | 1300117 | B1 | 8/2007 | RU | 2187249 C2 | 8/2002 |
| EP | 1813199 | A1 | 8/2007 | RU | 2225170 C2 | 3/2004 |
| EP | 1813201 | A1 | 8/2007 | SU | 189517 A | 1/1967 |
| EP | 1813203 | A2 | 8/2007 | SU | 328636 A | 9/1972 |
| EP | 1813207 | A1 | 8/2007 | SU | 886900 A1 | 12/1981 |
| EP | 1813209 | A1 | 8/2007 | SU | 1333319 A2 | 8/1987 |
| EP | 1487359 | B1 | 10/2007 | SU | 1377053 A1 | 2/1988 |
| EP | 1599146 | B1 | 10/2007 | SU | 1561964 A1 | 5/1990 |
| EP | 1839596 | A1 | 10/2007 | SU | 1722476 A1 | 3/1992 |
| EP | 1402821 | B1 | 12/2007 | VU | WO 2004/019769 A1 | 3/2004 |
| EP | 1872727 | A1 | 1/2008 | WF | WO 2004/021868 A2 | 3/2004 |
| EP | 1897502 | A1 | 3/2008 | WO | WO 91/15157 A1 | 10/1991 |
| EP | 1330201 | B1 | 6/2008 | WO | WO 92/20295 A1 | 11/1992 |
| EP | 1702568 | B1 | 7/2008 | WO | WO 92/21300 A1 | 12/1992 |
| EP | 1943957 | A2 | 7/2008 | WO | WO 93/08755 A1 | 5/1993 |
| EP | 1593337 | B1 | 8/2008 | WO | WO 93/13718 A1 | 7/1993 |
| EP | 1970014 | A1 | 9/2008 | WO | WO 93/14690 A1 | 8/1993 |
| EP | 1980213 | A2 | 10/2008 | WO | WO 93/15648 A1 | 8/1993 |
| EP | 1759645 | B1 | 11/2008 | WO | WO 93/15850 A1 | 8/1993 |
| EP | 1990014 | A2 | 11/2008 | WO | WO 93/19681 A1 | 10/1993 |
| EP | 1693008 | B1 | 12/2008 | WO | WO 94/00060 A1 | 1/1994 |
| EP | 1759640 | B1 | 12/2008 | WO | WO 94/11057 A1 | 5/1994 |
| EP | 2000102 | A2 | 12/2008 | WO | WO 94/12108 A1 | 6/1994 |
| EP | 1736104 | B1 | 3/2009 | WO | WO 94/18893 A1 | 9/1994 |
| EP | 1749486 | B1 | 3/2009 | WO | WO 94/22378 A1 | 10/1994 |
| EP | 2039316 | A2 | 3/2009 | WO | WO 94/23659 A1 | 10/1994 |
| EP | 1721576 | B1 | 4/2009 | WO | WO 95/02369 A1 | 1/1995 |
| EP | 1733686 | B1 | 4/2009 | WO | WO 95/03743 A1 | 2/1995 |
| EP | 2044890 | A1 | 4/2009 | WO | WO 95/06817 A1 | 3/1995 |
| EP | 1550413 | B1 | 6/2009 | WO | WO 95/09576 A1 | 4/1995 |
| EP | 1745748 | B1 | 8/2009 | WO | WO 95/09577 A1 | 4/1995 |
| EP | 2090256 | A2 | 8/2009 | WO | WO 95/14436 A1 | 6/1995 |
| EP | 1813208 | B1 | 11/2009 | WO | WO 95/17855 A1 | 7/1995 |
| EP | 1607050 | B1 | 12/2009 | WO | WO 95/18383 A1 | 7/1995 |
| EP | 1566150 | B1 | 4/2010 | WO | WO 95/18572 A1 | 7/1995 |
| EP | 1813206 | B1 | 4/2010 | WO | WO 95/19739 A1 | 7/1995 |
| EP | 1769754 | B1 | 6/2010 | WO | WO 95/20360 A1 | 8/1995 |
| EP | 1535565 | B1 | 10/2010 | WO | WO 95/23557 A1 | 9/1995 |

| | | | | | | |
|---|---|---|---|---|---|---|
| WO | WO 95/24865 | A1 | 9/1995 | WO | WO 02/17799 A1 | 3/2002 |
| WO | WO 95/25471 | A3 | 9/1995 | WO | WO 02/19920 A1 | 3/2002 |
| WO | WO 95/26562 | A1 | 10/1995 | WO | WO 02/19932 A1 | 3/2002 |
| WO | WO 95/29639 | A1 | 11/1995 | WO | WO 02/30297 A2 | 4/2002 |
| WO | WO 96/04858 | A1 | 2/1996 | WO | WO 02/32322 A2 | 4/2002 |
| WO | WO 96/19151 | A1 | 6/1996 | WO | WO 02/36028 A1 | 5/2002 |
| WO | WO 96/19152 | A1 | 6/1996 | WO | WO 02/43571 A2 | 6/2002 |
| WO | WO 96/20652 | A1 | 7/1996 | WO | WO 02/058568 A1 | 8/2002 |
| WO | WO 96/21119 | A1 | 7/1996 | WO | WO 02/060328 A1 | 8/2002 |
| WO | WO 96/22055 | A1 | 7/1996 | WO | WO 02/067785 A2 | 9/2002 |
| WO | WO 96/23448 | A1 | 8/1996 | WO | WO 02/098302 A1 | 12/2002 |
| WO | WO 96/24301 | A1 | 8/1996 | WO | WO 03/000138 A2 | 1/2003 |
| WO | WO 96/27337 | A1 | 9/1996 | WO | WO 03/001329 A2 | 1/2003 |
| WO | WO 96/31155 | A1 | 10/1996 | WO | WO 03/013363 A1 | 2/2003 |
| WO | WO 96/35464 | A1 | 11/1996 | WO | WO 03/015604 A2 | 2/2003 |
| WO | WO 96/39085 | A1 | 12/1996 | WO | WO 03/020106 A2 | 3/2003 |
| WO | WO 96/39086 | A1 | 12/1996 | WO | WO 03/020139 A2 | 3/2003 |
| WO | WO 96/39087 | A1 | 12/1996 | WO | WO 03/024339 A1 | 3/2003 |
| WO | WO 96/39088 | A1 | 12/1996 | WO | WO 03/079909 A3 | 3/2003 |
| WO | WO 96/39089 | A1 | 12/1996 | WO | WO 03/030743 A2 | 4/2003 |
| WO | WO 97/00646 | A1 | 1/1997 | WO | WO 03/037193 A1 | 5/2003 |
| WO | WO 97/00647 | A1 | 1/1997 | WO | WO 03/047436 A3 | 6/2003 |
| WO | WO 97/06582 | A1 | 2/1997 | WO | WO 03/055402 A1 | 7/2003 |
| WO | WO 97/10763 | A1 | 3/1997 | WO | WO 03/057048 A1 | 7/2003 |
| WO | WO 97/10764 | A1 | 3/1997 | WO | WO 03/057058 A1 | 7/2003 |
| WO | WO 97/11648 | A2 | 4/1997 | WO | WO 03/063694 A1 | 8/2003 |
| WO | WO 97/11649 | A1 | 4/1997 | WO | WO 03/077769 A1 | 9/2003 |
| WO | WO 97/15237 | A1 | 5/1997 | WO | WO 03/079911 A1 | 10/2003 |
| WO | WO 97/24073 | A1 | 7/1997 | WO | WO 03/082126 A1 | 10/2003 |
| WO | WO 97/24993 | A1 | 7/1997 | WO | WO 03/088845 A2 | 10/2003 |
| WO | WO 97/30644 | A1 | 8/1997 | WO | WO 03/090630 A2 | 11/2003 |
| WO | WO 97/34533 | A1 | 9/1997 | WO | WO 03/094743 A1 | 11/2003 |
| WO | WO 97/37598 | A1 | 10/1997 | WO | WO 03/094745 A1 | 11/2003 |
| WO | WO 97/39688 | A2 | 10/1997 | WO | WO 03/094746 A1 | 11/2003 |
| WO | WO 98/17180 | A1 | 4/1998 | WO | WO 03/094747 A1 | 11/2003 |
| WO | WO 98/27880 | A1 | 7/1998 | WO | WO 03/101313 A1 | 12/2003 |
| WO | WO 98/30153 | A1 | 7/1998 | WO | WO 03/105698 A2 | 12/2003 |
| WO | WO 98/47436 | A1 | 10/1998 | WO | WO 03/105702 A2 | 12/2003 |
| WO | WO 99/03407 | A1 | 1/1999 | WO | WO 2004/006980 A1 | 1/2004 |
| WO | WO 99/03408 | A1 | 1/1999 | WO | WO 2004/011037 A2 | 2/2004 |
| WO | WO 99/03409 | A1 | 1/1999 | WO | WO 2004/028585 A2 | 4/2004 |
| WO | WO 99/12483 | A1 | 3/1999 | WO | WO 2004/032754 A2 | 4/2004 |
| WO | WO 99/12487 | A1 | 3/1999 | WO | WO 2004/032760 A2 | 4/2004 |
| WO | WO 99/12488 | A1 | 3/1999 | WO | WO 2004/032762 A1 | 4/2004 |
| WO | WO 99/15086 | A1 | 4/1999 | WO | WO 2004/032763 A2 | 4/2004 |
| WO | WO 99/15091 | A1 | 4/1999 | WO | WO 2004/034875 A2 | 4/2004 |
| WO | WO 99/23933 | A2 | 5/1999 | WO | WO 2004/047626 A1 | 6/2004 |
| WO | WO 99/23959 | A1 | 5/1999 | WO | WO 2004/047653 A2 | 6/2004 |
| WO | WO 99/25261 | A1 | 5/1999 | WO | WO 2004/049956 A2 | 6/2004 |
| WO | WO 99/29244 | A1 | 6/1999 | WO | WO 2004/052426 A2 | 6/2004 |
| WO | WO 99/34744 | A1 | 7/1999 | WO | WO 2004/056276 A1 | 7/2004 |
| WO | WO 99/45849 | A1 | 9/1999 | WO | WO 2004/056277 A1 | 7/2004 |
| WO | WO 99/48430 | A1 | 9/1999 | WO | WO 2004/062516 A1 | 7/2004 |
| WO | WO 99/51158 | A1 | 10/1999 | WO | WO 2004/078050 A2 | 9/2004 |
| WO | WO 00/24322 | A1 | 5/2000 | WO | WO 2004/078051 A2 | 9/2004 |
| WO | WO 00/24330 | A1 | 5/2000 | WO | WO 2004/086987 A1 | 10/2004 |
| WO | WO 00/41638 | A1 | 7/2000 | WO | WO 2004/096015 A2 | 11/2004 |
| WO | WO 00/48506 | A1 | 8/2000 | WO | WO 2004/096057 A2 | 11/2004 |
| WO | WO 00/53112 | A2 | 9/2000 | WO | WO 2004/103157 A2 | 12/2004 |
| WO | WO 00/54653 | A1 | 9/2000 | WO | WO 2004/105593 A1 | 12/2004 |
| WO | WO 00/57796 | A1 | 10/2000 | WO | WO 2004/105621 A1 | 12/2004 |
| WO | WO 00/64365 | A1 | 11/2000 | WO | WO 2004/112618 A2 | 12/2004 |
| WO | WO 00/72762 | A1 | 12/2000 | WO | WO 2004/112652 A2 | 12/2004 |
| WO | WO 00/72765 | A1 | 12/2000 | WO | WO 2005/027983 A2 | 3/2005 |
| WO | WO 01/03587 | A1 | 1/2001 | WO | WO 2005/037329 A2 | 4/2005 |
| WO | WO 01/05702 | A1 | 1/2001 | WO | WO 2005/044078 A2 | 5/2005 |
| WO | WO 01/10482 | A1 | 2/2001 | WO | WO 2005/055846 A2 | 6/2005 |
| WO | WO 01/35845 | A1 | 5/2001 | WO | WO 2005/072634 A2 | 8/2005 |
| WO | WO 01/54594 | A1 | 8/2001 | WO | WO 2005/078892 A1 | 8/2005 |
| WO | WO 01/58371 | A1 | 8/2001 | WO | WO 2005/079675 A2 | 9/2005 |
| WO | WO 01/62158 | A2 | 8/2001 | WO | WO 2005/096954 A2 | 10/2005 |
| WO | WO 01/62161 | A1 | 8/2001 | WO | WO 2005/112806 A2 | 12/2005 |
| WO | WO 01/62162 | A1 | 8/2001 | WO | WO 2005/112808 A1 | 12/2005 |
| WO | WO 01/62164 | A2 | 8/2001 | WO | WO 2005/115251 A2 | 12/2005 |
| WO | WO 01/62169 | A2 | 8/2001 | WO | WO 2005/117735 A1 | 12/2005 |
| WO | WO 01/78605 | A2 | 10/2001 | WO | WO 2005/122936 A1 | 12/2005 |
| WO | WO 01/91646 | A1 | 12/2001 | WO | WO 2006/027014 A1 | 3/2006 |
| WO | WO 02/07608 | A2 | 1/2002 | WO | WO 2006/044490 A2 | 4/2006 |
| WO | WO 02/07618 | A1 | 1/2002 | WO | WO 2006/044581 A2 | 4/2006 |

| | | |
|---|---|---|
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/089404 A2 | 7/2008 |
| WO | WO 2008/109125 A1 | 9/2008 |
| WO | WO 2010/063795 A1 | 6/2010 |

OTHER PUBLICATIONS

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

Partial European Search Report, Application 11163532.2, dated Aug. 4, 2011 (5 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Partial European Search Report, Application No. 08252151.9, dated Mar. 17, 2009 (4 pages).

European Search Report, Application No. 09250057.8, dated May 8, 2009 (7 pages).

European Search Report, Application No. 09250061.0, dated May 7, 2009 (7 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

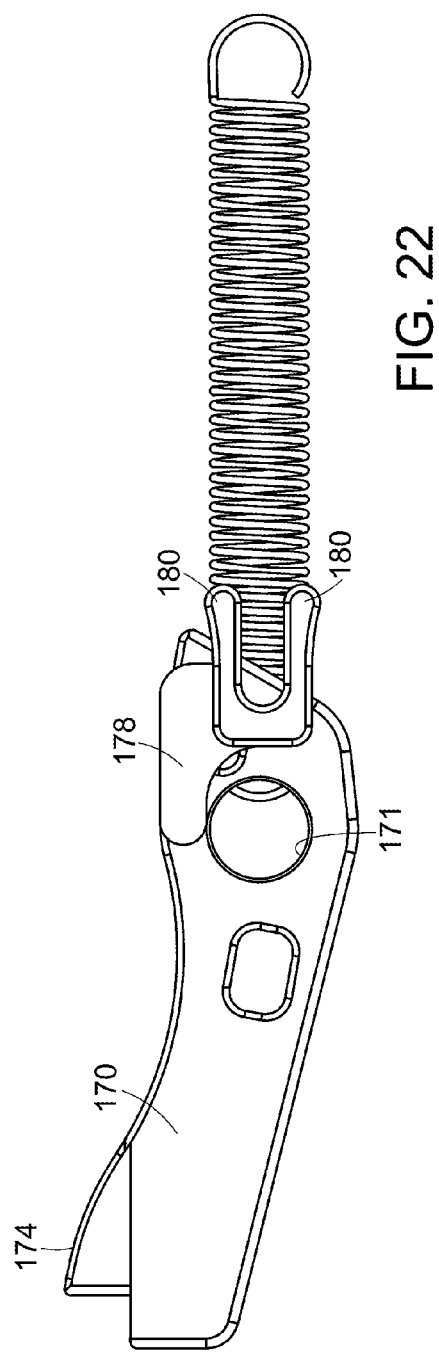
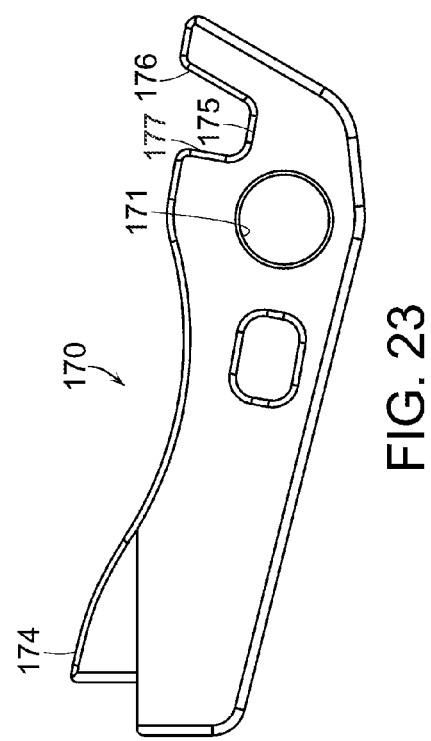

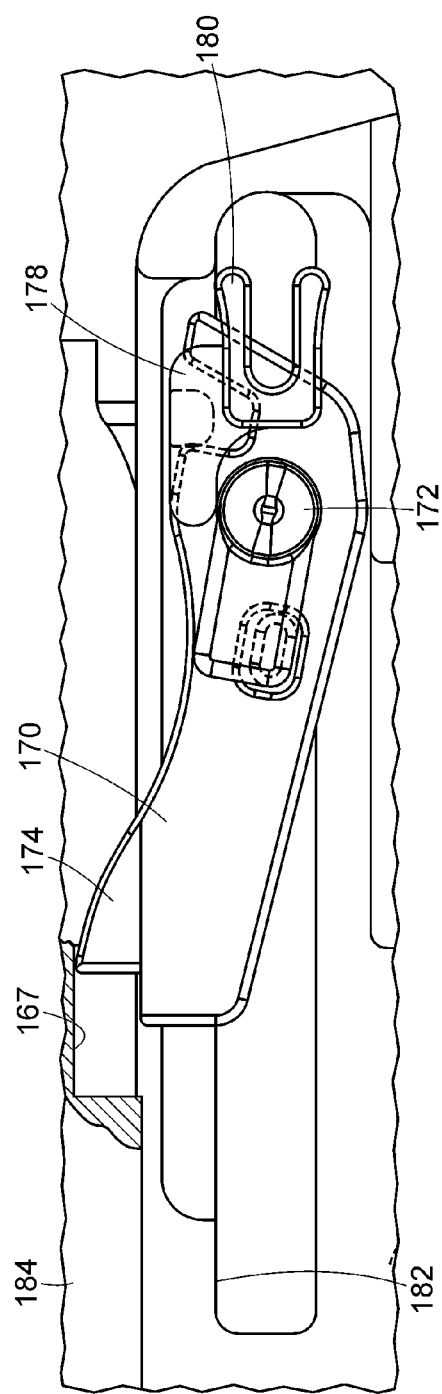
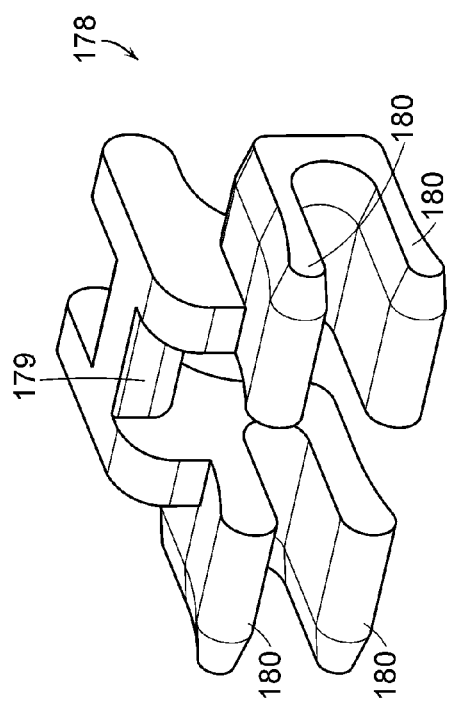

SURGICAL STAPLING INSTRUMENTS

CROSS REFERENCE TO RELATED APPLICATIONS

The present application is a divisional application claiming priority under 35 U.S.C. §121 to U.S. patent application Ser. No. 11/821,277, entitled "SURGICAL STAPLING INSTRUMENTS," filed Jun. 22, 2007 now U.S. Pat. No. 7,753,245, the entire disclosure of which is incorporated by reference herein.

The present application is related to the following commonly-owned U.S. patent applications filed on Jun. 22, 2007, and which are hereby incorporated by reference in their entirety:

(1) U.S. patent application Ser. No. 11/821,425, now U.S. Pat. No. 7,597,229, entitled END EFFECTOR CLOSURE SYSTEM FOR A SURGICAL STAPLING INSTRUMENT;

(2) U.S. patent application Ser. No. 11/821,426, now U.S. Pat. No. 7,604,150, entitled SURGICAL STAPLING INSTRUMENT WITH AN ANTI-BACK UP MECHANISM;

(3) U.S. patent application Ser. No. 11/821,347, now U.S. Pat. No. 7,441,685, entitled SURGICAL STAPLING INSTRUMENT WITH A RETURN MECHANISM; and (4) U.S. patent application Ser. No. 11/821,455, now U.S. Pat. No. 7,549,564, entitled SURGICAL STAPLING INSTRUMENT WITH AN ARTICULATING END EFFECTOR.

BACKGROUND

1. Field of the Invention

The present invention generally relates to surgical stapling instruments and, more particularly, to surgical staplers having a closing system for closing an end effector and a firing system for deploying staples.

2. Description of the Related Art

As known in the art, surgical staplers are often used to deploy staples into soft tissue in order to reduce or eliminate bleeding from the soft tissue, especially as the tissue is being transected, for example. Surgical staplers, such as an endocutter, for example, can comprise an end effector which can be moved, or articulated, with respect to an elongate shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge. These closing systems, however, do not prevent the end effector from being articulated relative to the shaft assembly after the jaw members have been closed. As a result, when the end effector is articulated, the end effector may apply a shear force to the soft tissue captured between the jaw members.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

After the driver and the cutting member have been advanced within the end effector, it is often necessary to retract the driver and/or cutting member to their starting positions. Previous surgical staplers have included a return spring which retracts the cutting member relative to the staple cartridge after a release button or toggle switch on the surgical stapler has been actuated by the surgeon, for example. In various embodiments, a first end of the return spring can be connected to the housing of the surgical instrument and a second end of the spring can be connected to the cutting member. Such staplers, however, are often difficult to use as the force required to extend the return spring as the cutting member is advanced is often significant. Furthermore, such return springs often apply a biasing force to the cutting member as it is advanced which can, in various circumstances, prematurely return the cutting member, especially in embodiments where multiple strokes of a trigger are required to completely advance the cutting member. What is needed is an improvement over the foregoing.

SUMMARY

In at least one form of the invention, a surgical instrument can include a shaft assembly, an end effector movable relative to the shaft assembly, and a locking mechanism configured to engage the shaft assembly and/or the end effector in order to fix, or lock, the relative relationship between the shaft assembly and the end effector. In various embodiments, the end effector can include an anvil and a channel where the channel can be configured to receive a staple cartridge and the anvil can be movably coupled to the channel. In at least one embodiment, the surgical instrument can further include a closure system configured to generate a closing motion where the anvil can be responsive to the closing motion. In various embodiments, the closure system can be further configured to engage the locking mechanism and prevent the locking mechanism from unlocking the relative relationship between the shaft assembly and the end effector.

In at least one form of the invention, a surgical instrument can include a closure system configured to move an anvil of an end effector, for example, between an open position, a partially closed position, and a closed position. In various embodiments, the surgical instrument can further include a lock member configured to selectively engage and lock the closure system when the anvil is positioned in one of its partially closed and closed positions. In at least one embodiment, the surgical instrument can include a trigger configured to pivot the anvil, for example, where the trigger can include a cam surface and a first notch in the cam surface. In various embodiments, the lock member can include a follower portion and the closure drive can include a lock spring configured to bias the follower portion against the cam surface of the trigger such that the follower portion can engage the first notch of the trigger when the anvil is pivoted into its partially closed position. In at least one embodiment, when the follower portion is engaged with the first notch, the first notch can prevent the anvil from being pivoted into its open position. In various embodiments, the cam portion can further include a second notch and the follower portion can be configured to engage the second notch when the anvil is pivoted into its closed position.

In at least one form of the invention, a surgical instrument can include a firing drive comprising a firing member configured to advance a cutting member within an end effector, for example, and a flexible band connected to the firing member configured to retract the firing member. In at least one embodiment, the surgical instrument can include a brake configured to engage the band, for example, and thereby limit the movement of the firing member. In various embodiments, the firing drive can further include a reel configured to wind up at least a portion of the band when the firing member is retracted. In at least one embodiment, the firing drive can further include a trigger selectively engageable with the firing member and the reel such that, when the trigger is operably engaged with the firing member, an actuation of the trigger can be configured to advance the firing member, and, when the trigger is operably engaged with the reel, an actuation of the trigger can be configured to rotate the reel and retract the firing member via the band.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 22 is an elevational view of the pawl, tilter mechanism, and a pawl return spring of the firing drive of FIG. 19;

FIG. 23 is an elevational view of the pawl of FIG. 22;

FIG. 24 is a detail view of the firing drive of FIG. 19 illustrating the pawl pivoted into a position to engage a firing link of the firing drive;

FIG. 25 is a perspective view of the tilter mechanism of FIG. 22;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 3:
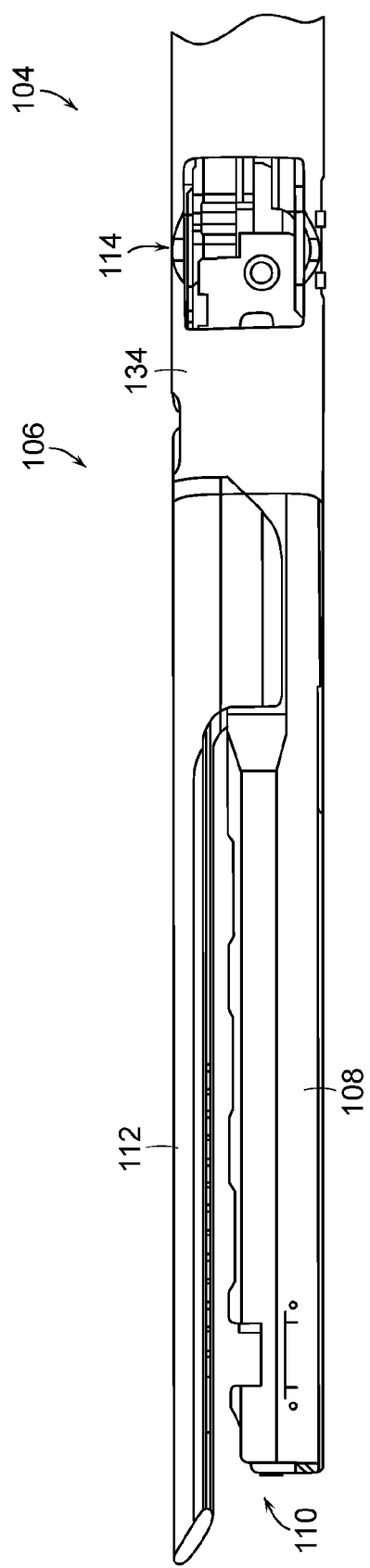
FIG. 3 is an elevational view of an end effector of the surgical instrument of FIG. 1.
Figure 4:
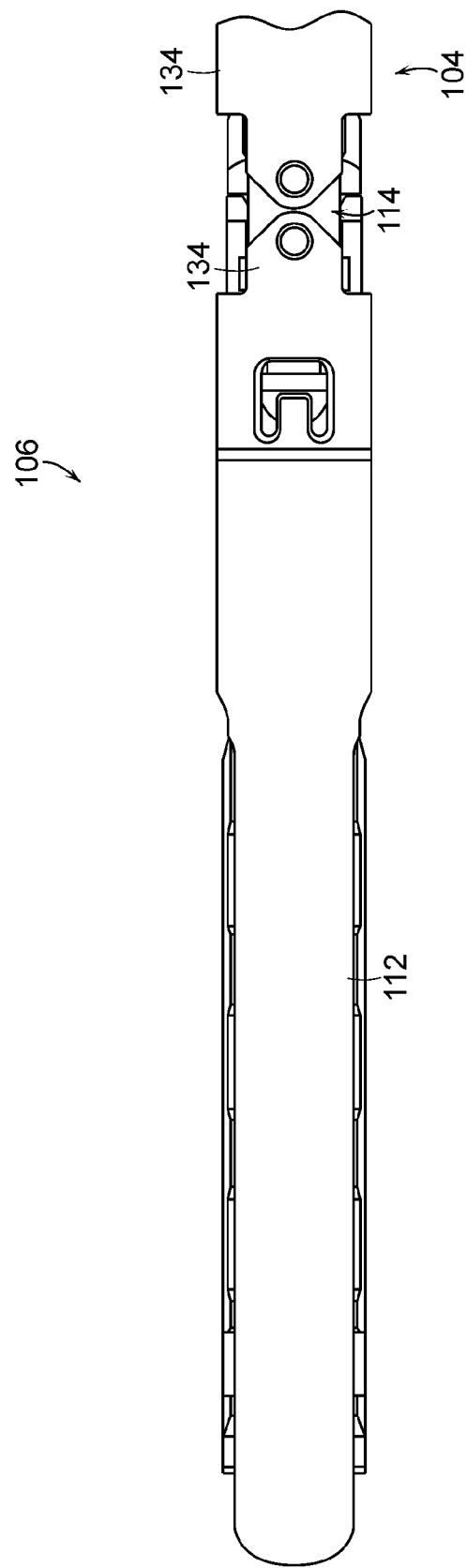
FIG. 4 is a top view of the end effector of FIG. 3.

In various embodiments, a surgical instrument in accordance with the present invention can be configured to insert surgical staples into soft tissue, for example. In at least one embodiment, referring to FIGS. 1-4, surgical instrument 100 can include handle portion 102, elongate shaft assembly 104, and end effector 106. In various embodiments, referring to FIGS. 3 and 4, end effector 106 can include staple cartridge channel 108 and staple cartridge 110, where staple cartridge 110 can be configured to removably store staples therein. In at least one embodiment, end effector 106 can further include anvil 112 which can be pivotably connected to staple cartridge channel 108 and can be pivoted between open and closed positions by an end effector closure system. In order to deploy the staples from staple cartridge 110, surgical instrument 100 can further include a staple driver configured to traverse staple cartridge 110 and a firing drive configured to advance the staple driver within the staple cartridge. In various embodiments, anvil 112 can be configured to deform at least a portion of the staples as they are deployed from the staple cartridge. Although various embodiments of an end effector closure system and a firing drive are described in further detail below, several embodiments of end effector closure systems and firing drives are disclosed in U.S. Pat. No. 6,905,057, entitled SURGICAL STAPLING INSTRUMENT INCORPORATING A FIRING MECHANISM HAVING A LINKED RACK TRANSMISSION, which issued on Jun. 14, 2005, and U.S. Pat. No. 7,044,352, entitled SURGICAL STAPLING INSTRUMENT HAVING A SINGLE LOCKOUT MECHANISM FOR PREVENTION OF FIRING, which issued on May 16, 2006, the entire disclosures of which are hereby incorporated by reference herein.

In various embodiments, a surgical instrument in accordance with the present invention can include a system for moving, or articulating, an end effector relative to an elongate shaft assembly of the surgical instrument. In at least one embodiment, referring to FIGS. 3-7, surgical instrument 100 can include articulation joint 114 which can movably connect end effector 106 and elongate shaft assembly 104. In various embodiments, articulation joint 114 can permit end effector 106 to be moved relative to shaft assembly 104 in a single plane or, alternatively, multiple planes. In either event, articulation joint 114 can include one or more pivot axes 116 (FIG. 5) about which end effector 106 can be articulated. In various embodiments, referring to FIGS. 5 and 6, surgical instrument 100 can further include locking mechanism 118 which can fix, or lock, the relative relationship between end effector 106 and elongate shaft assembly 104. In at least one embodiment, locking mechanism 118 can include lock member 120 which can be slid relative to end effector 106 and engage end effector 106 in order to prevent, or at least partially inhibit, relative movement between end effector 106 and shaft assembly 104. In at least one embodiment, lock member 120 can be configured to engage at least one of teeth 312 (FIGS. 5 and 6) of end effector 106 such that the interaction between lock member 120 and teeth 312 can prevent, or at least partially inhibit, end effector 106 from rotating about axis 116 as described in greater detail further below.

Figure 6:
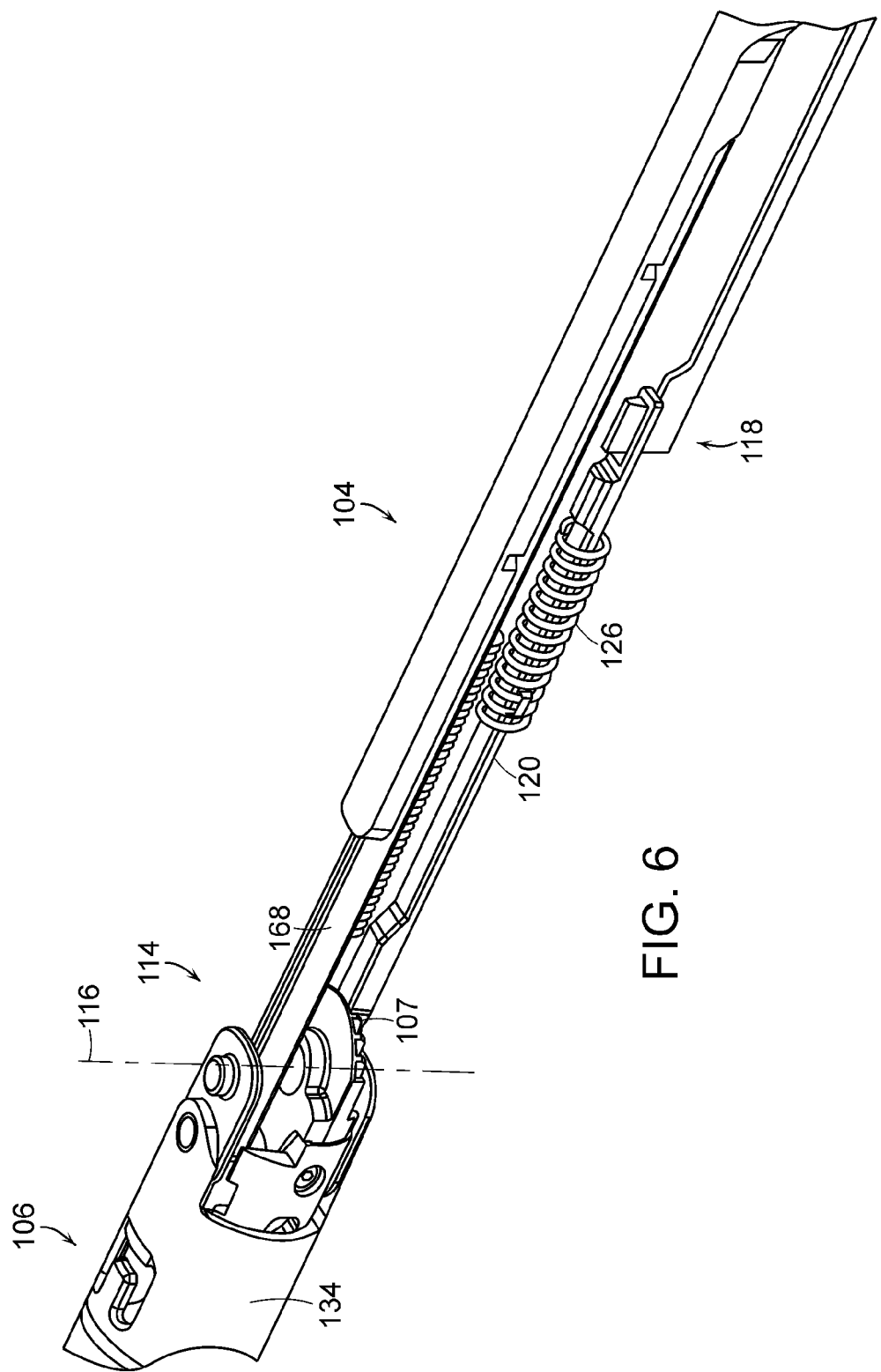
FIG. 6 is a perspective view of an elongate shaft assembly and the articulation joint of the surgical instrument of FIG. 1 with some components of the surgical instrument removed.
Figure 7:
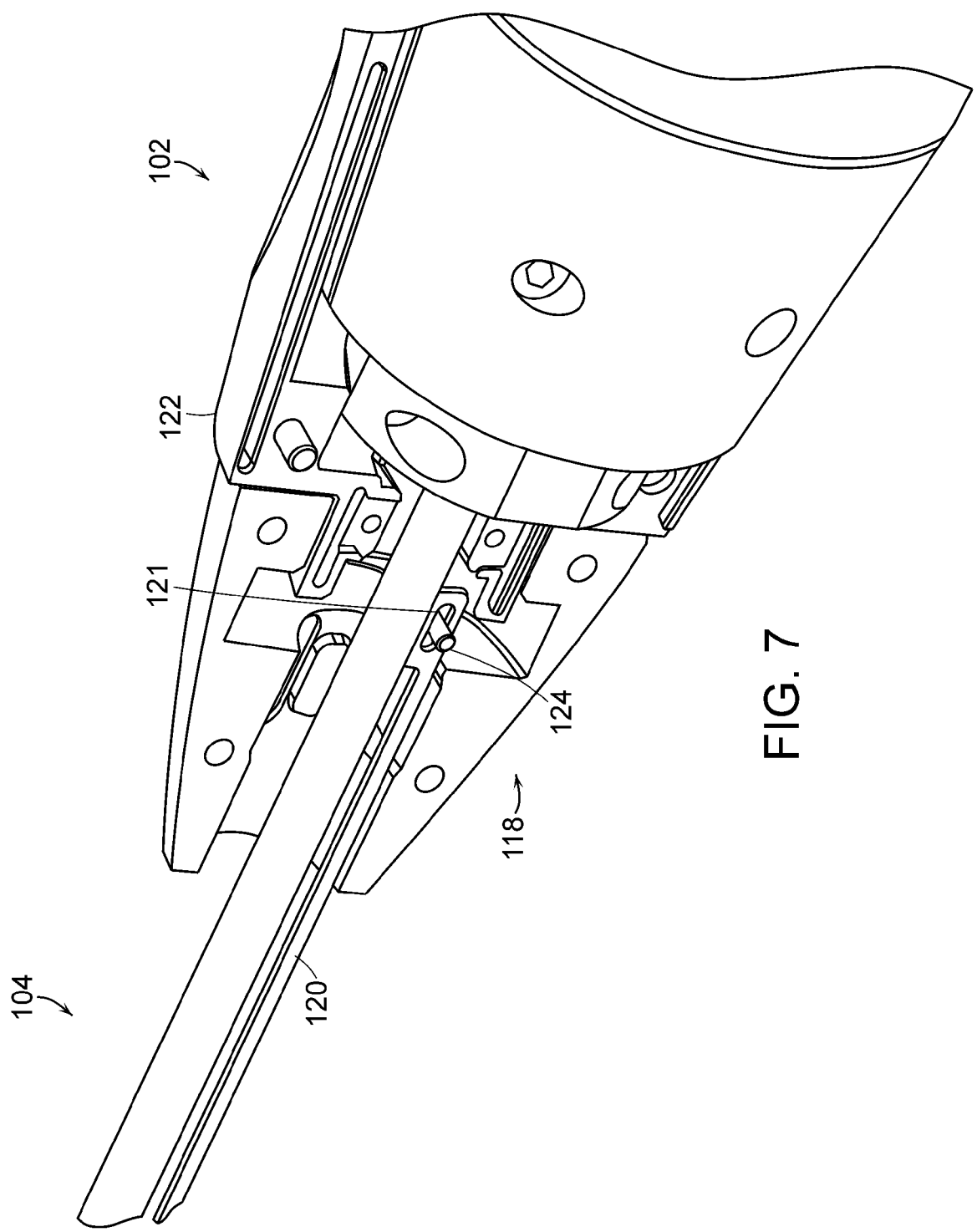
FIG. 7 is a partial perspective view of the handle portion and the elongate shaft assembly of the surgical instrument of FIG. 1 with some components of the surgical instrument removed.
Figure 8:
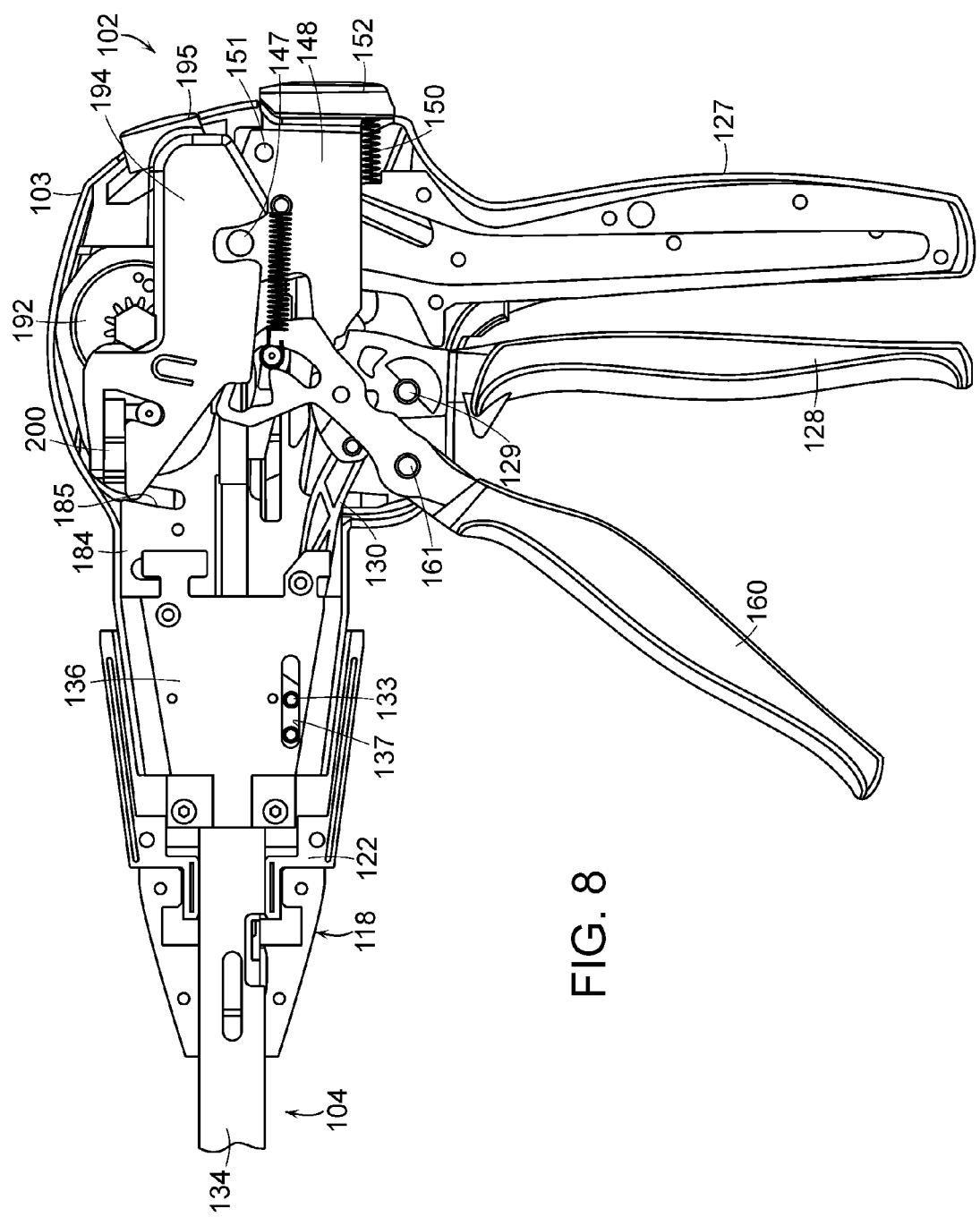
FIG. 8 is an elevational view of the handle portion of FIG. 2 with some components of the surgical instrument removed.
Figure 9:
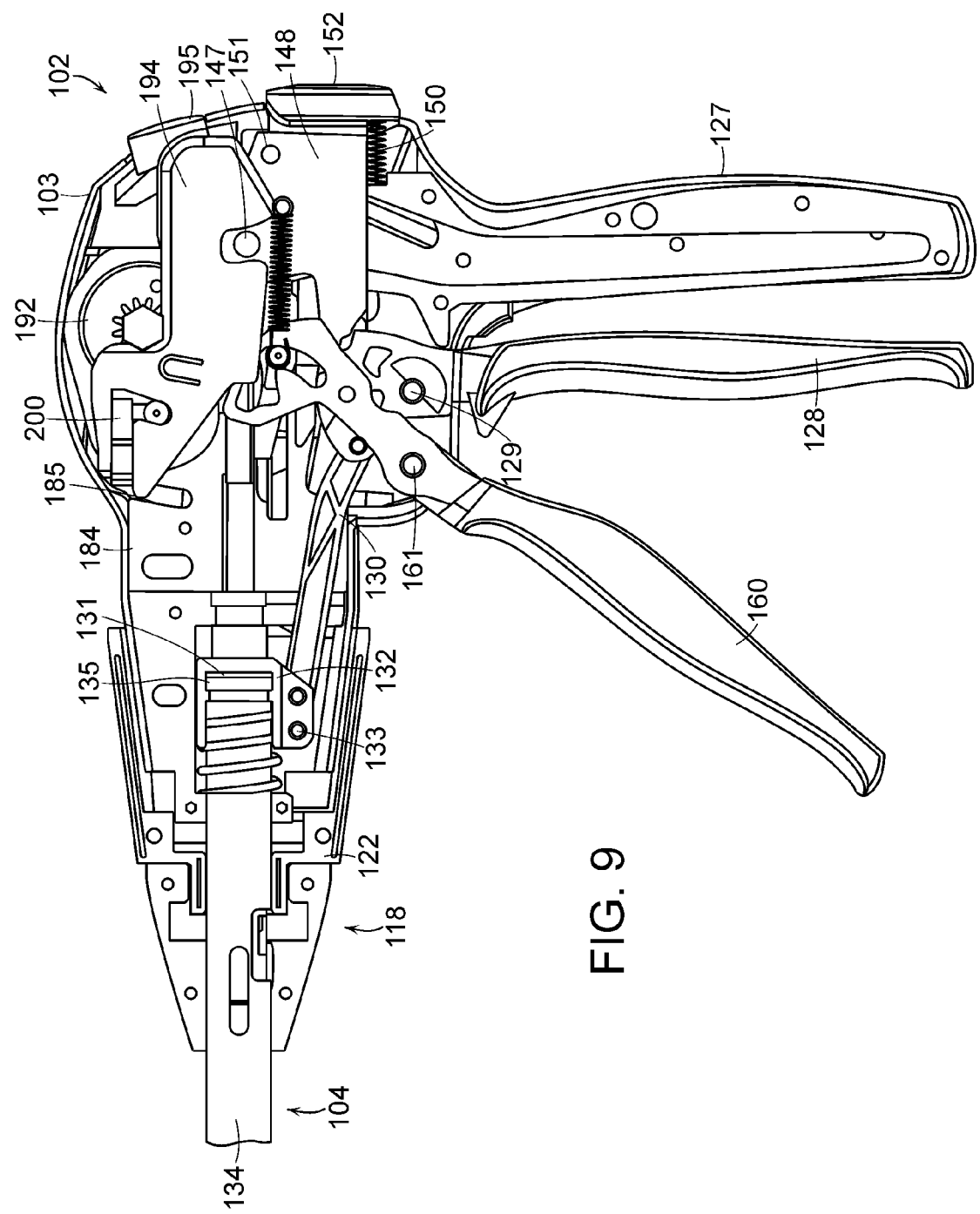
FIG. 9 is an elevational view of the handle portion of FIG. 2 with additional components of the surgical instrument removed.

In various embodiments, referring to FIGS. 7-9, locking mechanism 118 can further include actuator 122 which can be operably connected to lock member 120. In at least one embodiment, actuator 122 can include pin 124 which can be received within slot 121 in lock member 120 such that, when actuator 122 is slid relative to handle portion 102, pin 124 can abut a side wall of slot 121 and motivate lock member 120 relative to end effector 106. In at least one embodiment, actuator 122 can be pulled away from end effector 106, i.e., proximally, to disengage lock member 120 from end effector 106. Although not illustrated, other embodiments are envisioned where actuator 122 can be moved distally, or even rotated, in order to disengage lock member 120 from end effector 106. In either event, locking mechanism 118 can further include return spring 126 (FIG. 6) which can be configured to move lock member 120 toward end effector 106, i.e., distally, to engage lock member 120 with end effector 106 after actuator 122 has been released. Other locking mechanisms are disclosed in U.S. patent application Ser. No. 11/100,772, entitled SURGICAL INSTRUMENT WITH ARTICULATING SHAFT WITH SINGLE PIVOT CLOSURE AND DOUBLE PIVOT FRAME GROUND, which was filed on Apr. 7, 2005, U.S. patent application Ser. No. 11/238,358, entitled SURGICAL INSTRUMENT WITH ARTICULATING SHAFT WITH RIGID FIRING BAR SUPPORTS, which was filed on Sep. 29, 2005, and U.S. patent application Ser. No. 11/491,626, entitled SURGICAL STAPLING AND CUTTING DEVICE AND METHOD FOR USING THE DEVICE, which was filed on Jul. 24, 2006, the entire disclosures of which are hereby incorporated by reference herein.

Figure 1:
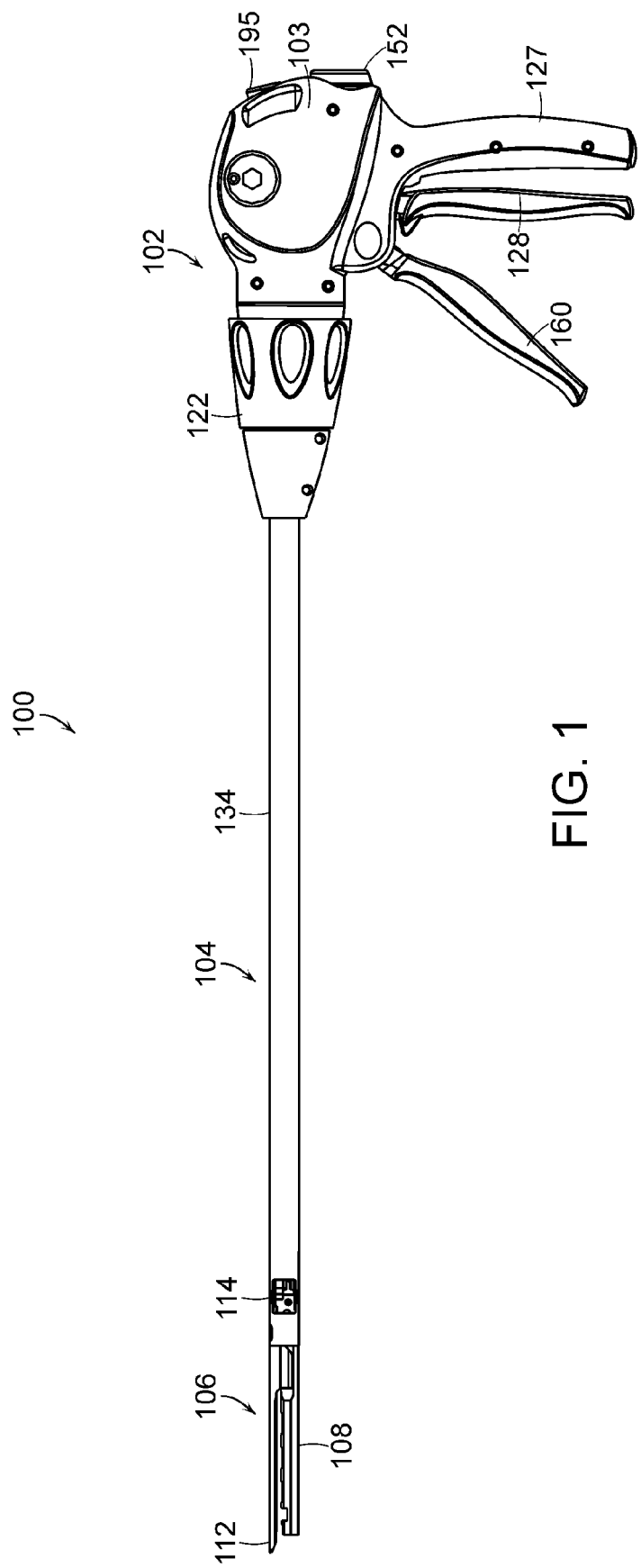
FIG. 1 is an elevational view of a surgical instrument in accordance with an embodiment of the present invention.
Figure 2:
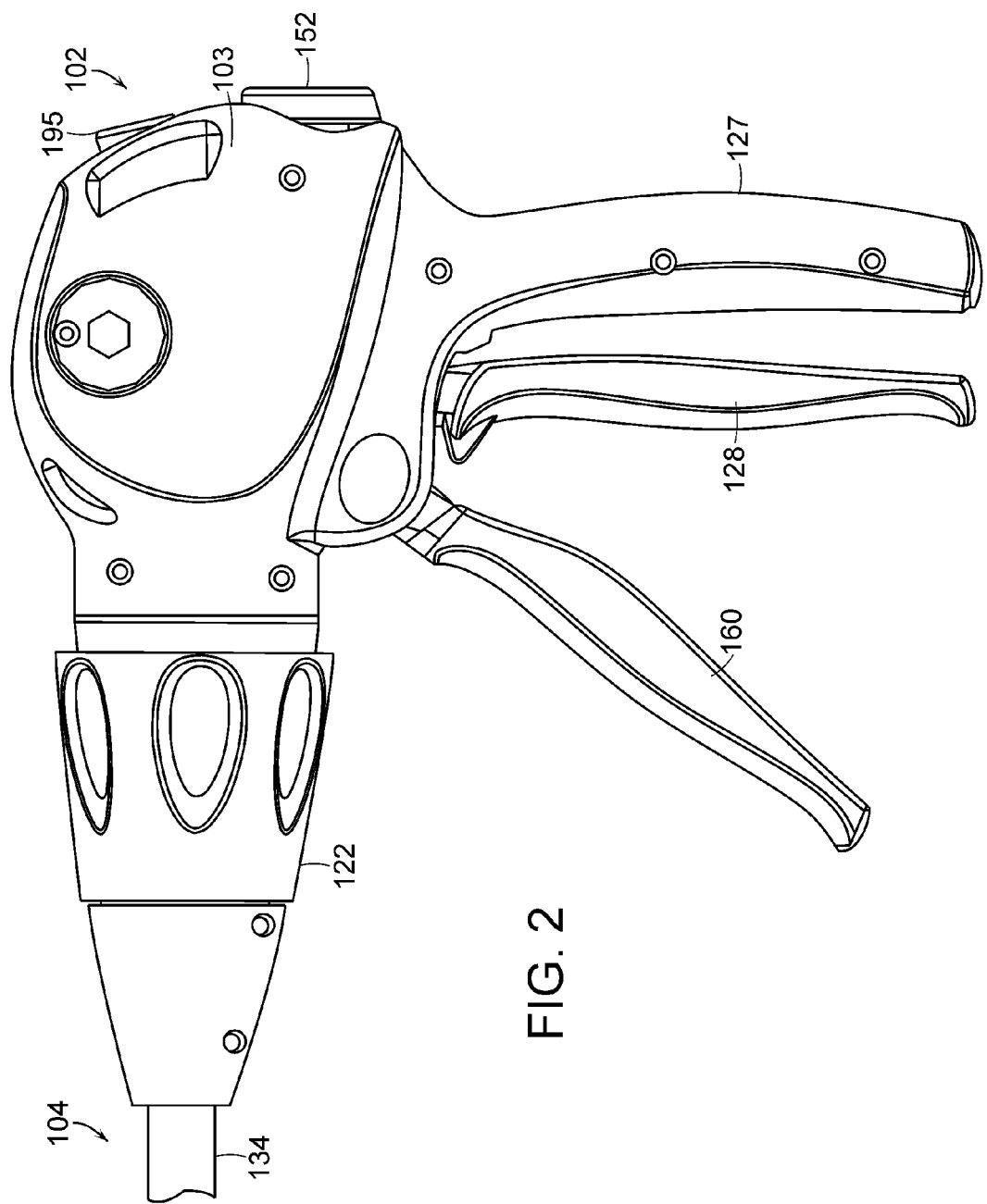
FIG. 2 is an elevational view of a handle portion of the surgical instrument of FIG. 1.

In various embodiments, referring to FIGS. 1 and 2, actuator 122 can be contoured such that a surgeon can grasp the outer surface of actuator 122 and pull actuator 122 proximally as described above. To move actuator 122, in at least one embodiment, a surgeon may place one hand on handle grip 127, for example, and place their other hand on actuator 122 so that the surgeon can move actuator 122 relative to handle grip 127. In other various embodiments, referring to FIGS. 10-13, actuator 122' can be configured such that a surgeon may only need one hand to operate the surgical instrument. More particularly, in at least one embodiment, actuator 122' can include hooks, or projections, 115 extending therefrom which can allow the surgeon to hold handle grip 127 with one hand and extend at least one finger from that hand distally to grip at least one projection 115 and pull actuator 122' proximally as described above. While actuator 122' is described herein as having projections 115, actuator 122, or any other suitable actuator, can also include projections 115 and/or any other suitable features that can assist a surgeon in operating surgical instrument 100 with one hand. In at least one embodiment, projections 115 can be at least partially comprised of and/or coated with an elastic or 'soft-touch' material which can improve the surgeon's grip on projections 115 and can provide other ergonomic benefits to the surgeon. In various embodiments, actuator 122', for example, can be operably engaged with shaft assembly 104 such that end effector 106 and shaft assembly 104 can be rotated about a longitudinal axis by actuator 122'. In such embodiments, a surgeon can orient end effector 106 in a surgical site by articulating end effector 106 as described above and/or rotating end effector 106 into position. In at least one embodiment, the surgeon can rotate actuator 122' by positioning a finger against one of projections 115 and applying a force thereto. In various embodiments, the surgeon can hold actuator 122' in position by placing a finger against a projection 115 and resisting any undesired motion of actuator 122' and, correspondingly, end effector 106.

Figure 5:
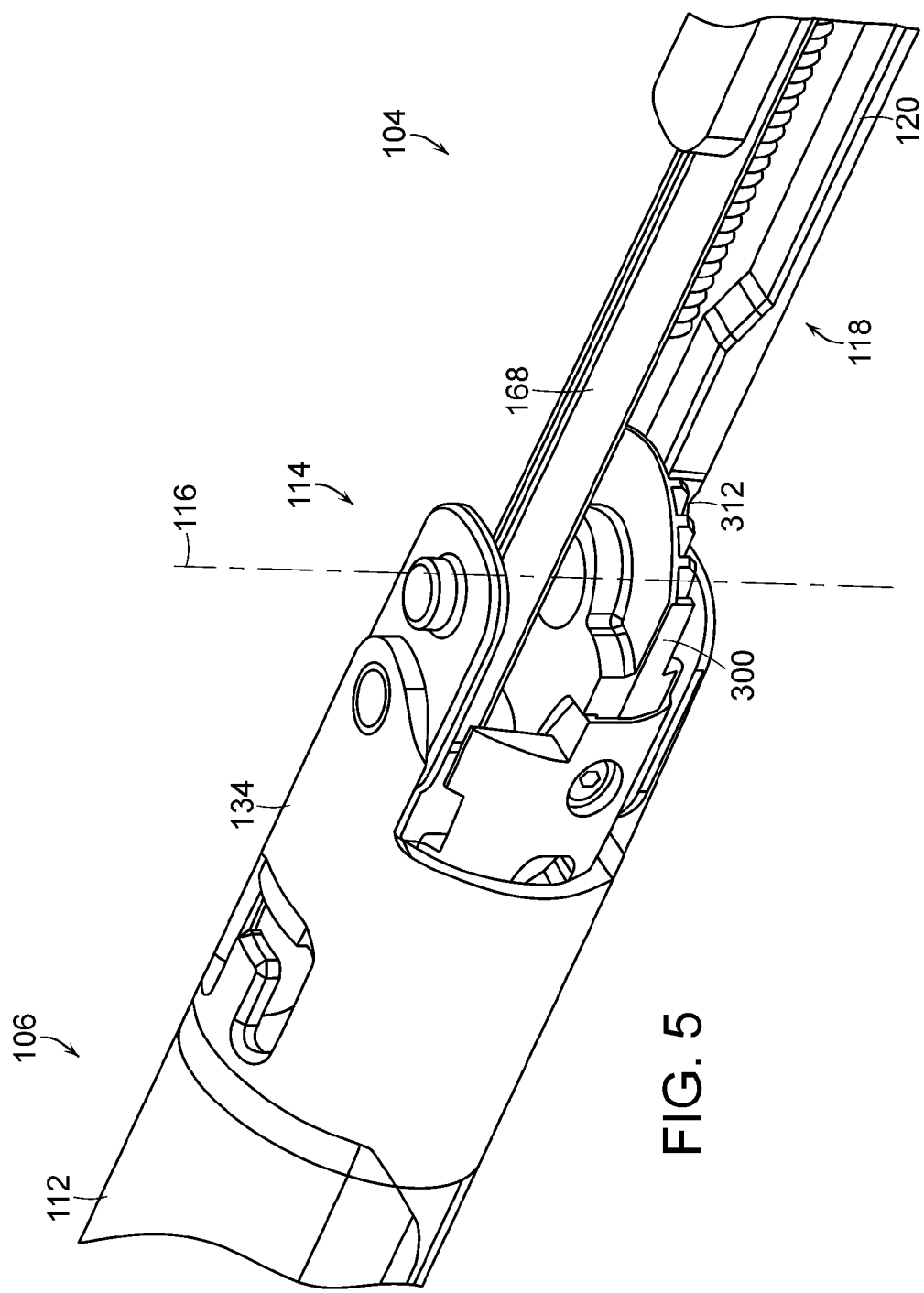
FIG. 5 is a perspective view of an articulation joint of the surgical instrument of FIG. 1 with some components of the surgical instrument removed.

In various embodiments, a surgical instrument in accordance with the present invention can include a system for closing, or clamping, an end effector onto soft tissue, for example. In at least one embodiment, referring to FIGS. 2, 5, 8 and 9, surgical instrument 100 can include closure trigger 128, drive link 130, driver 132, and closure tube 134. In various embodiments, upon an actuation of closure trigger 128, closure trigger 128 can be configured to displace drive link 130, driver 132, and closure tube 134 distally. More particularly, in at least one embodiment, drive link 130 can include a first end pivotably connected to trigger 128 and a second end pivotably connected to driver 132 such that the rotation of trigger 128 toward handle grip 127 can drive link 130 forward and slide driver 132 along an axis defined by driver guide 136 (FIG. 8). In various embodiments, driver 132 can include projections 133 extending therefrom which can be slidably received within slots 135 in driver guide 136 such that slots 135 can define a path for driver 132 as it is moved. In various embodiments, closure tube 134 can be operably engaged with driver 132 such that, when driver 132 is moved distally as described above, closure tube 134 can engage anvil 112 and pivot anvil 112 downwardly. Referring primarily to FIG. 5, closure tube 134 can be configured to slide over articulation joint 114 and pivot anvil 112 relative to staple cartridge 110. In at least one embodiment, as illustrated in FIG. 9, closure tube 134 can include a proximal end having projection 135 extending therefrom which can be received in slot 131 in driver 132 such that the displacement of driver 132 is transmitted to closure tube 134.

Figure 10:
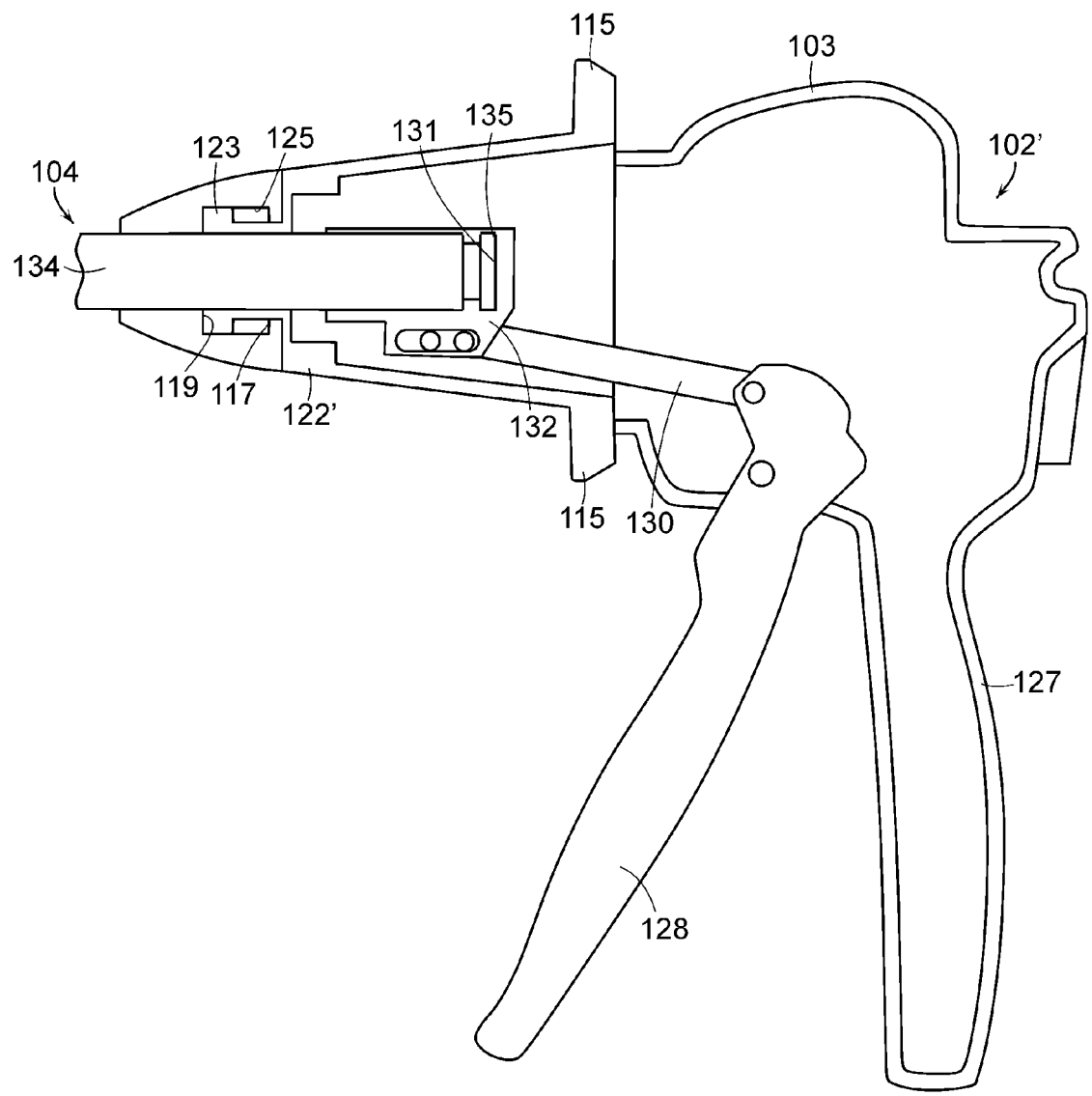
FIG. 10 is an elevational view of an actuator of an articulation locking mechanism and an end effector closure system of a surgical instrument in accordance with an alternative embodiment of the present invention with some components of the surgical instrument removed.
Figure 11:
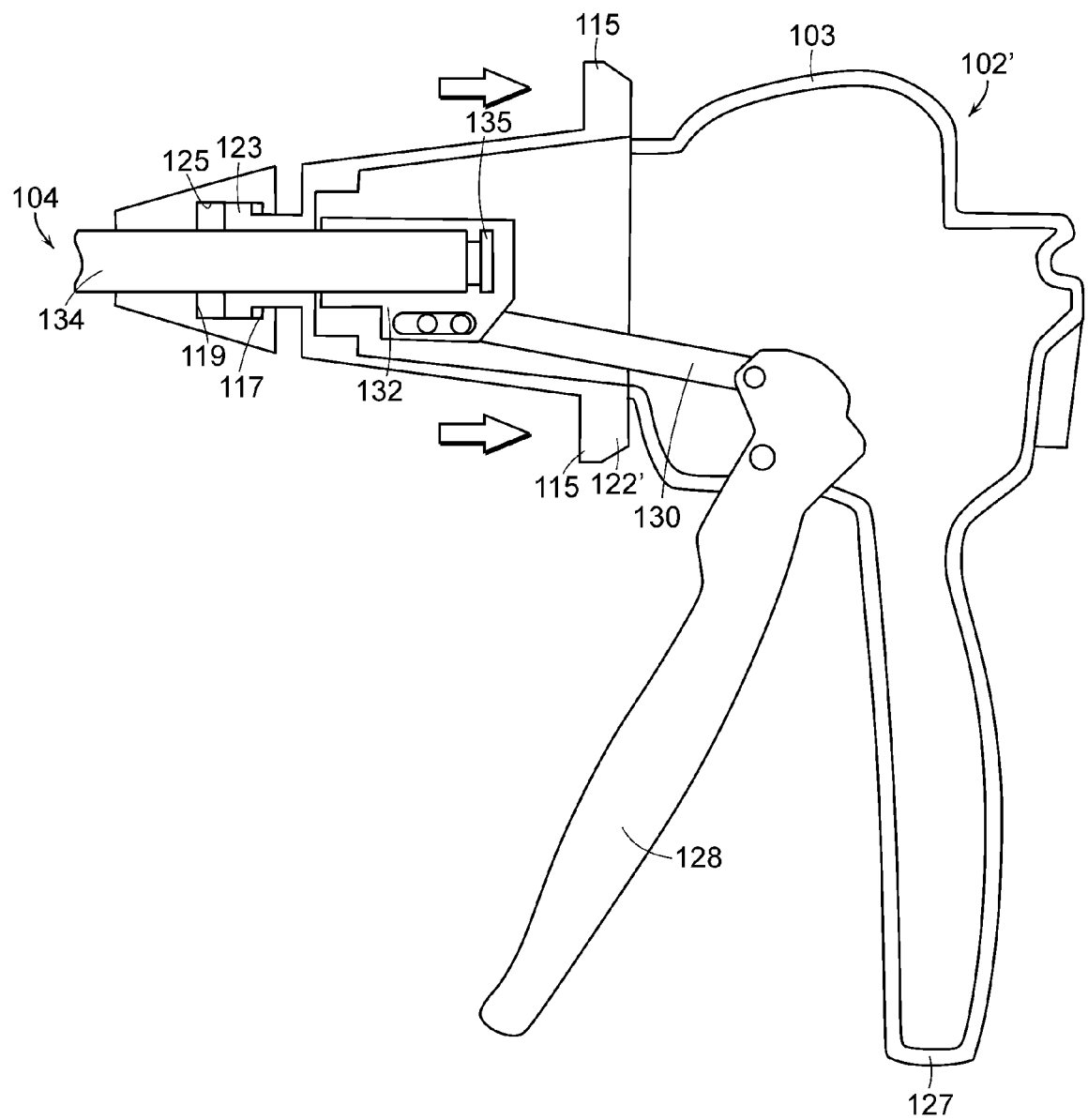
FIG. 11 is an elevational view of the surgical instrument of FIG. 10 illustrating the articulation locking mechanism actuator in an unlocked position and the end effector closure system in an open configuration.
Figure 12:
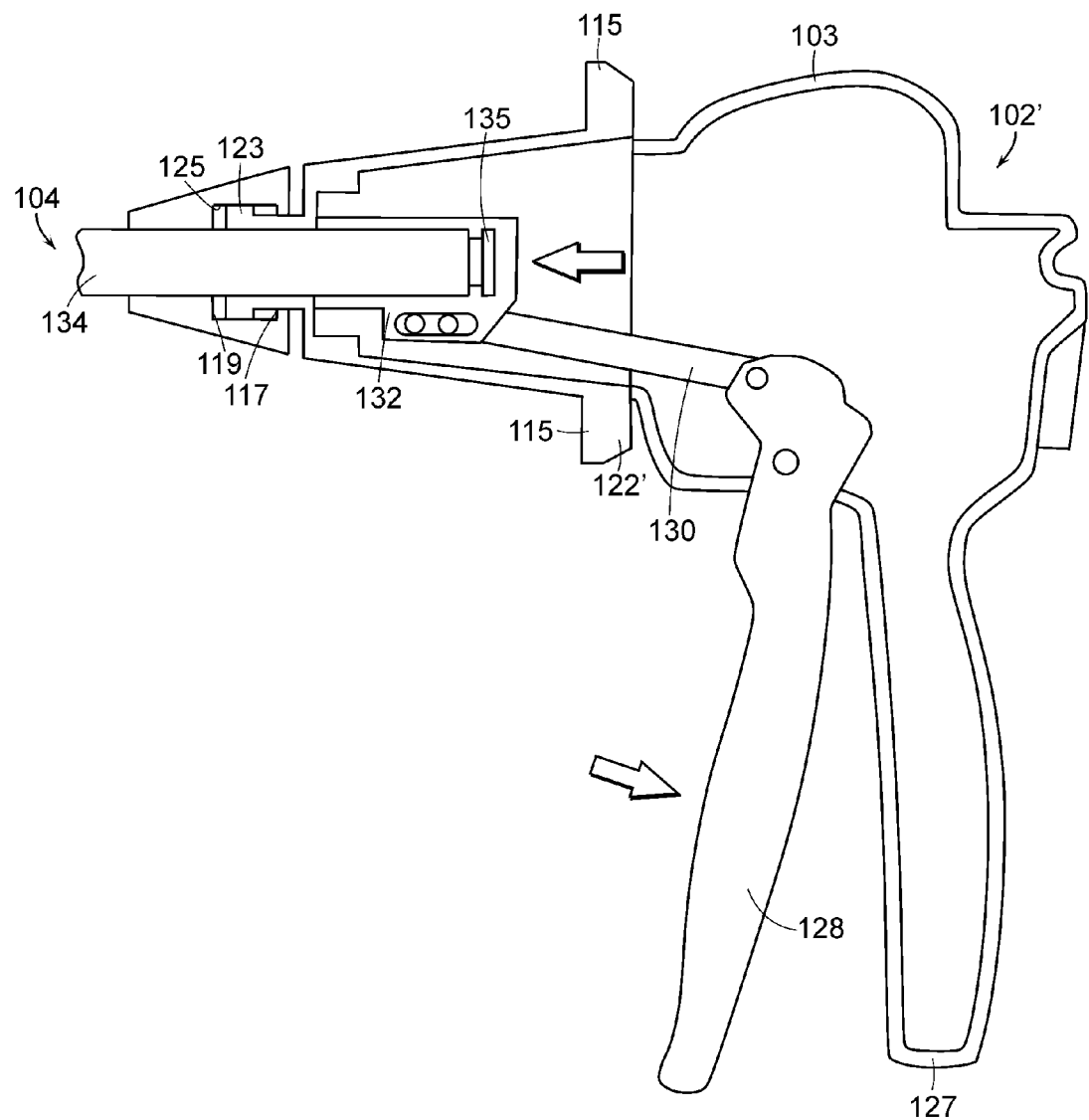
FIG. 12 is an elevational view of the surgical instrument of FIG. 10 illustrating the articulation locking mechanism actuator in an unlocked position and the end effector closure system in a partially closed configuration.

In various embodiments, as described above, locking mechanism 118 can prevent, or at least partially inhibit, relative movement between end effector 106 and shaft assembly 104. In circumstances where soft tissue is clamped between anvil 112 and staple cartridge 110, for example, relative movement between end effector 106 and shaft assembly 104 can apply a shear force to the soft tissue clamped therebetween which may damage it. In various embodiments, referring to FIGS. 10-13, in order to prevent, or at least reduce, relative movement between end effector 106 and shaft assembly 104 when end effector 106 is closed, the end effector closure system can be configured to engage locking mechanism 118 to prevent actuator 122' from being moved into its unlocked position. In effect, in at least one embodiment, the actuation of closure trigger 128 can not only close end effector 106, but it can also prevent locking mechanism 118 from being unlocked. In various embodiments, referring to FIGS. 10-13, surgical instrument 100' can include driver 132 which can be configured to abut, or be positioned closely adjacent to, actuator 122' when driver 132 is moved distally by trigger 128 and thereby prevent actuator 122' from being moved proximally as described above with respect to actuator 122. More particularly, before trigger 132 is actuated, as illustrated in FIGS. 10 and 11, actuator 122' can be slid proximally in order to slide lock member 120 relative to end effector 106 and unlock articulation joint 114. Upon an actuation of trigger of 132, however, referring to FIG. 13, driver 132 can be configured to abut, or be positioned adjacent to, actuator 122' such that actuator 122' cannot be moved proximally to disengage lock member 120 from end effector 106. As a result, the end effector closure system can prevent end effector 106 from being articulated after it has been closed, thereby reducing the possibility that a shear force will be transmitted to the soft tissue clamped therein.

Further to the above, the end effector closure system can provide feedback to the surgeon that the end effector has been closed and, in order for the surgeon to unlock and articulate the end effector, the surgeon must first at least partially re-open the end effector before the end effector can be articulated. More particularly, owing to the interaction between driver 132 and actuator 122' when end effector 106 is closed, when a surgeon attempts to pull actuator 122' proximally to unlock articulation joint 114, driver 132 can substantially prevent actuator 122' from moving thereby signaling to the surgeon that end effector 106 is closed and end effector 106 must first be opened before actuator 122' can be moved and the articulation joint can be unlocked. In various embodiments, such an end effector closure system can prevent the surgeon from damaging the surgical instrument and/or tissue captured within, or surrounding, the end effector. More particularly, in at least one embodiment, when closure tube 134 has been advanced to close anvil 112 as described above, closure tube 134 may apply a force to anvil 112 to maintain anvil 112 in a closed position and, in various circumstances, this force can create friction forces within articulation joint 114 which can inhibit, if not prevent, end effector 106 from rotating about articulation joint 114. In embodiments without the end effector closure system described above, if a surgeon attempts to overcome these friction forces without first at least partially opening the end effector, the surgeon may bend or break one or more components of the surgical instrument, for example. In various embodiments of the present invention, however, driver 132, for example, may prevent the surgeon from releasing articulation lock 120 as described above and, as a result, the surgeon may not be afforded the opportunity to unlock articulation joint 114 let alone articulate end effector 106.

In various embodiments, a surgical instrument in accordance with the present invention can include an end effector closure system which can position anvil 112, for example, in an open position, a closed position, and a partially closed position. In at least one embodiment, a surgeon can move an anvil 112 into a partially closed position and evaluate whether the end effector should be repositioned or articulated before anvil 112 is moved into its closed position. In such embodiments, anvil 112 can be moved relative to soft tissue positioned intermediate anvil 112 and staple cartridge 110 without applying a shear force, or at least a substantial shear force, to the soft tissue before anvil 112 is completely closed. In at least one embodiment, anvil 112 can be configured such that it does not clamp the soft tissue positioned between anvil 112 and staple cartridge 110 when it is in its partially closed position. Alternatively, anvil 112 can be configured to apply a light clamping force to the soft tissue when anvil 112 is in its partially closed position before applying a larger clamping force when it is moved into its closed position. In at least one such embodiment, the surgical instrument can include a trigger which can be moved between a first position (FIG. 11) which corresponds to the open position of anvil 112, a second position (FIG. 12) which corresponds with its partially closed position, and a third position (FIG. 13) which corresponds with its closed position. In various embodiments, referring to FIGS. 8 and 9, trigger 128 can be pivotably mounted to housing 103 of handle portion 102 such that trigger 128 can be rotated about pin 129 between its first, second, and third positions. In various embodiments, referring to FIGS. 8, 9, 17 and 18, surgical instrument 100 can further include trigger lock 148 which can be configured to engage trigger 128 and selectively lock trigger 128 in at least one of its first, second, and third positions described above. In at least one embodiment, trigger 128 can include pivot end 138 comprising cam surface 140, first notch 142, and second notch 144 where trigger lock 148 can be configured to engage first notch 142 and second notch 144. More particularly, surgical instrument 100 can further include, referring to FIGS. 8 and 9, trigger lock spring 150 which can be configured to bias follower portion 149 of trigger lock 148 against cam surface 140 such that when either first notch 142 or second notch 144 is aligned with follower portion 149, trigger lock spring 150 can push follower portion 149 into first notch 142 or second notch 144, respectively. In at least one embodiment, referring primarily to FIGS. 8 and 9, trigger lock 148 can be pivotably mounted to housing 103 of handle portion 102 via pin 151. In various embodiments, trigger lock spring 150 can be compressed intermediate button portion 152 of trigger lock 148 and housing 103 such that trigger lock spring 150 can rotate trigger lock 148 about pin 151 and bias trigger lock 148 downwardly against cam surface 140 of trigger 128.

Further to the above, in at least one embodiment, first notch 142 can be aligned with follower portion 149 when trigger 132 is moved into its second position and anvil 112 is moved into its partially closed position. In various embodiments, follower portion 149 can be securely retained within first notch 142 such that trigger lock 148 may need to be manually disengaged from trigger 132 before trigger 132 can be moved into its third position and/or returned to its first position. In at least one embodiment, referring to FIGS. 8 and 9, a surgeon can depress button portion 152 of lock member 148 such that lock member 148 is rotated about pin 151 and follower portion 149 is lifted upwardly and out of engagement with trigger 128. In other various embodiments, first notch 142 can be configured such that follower portion 149 can slide out of first notch 142 upon an application of force to trigger 132. In either event, after follower portion 149 has been disengaged from first notch 142, a surgeon can selectively move trigger 132 into its third position or release trigger 132 and allow a trigger spring, for example, to return trigger 132 to its first position. In at least one alternative embodiment, first notch 142 and follower portion 149 can be configured such that, after trigger 132 has been moved into its second position, trigger 132 must be moved into its third position before it can be returned into its first position. In either event, in at least one embodiment, second notch 144 of trigger 132 can be aligned with follower portion 149 when trigger 132 is moved into its third position and anvil 112 is moved into its closed position. Similar to first notch 142, second notch 144 can be configured to retain follower portion 149 therein until lock member 148 is disengaged from trigger 132 and/or a sufficient force is applied to trigger 132 to dislodge follower portion 149 from second notch 144. Thereafter, in various embodiments, a trigger spring can move trigger 132 from its third position into its second position where the surgeon may be required to, similar to the above, disengage follower portion 149 from first notch 142. In at least one alternative embodiment, first notch 142 can be configured such that follower portion 149 can slide past first notch 142 and allow trigger 132 to be moved from its third position to its first position without requiring the surgeon to dislodge follower portion 149 from first notch 142.

Further to the above, although not illustrated, button portion 152 of lock member 148 can be recessed, for example, within surgical instrument housing 103 when closure trigger 128 is in its first position. In alternative embodiments, button portion 152 can be positioned flushly with housing 103 or it can extend slightly from housing 103. In either event, in at least one embodiment, button portion 152 can move outwardly relative to housing 103 when closure trigger 128 is moved into its second position. Such movement can provide visual feedback to the surgeon that the anvil of the surgical instrument is in its partially closed position. In addition, the movement of button portion 152 can also be accompanied by audio and/or tactile feedback. In either event, a surgeon can access button portion 152 after it has been moved outwardly such that lock member 148 can be disengaged from trigger 128 as described above. In various embodiments, button portion 152 can move outwardly even further when trigger 128 is moved from its second position to its third position. Similar to the above, such movement can provide a visual cue to the surgeon that the anvil is now in its closed position and can be accompanied by audio and/or tactile feedback, as described above. Although button 152 is described above as moving outwardly as trigger 128 is progressed between its first and third positions, the invention is not so limited. On the contrary, button 152, or any other suitable indicator, can be provide feedback to the surgeon in any suitable manner.

In alternative embodiments, although not illustrated, anvil 112 can be held, or retained, in more than the three positions described above, i.e., its open, closed, and partially-closed positions. In at least one embodiment, anvil 112 can be retained in open, closed, and two or more intermediate positions. In such embodiments, anvil 112 could be progressed through these intermediate positions and apply an increasingly greater force to the soft tissue captured in end effector 106 as anvil 112 is moved toward its closed position. In at least one embodiment, similar to the above, trigger 132 could include a plurality of notches which could correspond with the various intermediate positions of anvil 112. In various alternative embodiments, although not illustrated, the end effector closure system could include a ratchet assembly which could allow trigger 132 and, correspondingly, anvil 112 to be held in a plurality of positions. In such embodiments, anvil 112 and trigger 132 could be held in place by a pawl pivotably engaged with a ratchet wheel operably engaged with trigger 132.

Figure 13:
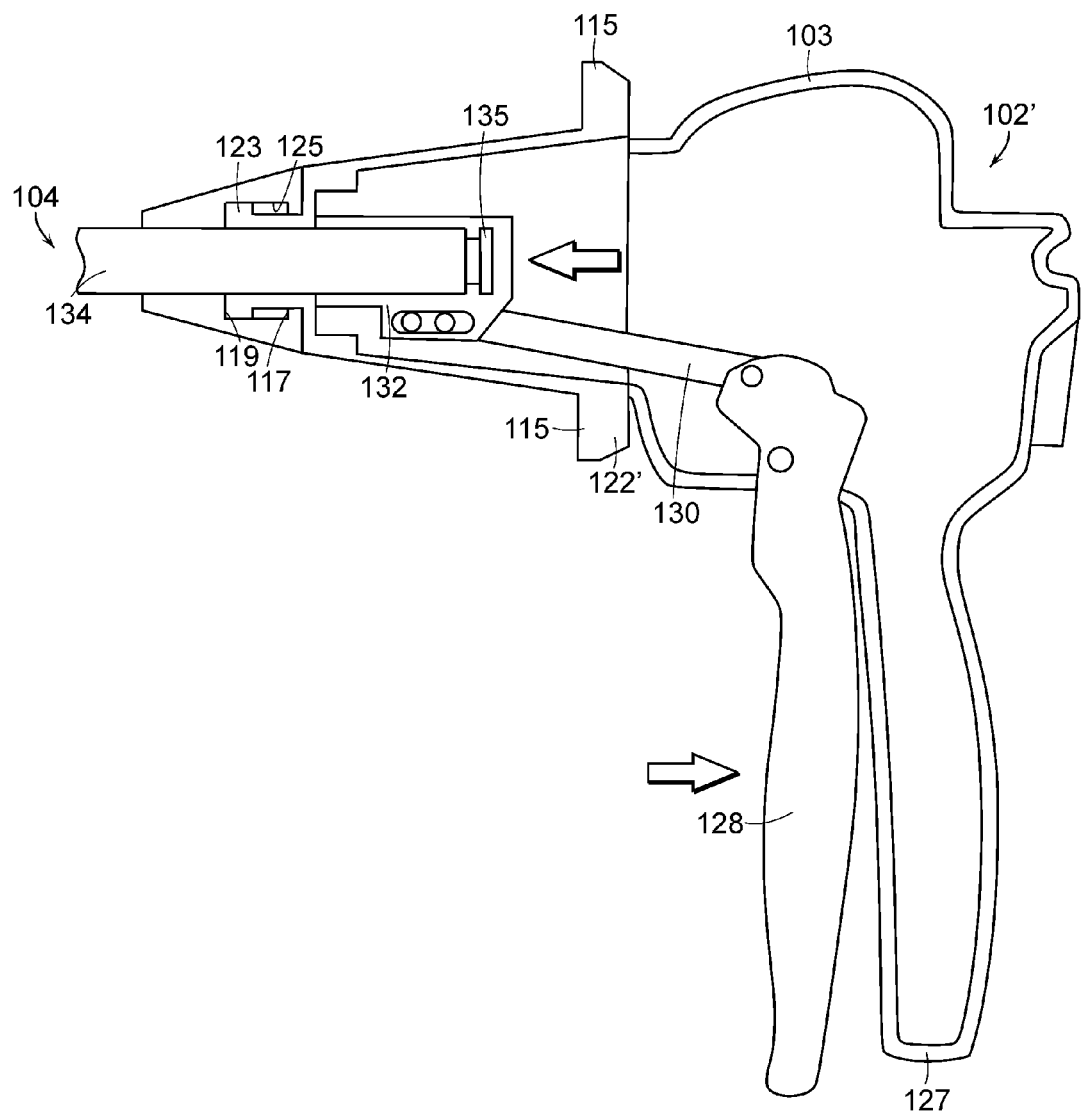
FIG. 13 is an elevational view of the surgical instrument of FIG. 10 illustrating the articulation locking mechanism actuator in a locked position and the end effector closure system in a closed configuration.
Figure 14:
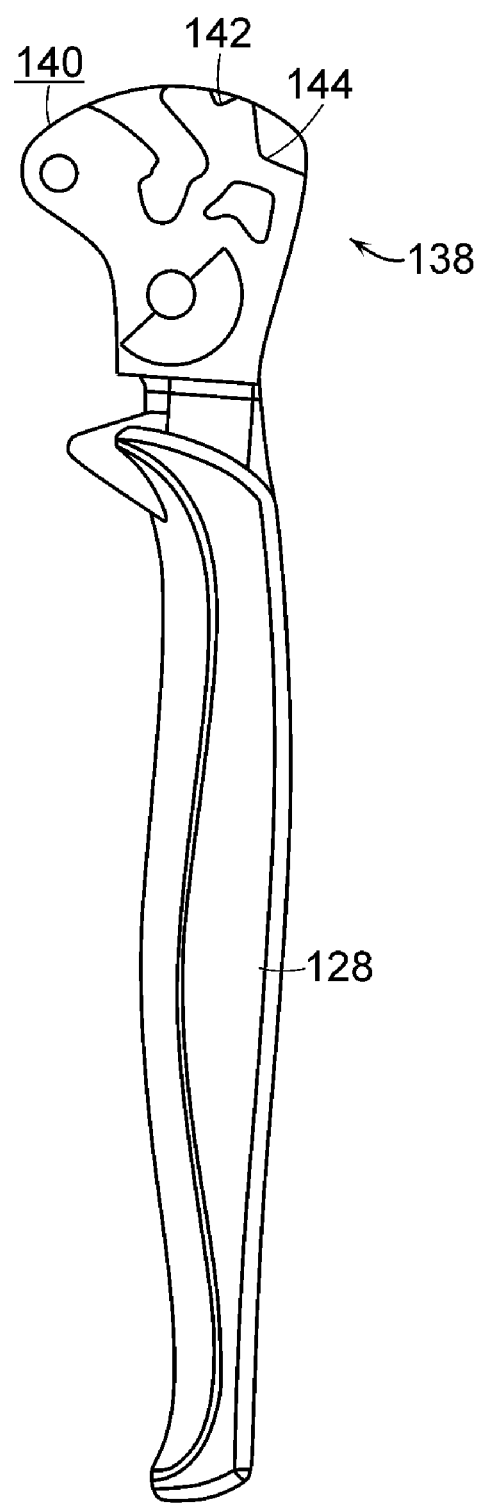
FIG. 14 is an elevational view of a closure trigger of an end effector closure system of the surgical instrument of FIG. 1.
Figure 15:
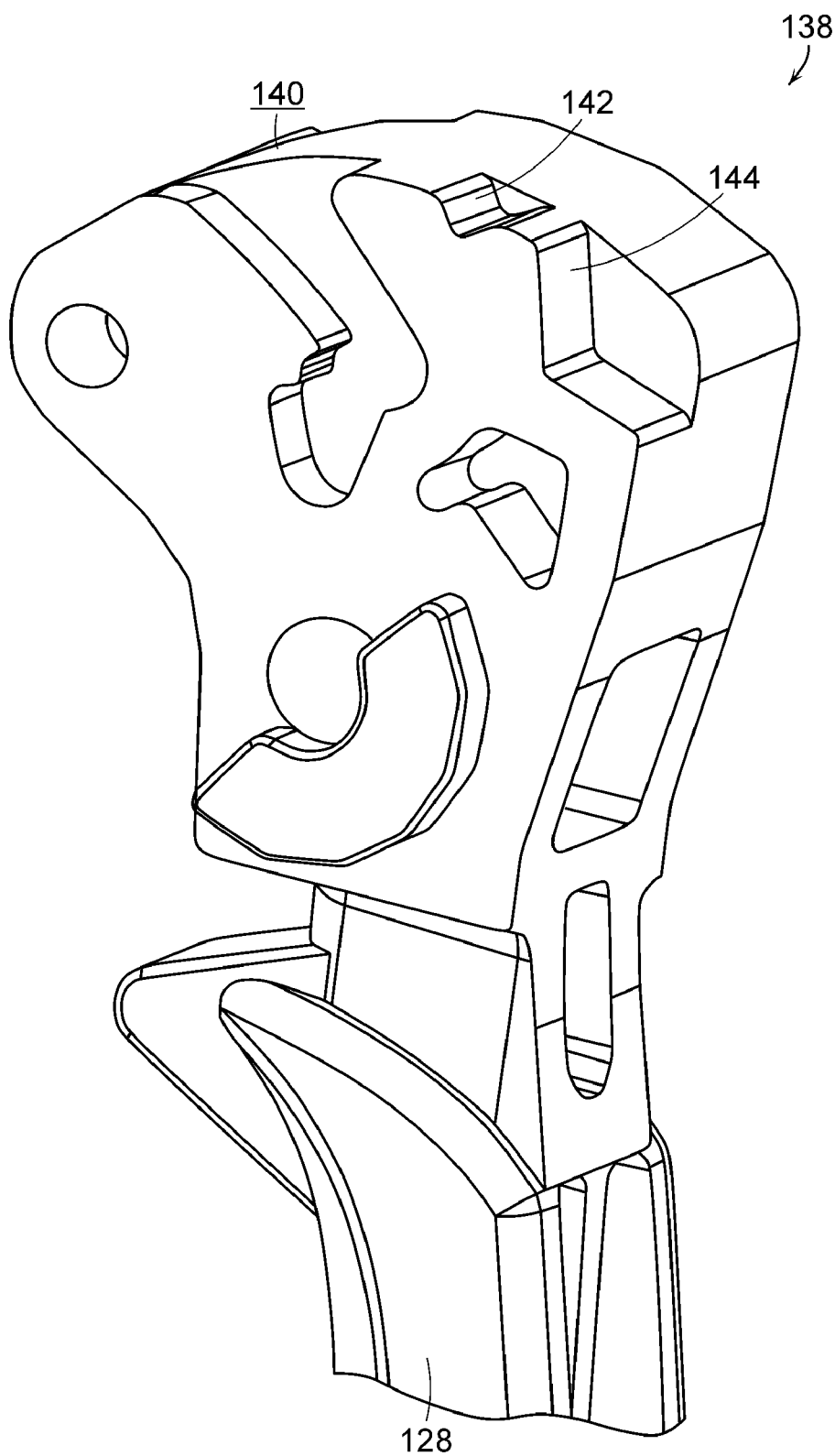
FIG. 15 is a partial perspective view of the closure trigger of FIG. 15.
Figure 16:
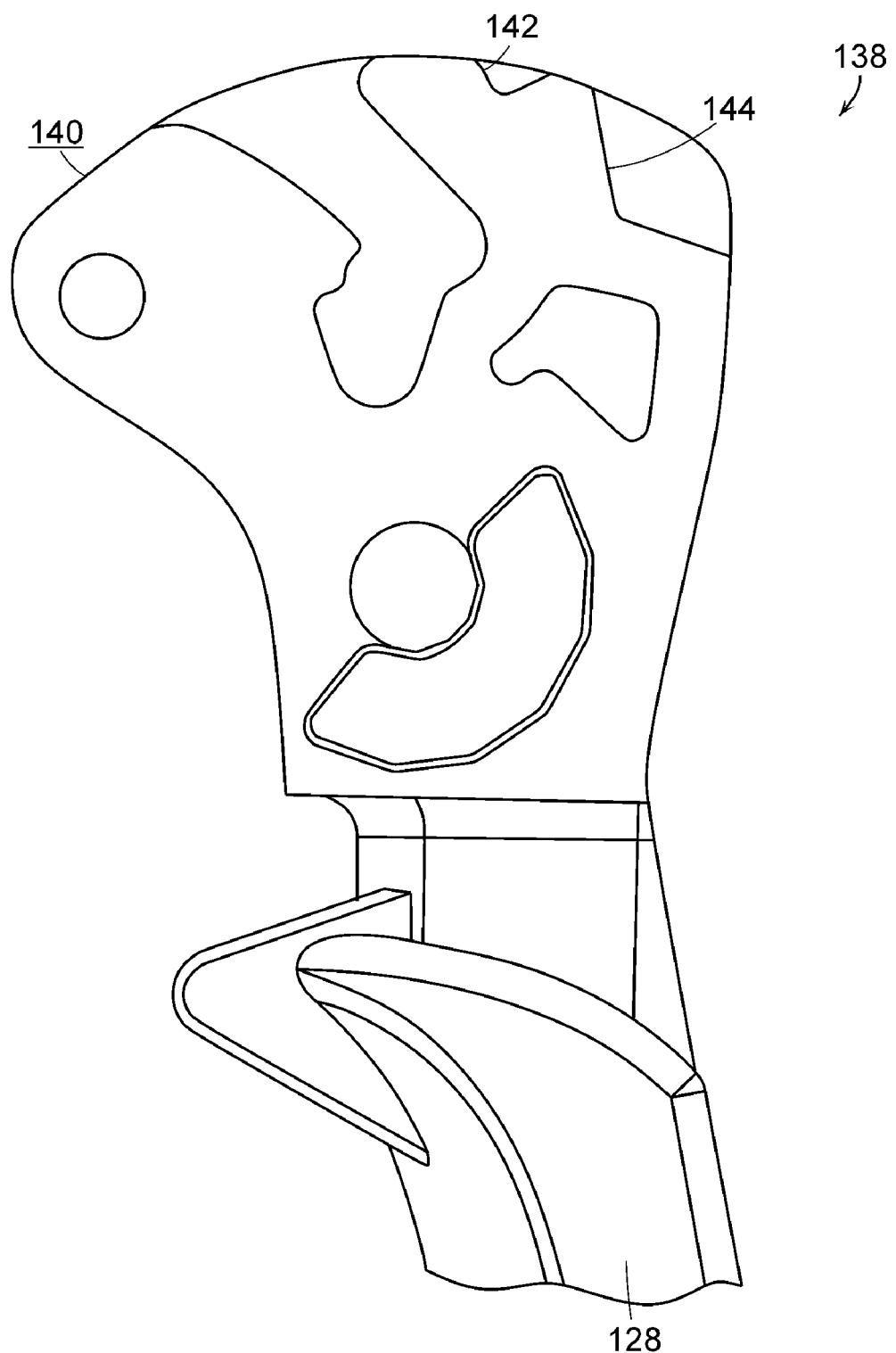
FIG. 16 is a partial elevational view of the closure trigger of FIG. 15.
Figure 17:
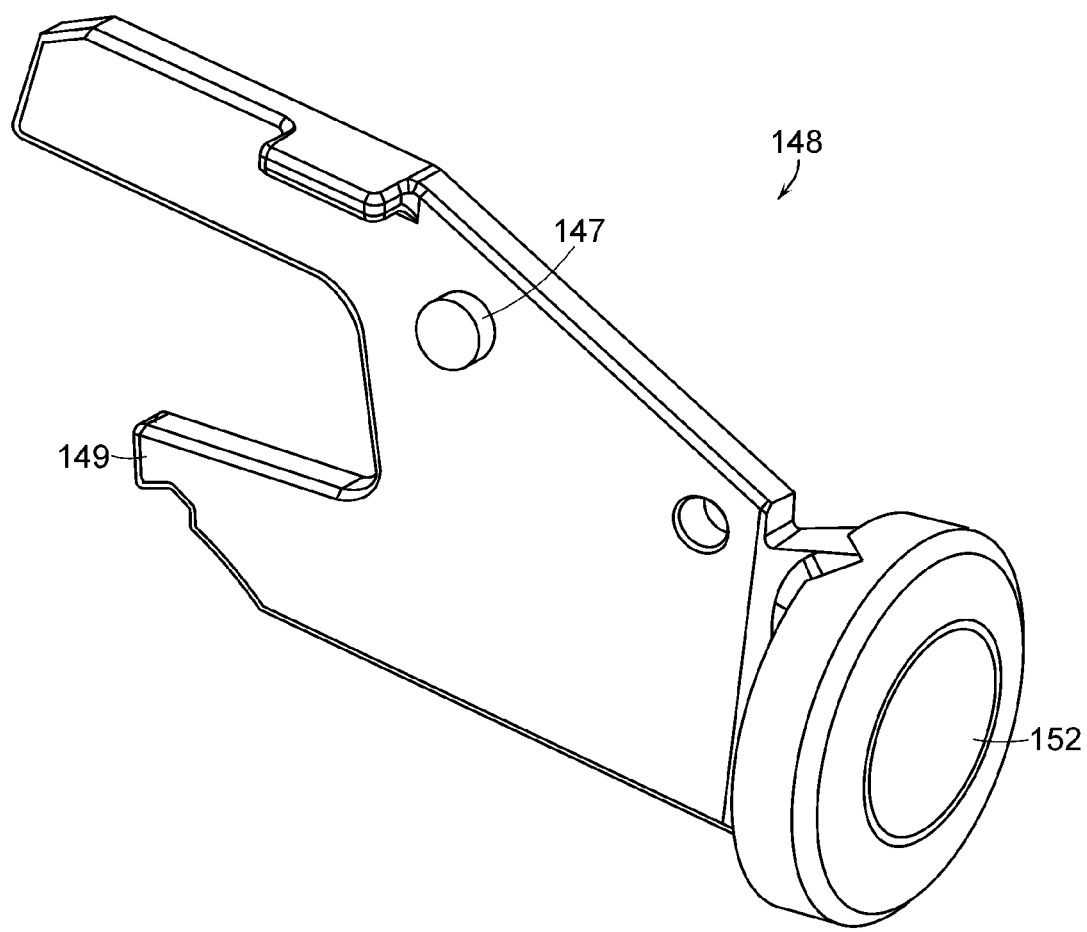
FIG. 17 is a perspective view of a trigger lock of the surgical instrument of FIG. 1.
Figure 18:
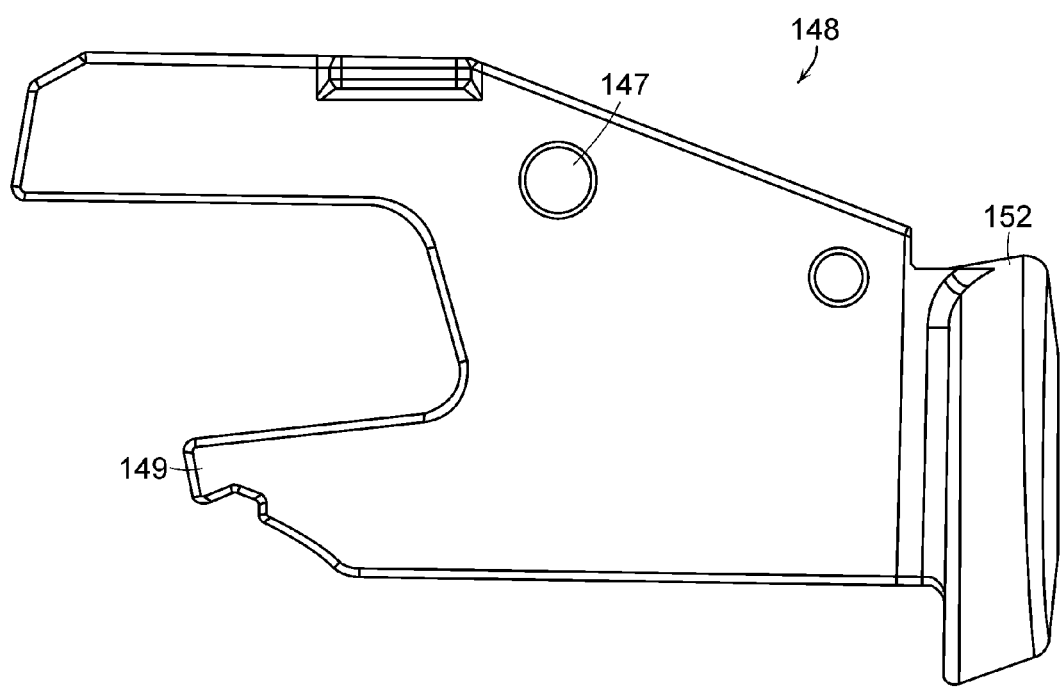
FIG. 18 is an elevational view of the trigger lock of FIG. 17.

In various embodiments, referring to FIGS. 10-13, the relative movement between actuator 122' and handle portion 102', as described above, can be limited in order to control the range through which lock member 120 can be displaced. More particularly, referring to FIGS. 10 and 11, the distal portion of actuator 122' can include projection 123 extending therefrom which can be received in cavity 125 where the displacement of actuator 122' can be limited by proximal wall 117 and distal wall 119 of cavity 125. In at least one embodiment, when trigger 128 is in its first position, as illustrated in FIGS. 10 and 11, actuator 122 can be moved from a distal position in which projection 123 can abut distal wall 119, as illustrated in FIG. 10, into a more proximal position in which projection 123 does not abut distal wall 119, as illustrated in FIG. 11. In this more distal position, as described above, lock member 120 can be disengaged from end effector 106 and end effector 106 can be rotated relative to shaft assembly 104. When trigger 128 is in its second position, referring to FIG. 12, driver 132 can limit the range of motion of actuator 122' such that projection 123 cannot be positioned against proximal wall 117. In at least one embodiment, however, actuator 122' can be moved proximally a sufficient distance to disengage lock member 120 from end effector 106. In these circumstances, a surgeon can reposition end effector 106 although anvil 112 may be partially closed onto the soft tissue, for example. When trigger 128 is in its third position, as illustrated in FIG. 13, driver 132 can force actuator 122' distally such that projection 132 abuts, or is positioned adjacent to, distal wall 119 and actuator 122' cannot be moved sufficiently to unlock articulation joint 114.

In various embodiments, a surgical instrument in accordance with the present invention can include a firing drive configured to advance a cutting member and/or staple driver within an end effector as described above. In at least one embodiment, referring to FIGS. 8, 9 and 19-25, the firing drive of surgical instrument 100 can include firing trigger 160, first firing link 162, second firing link 164, and firing member 166. In various embodiments, firing trigger 160 can be operably engaged with at least one of firing member 166 and firing links 162 and 164 in order to advance knife bar 168 within elongate shaft assembly 104. In at least one embodiment, knife bar 168 can be operably engaged with a cutting member (not illustrated) and a staple driver (not illustrated) in end effector 106 where the cutting member can be configured to incise tissue, for example, and the staple driver can be configured to deploy staples from staple cartridge 110. Cutting members and staple drivers are well disclosed in U.S. Pat. Nos. 6,905,057 and 7,044,352, which have been previously incorporated by reference into the present application, and, as a result, these devices are not described in greater detail herein. Other cutting members and staple drivers are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, which was filed on Sep. 29, 2006, and U.S. patent application Ser. No. 11/652,169, entitled SURGICAL STAPLING DEVICE WITH A CURVED CUTTING MEMBER, which was filed on Jan. 11, 2007, the entire disclosures of which are hereby incorporated by reference herein.

Figure 19:
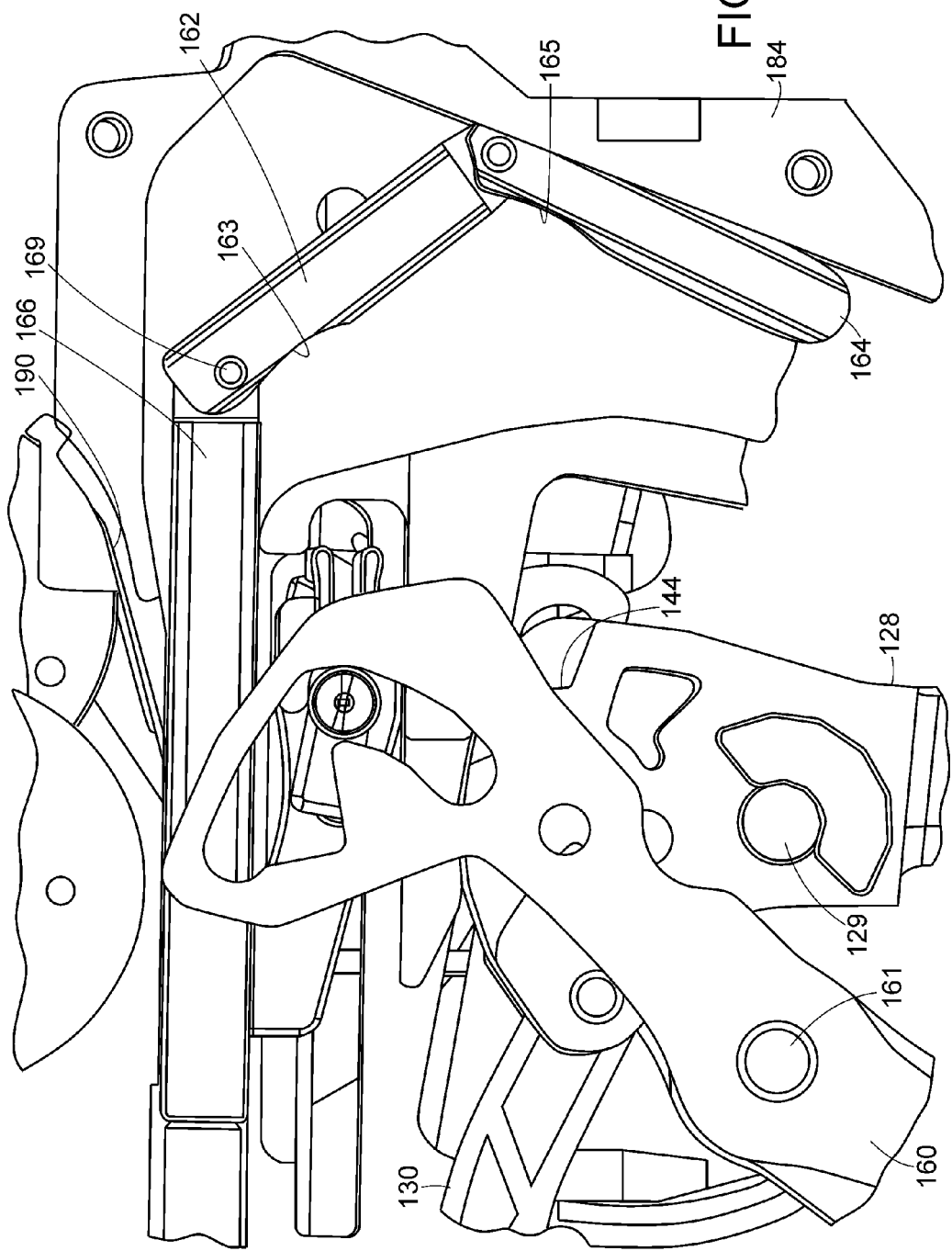
FIG. 19 is a detail view of a firing drive of the surgical instrument of FIG. 1 with some components of the surgical instrument removed.
Figure 20:
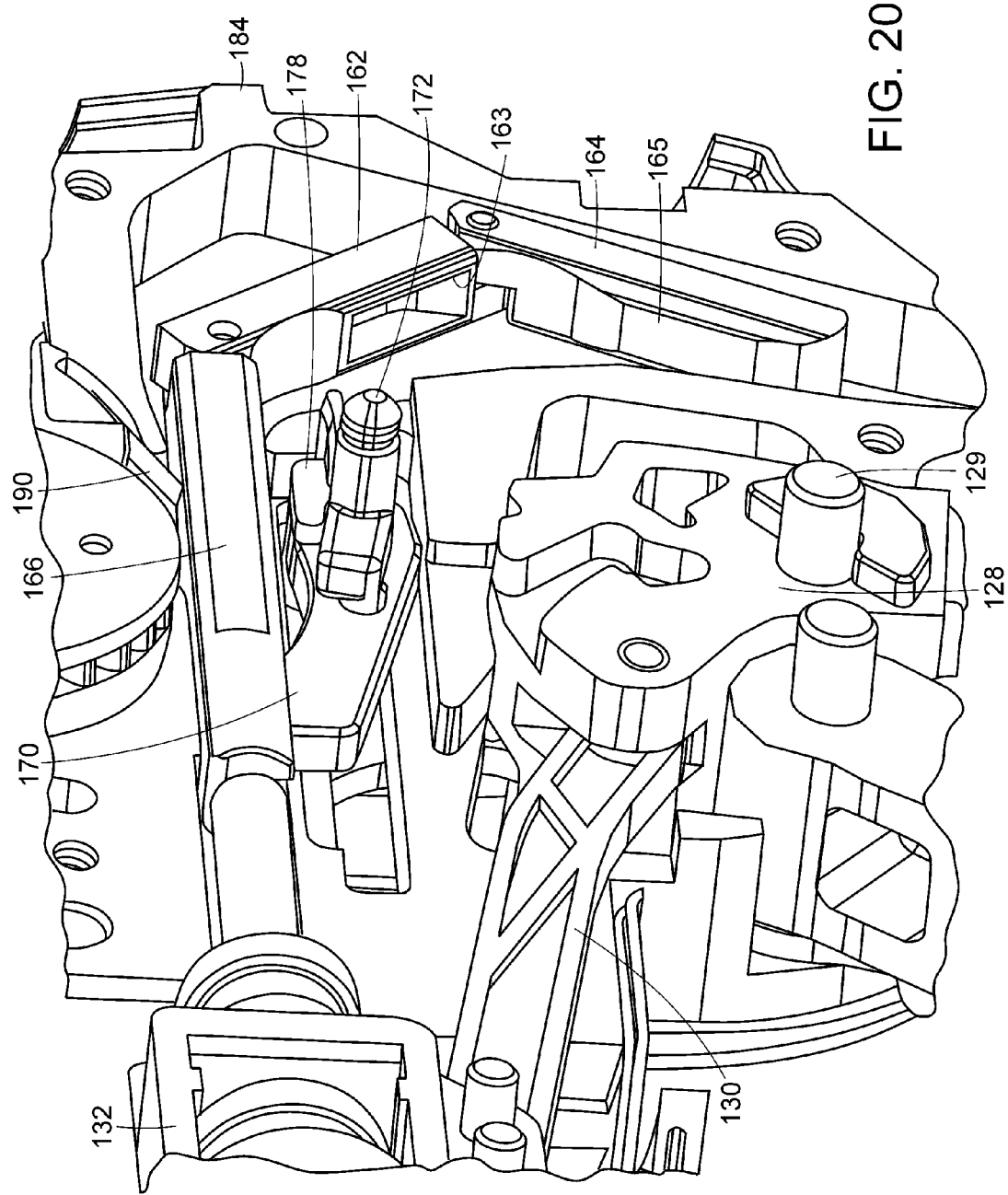
FIG. 20 is a perspective view of the firing drive of FIG. 19.
Figure 21:
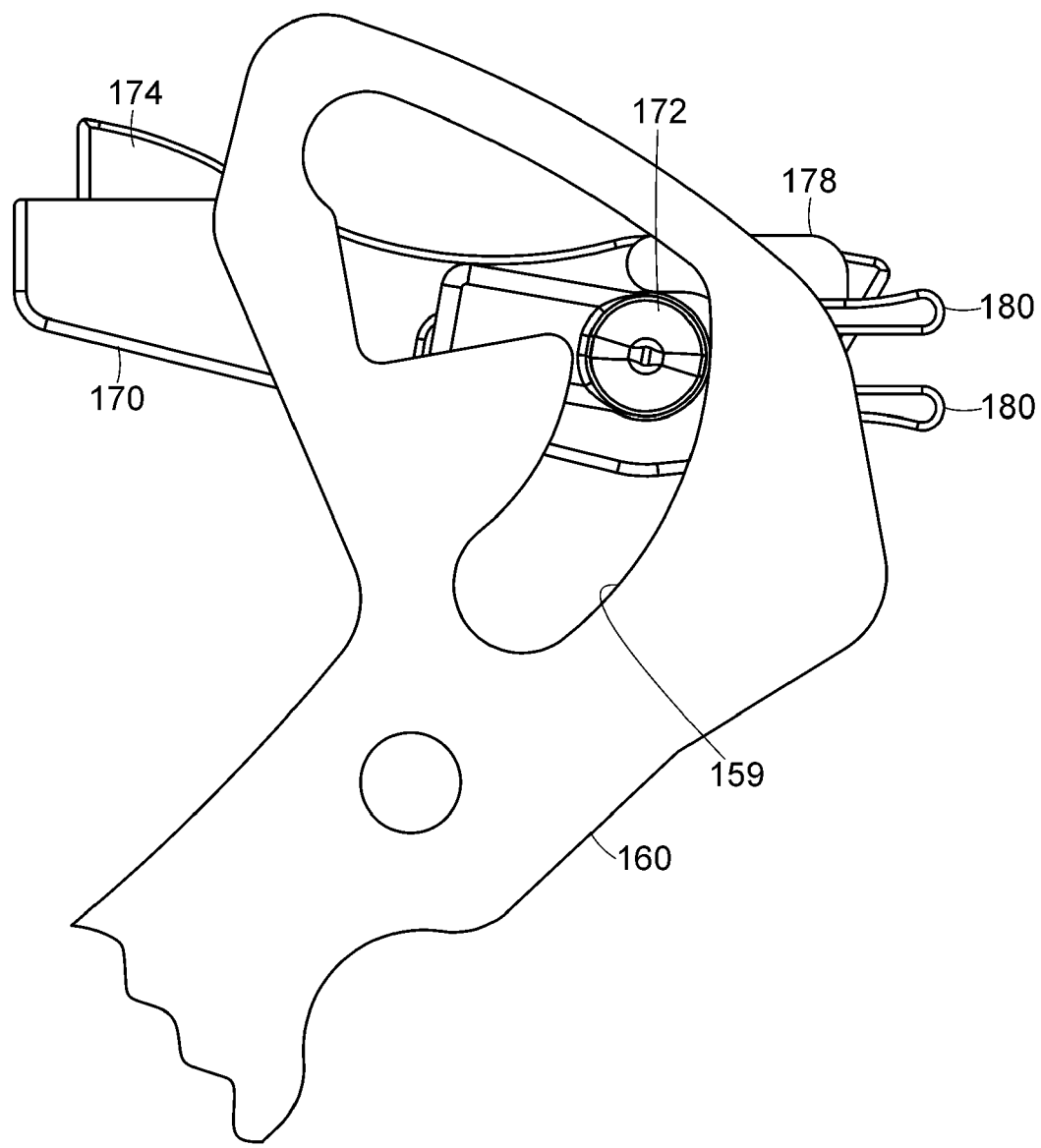
FIG. 21 is a partial detail view of a firing trigger, pawl, and tilter mechanism of the firing drive of FIG. 19.
Figure 26:
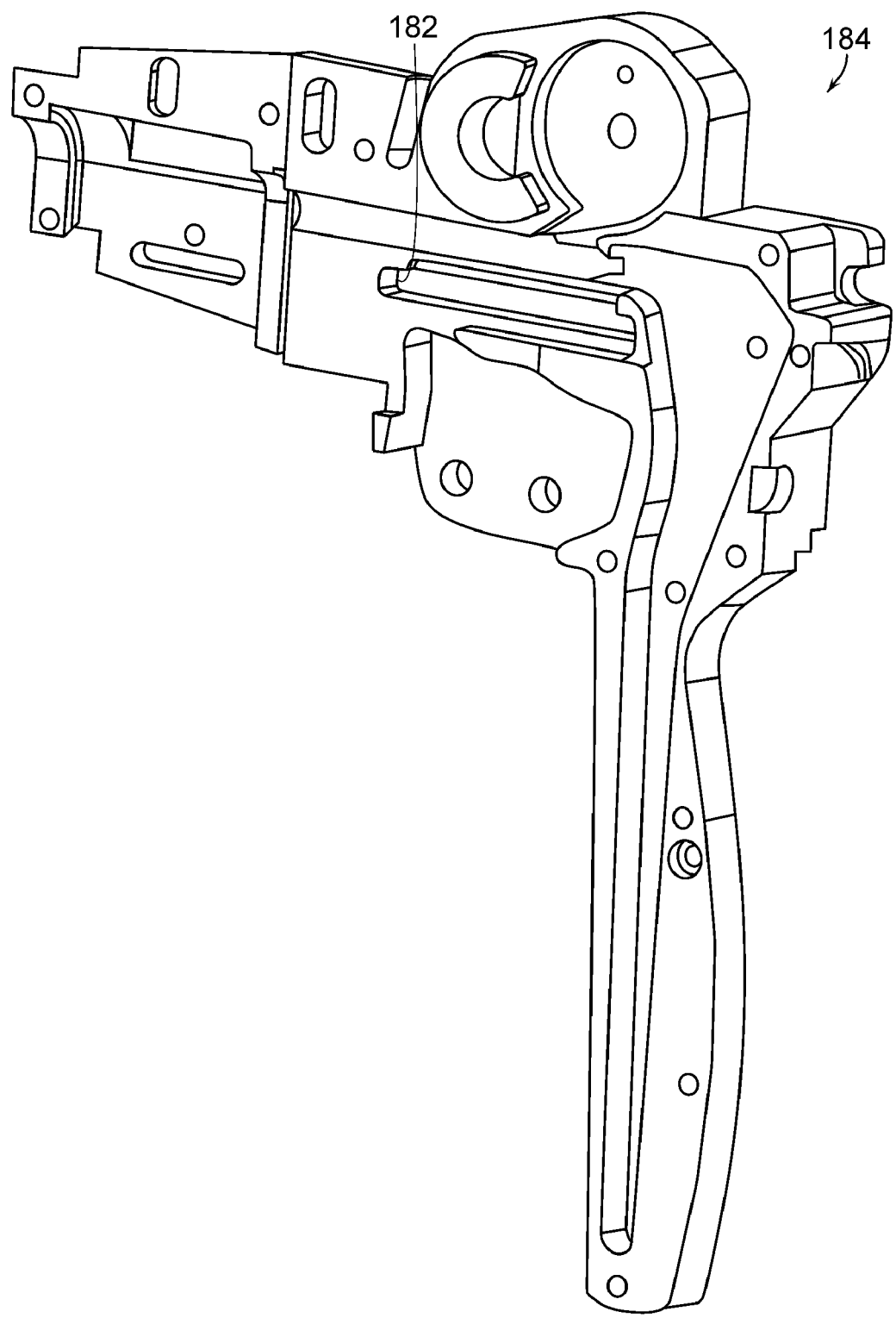
FIG. 26 is a perspective view of a frame of the surgical instrument of FIG. 1.

In various embodiments, referring primarily to FIGS. 19 and 20, firing trigger 160 can be pivotably connected to surgical instrument housing 103 (FIGS. 8 and 9) by pin 161. In use, in at least one embodiment, firing trigger 160 can be pivoted about pin 161 in order to advance firing member 166 and firing links 162 and 164 distally. In various embodiments, firing trigger 160 can include slots 159, where slots 159 can be configured to receive firing pin 172. In various embodiments, when firing trigger 160 is actuated, or rotated, from its position illustrated in FIG. 2 to a position adjacent handle grip 127, the side walls of slots 159 can be configured to engage and advance firing pin 172 distally. In at least one embodiment, referring to FIG. 23, the firing drive can further include pawl 170, where pawl 170 can include aperture 171. In various embodiments, aperture 171 can be configured to receive at least a portion of firing pin 172 such that, when firing pin 172 is advanced distally by trigger 160, firing pin 172 can advance pawl 170 distally as well. In various embodiments, referring to FIG. 24, pawl 170 can include tooth 174 and firing member 166 can include recess 167, where recess 167 can be configured to receive tooth 174. In use, when pawl 170 is advanced distally by firing pin 172 and tooth 174 is engaged with a side wall of recess 167, pawl 170 can advance firing member 166 distally as well. In various embodiments, pawl 170 can be advanced distally by firing pin 172 along a substantially linear path. In such embodiments, slots 159 can include arcuate profiles which can, in cooperation with firing pin 172, convert the rotational motion of firing trigger 160 into translational motion of pawl 170. In at least one embodiment, the force applied to pawl 170 can be substantially, if not entirely, directed in the distal direction. In such embodiments, as a result, the possibility of pawl 170 becoming bound or stuck against stapler frame 184 can be reduced.

In various embodiments, pawl 170 can be pivoted between a first position in which pawl 170 is operably disengaged from firing member 166 and a second position, referring to FIGS. 19 and 20, in which pawl 170 is operably engaged with firing member 166. Referring primarily to FIGS. 21-25, the firing drive can further include tilter mechanism 178 which can be configured to pivot pawl 170 between its first and second positions. In use, when firing trigger 160 is actuated, pawl 170 can be moved, at least initially, relative to tilter mechanism 178 such that at least a portion of pawl 170 can abut tilter mechanism 178 and pivot pawl 170 upwardly and into operative engagement with firing member 166. In at least one embodiment, pawl 170 can include, referring primarily to FIG. 23, groove 175 which can be configured to receive projection 179 (FIG. 25) extending from the center portion of tilter mechanism 178. In at least one embodiment, as pawl 170 is advanced distally, proximal wall 176 of groove 175 can contact a cam surface on projection 179 and, owing to the force applied to pawl 170 by pivot pin 172, pawl 170 can be pivoted, or rotated, upwardly such that tooth 174 can be positioned in recess 167 of firing member 166 as described above. After pawl 170 has been pivoted, pawl 170 can drag tilter mechanism 178 distally as pawl 170 is advanced toward end effector 106. More particularly, in at least one embodiment, tilter mechanism 178 can include deformable members 180 which can be received within slots 182 in stapler frame 184 such that the interaction between deformable members 180 and stapler frame 184 at least partially inhibits the movement of tilter mechanism 178 relative to stapler frame 184. Stated another way, owing to static friction forces between deformable members 180 and the side walls of slots 182, a force sufficient to overcome these friction forces must be applied to tilter mechanism 178 before tilter mechanism 178 can be 'dragged' relative to stapler frame 184.

After firing trigger 160 has been actuated and firing member 166 has been advanced, trigger 160 can be released and returned to its unactuated position illustrated in FIG. 2 and pawl 170 can be disengaged from firing member 166 and retracted to its starting position illustrated in FIG. 19. More particularly, in at least one embodiment, surgical instrument 100 can further include a trigger spring (not illustrated) operably engaged with trigger 160 and housing 103, for example, where the trigger spring can be configured to rotate trigger 160 about pin 161 and drive firing pin 172 proximally after pawl 170 has been disengaged from firing member 166. In various embodiments, pawl 170 can be disengaged from firing member 166 when it is pivoted from its second position, as illustrated in FIG. 24, into its first position, as described above, by tilter mechanism 178. In such embodiments, pawl 170 can be moved, at least initially, relative to tilter mechanism 178 such that distal wall 177 of groove 175 can contact a second cam surface on projection 179 and can, owing to a force applied to firing pin 172 by trigger 160 or return spring 186, rotate pawl 170 downwardly such that tooth 174 of pawl 170 can be disengaged from recess 167 in firing member 166. Thereafter, trigger 160 and/or return spring 186 can pull, or retract, pawl 170 relative to firing member 166. In various embodiments, similar to the above, pawl 170 can be configured to drag tilter mechanism 178 proximally within slot 182. As a result of the above, pawl 170 does not need to be biased into its first or second positions. In various circumstances, pawl 170 can be rotated freely between its first and second positions without having to overcome a force applied thereto by a biasing spring. In effect, in various embodiments, the force to move pawl 170 between its first and second positions need only overcome the gravitational weight of pawl 170 and any frictional forces between pawl 170 and the surrounding components of the surgical instrument.

Once pawl 170 has been returned to its original position, in at least one embodiment, tooth 174 of pawl 170 may no longer be aligned with recess 167 in firing member 166. On the contrary, referring generally to FIGS. 19 and 20, tooth 174 of pawl 170 can be aligned with recess 163 in first firing link 162. More particularly, first firing link 162 can be pivotably connected to firing member 166 such that, when firing member 166 is advanced distally, as described above, firing member 166 can pull first firing link 162 into the position that firing member 166 previously occupied. As a result, upon a second actuation firing trigger 160, pawl 170 can be pivoted from its first position into its second position such that tooth 174 is operably engaged with recess 163 and pawl 170 can advance firing link 162 distally. In at least one embodiment, firing link 162 can push firing member 166 and knife bar 168 distally and, correspondingly, advance the cutting member and the staple driver distally within end effector 106. Thereafter, pawl 170 can once again be pivoted from its second position to its first position and can be retracted relative to first firing link 162. Once pawl 170 is returned to its original position for the second time, tooth 174 of pawl 170 may no longer be aligned with recess 163 of first firing link 162. On the contrary, similar to the above, tooth 174 can be aligned with recess 165 in second firing link 164 and the process described above can be repeated.

Although not illustrated, a surgical instrument in accordance with the present invention can include more than two, or less than two, firing links in order to advance the cutting member and staple driver to their desired positions within end effector 106. In various embodiments, although not illustrated, firing member 166 can include more than one recess 167 such that pawl 170 can directly advance firing member 166 toward end effector 106 more than once. In at least one such embodiment, pawl 170 can be retracted after advancing firing member 166 distally, as described above, such that, when pawl 170 is once again tilted upwardly, pawl 170 can engage another recess 167 in firing member 166 and advance firing member 166 toward end effector 106 once again. As a result, in at least one embodiment, firing links 162 and 164 may not be required.

Figure 27:
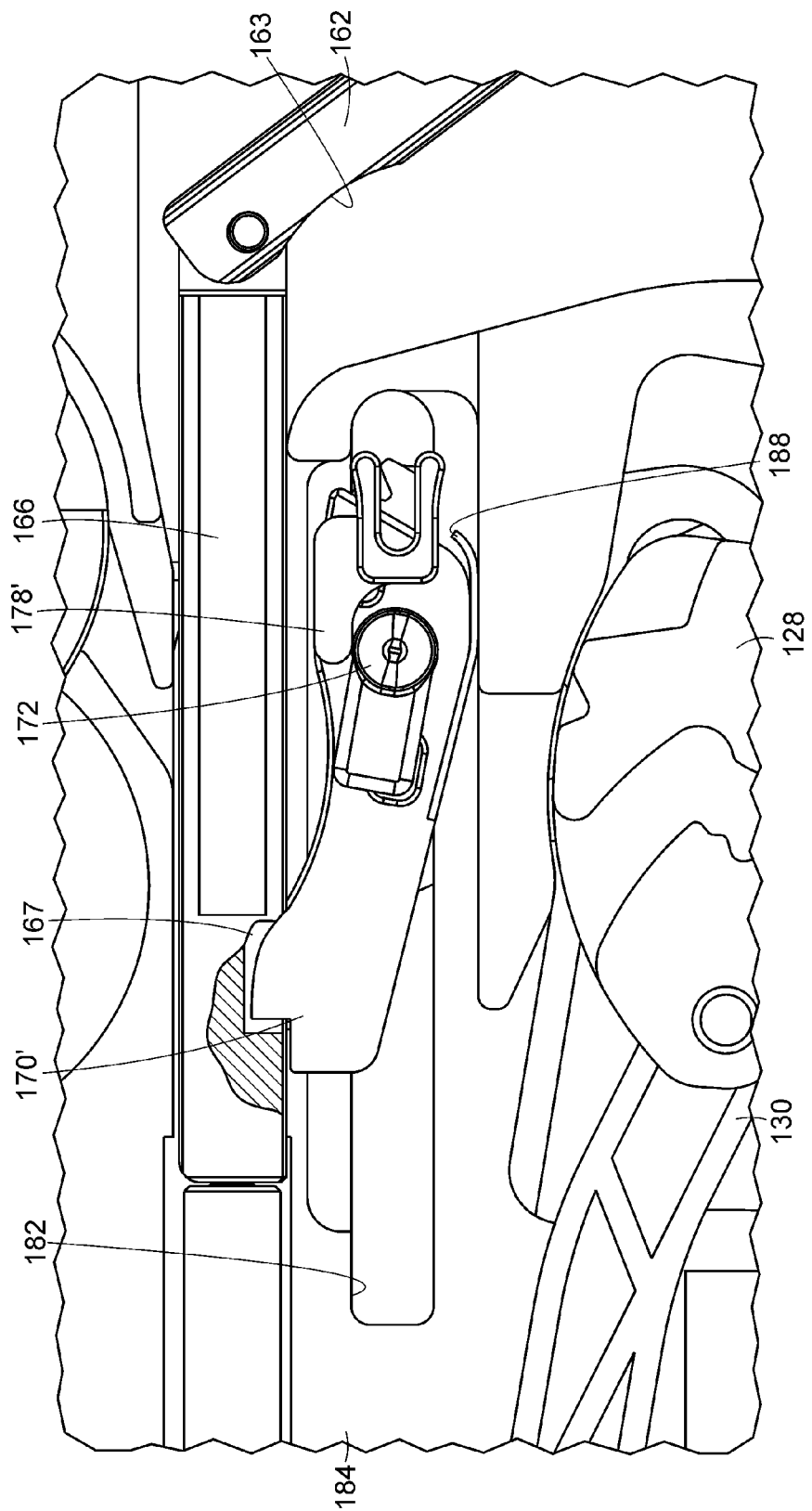
FIG. 27 is a detail view of a firing drive of a surgical instrument in accordance with an alternative embodiment of the present invention with some components of the surgical instrument removed.
Figure 28:
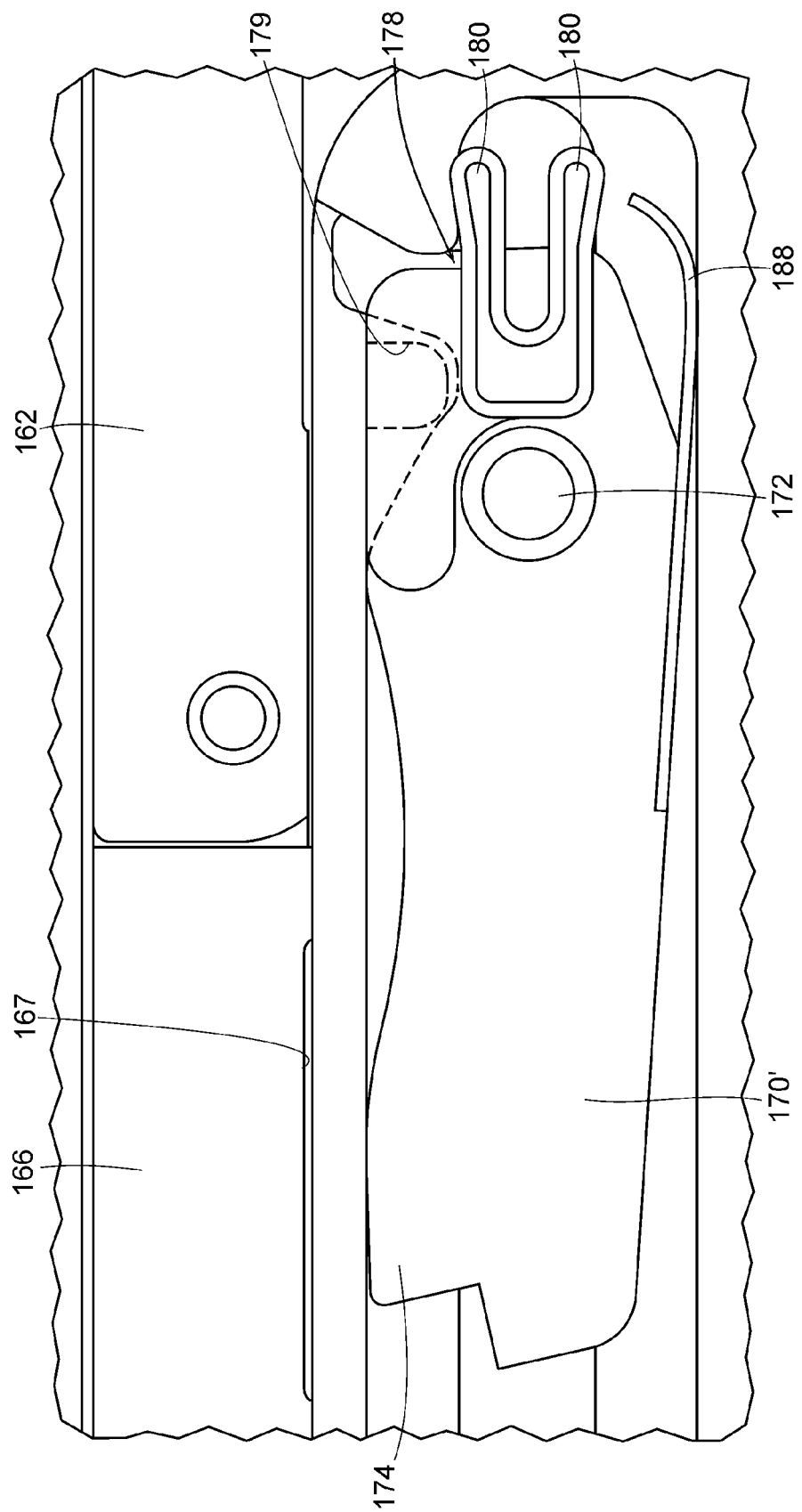
FIG. 28 is a detail view of the firing drive of FIG. 27 illustrating a pawl of the firing drive disengaged from a firing link.

In various embodiments, a surgical instrument can include one or more spring members configured to move pawl 170 into at least one of its first and second positions. In at least one embodiment, referring to FIGS. 27 and 28, the firing drive can include pawl 170', firing pin 172, and tilter mechanism 178' where, similar to the above, tilter mechanism 178' can be configured to pivot pawl 170' upwardly when pawl 170' is advanced distally. The firing drive can further include pivot spring 188 which can be operably connected to pawl 170' such that, when pawl 170' is pivoted upwardly into its second position as illustrated in FIG. 27, pawl 170' can flex, or resiliently bend, pivot spring 188. After pawl 170' has been advanced, pawl 170' can be pivoted downwardly into its first position by pivot spring 188 as illustrated in FIG. 28. More particularly, owing to potential energy stored in pivot spring 188 when it is flexed, spring 188 can move pawl 170' downwardly once pawl 170' is no longer held in its second position by tilter mechanism 178' and firing pin 172. Thereafter, as described above, pawl 170' can be retracted relative to firing member 166 and/or firing links 162 and 164. In various embodiments, tilter mechanism 178' may not include a second cam surface for pivoting pawl 170 into its first position. In such embodiments, pawl 170' can be retracted by a force applied to firing pin 172 as described above. In various alternative embodiments, although not illustrated, tilter mechanism 178' and pawl 170' can also include co-operating features for pivoting pawl 170' downwardly into its first position.

In various embodiments, referring to FIGS. 19 and 20, surgical instrument 100 can further include band 190 which can be configured to move firing member 166 and firing links 162 and 164 relative to end effector 106. In at least one embodiment, a first end of band 190 can be connected to firing member 166, for example, such that, when firing member 166 is advanced distally, band 190 can be pulled distally as well. In various alternative embodiments, band 190 can be connected to first firing link 162 and/or second firing link 164. In at least one embodiment, band 190 can be positioned around at least a portion of reel, or spool, 192 such that when band 190 is pulled by firing member 166, band 190 can be deployed, or unwound, from reel 192. In at least one embodiment, a second end of band 190 can be connected to reel 192 such that band 190 cannot be readily disengaged from reel 192 under the normal operating conditions of surgical instrument 100. In either event, when band 190 is pulled by firing member 166, reel 192 can be rotated in one of a clockwise or counter-clockwise direction, depending on the manner in which band 190 is positioned around reel 192. In order to retract firing member 166, reel 192 can be rotated in an opposite direction to move firing member 166, and firing links 162 and 164, proximally and wind band 190 around reel 192.

In various embodiments, band 190 can be wound around reel 192 such that band 190 is wrapped around a substantially cylindrical surface on reel 192. In at least one embodiment, the distance between an axis of rotation of reel 192 and the cylindrical surface can be substantially equidistant around the perimeter of reel 192. In these embodiments, the mechanical advantage of reel 192 can remain substantially constant as band 190 is pulled proximally as described above and the capacity for reel 192 to apply a pulling force to band 190 can remain substantially the same. In alternative embodiments, however, reel 192 can be configured to provide a variable mechanical advantage. In at least one embodiment, reel 192 can include a non-cylindrical surface on which band 190 can be wrapped such that the distance between the axis of rotation of reel 192 and the non-cylindrical surface is not equidistant around the perimeter of reel 192. In these embodiments, as a result, the capacity for reel 192 to apply a pulling force to band 190 can change as band 190 is wound around reel 192.

In at least one embodiment, reel 192 can act as a cam and can include a shape which can be optimized to provide additional force to band 190 when it is initially retracted, i.e., when the force to retract the cutting member, for example, can be at its highest.

Figure 29:
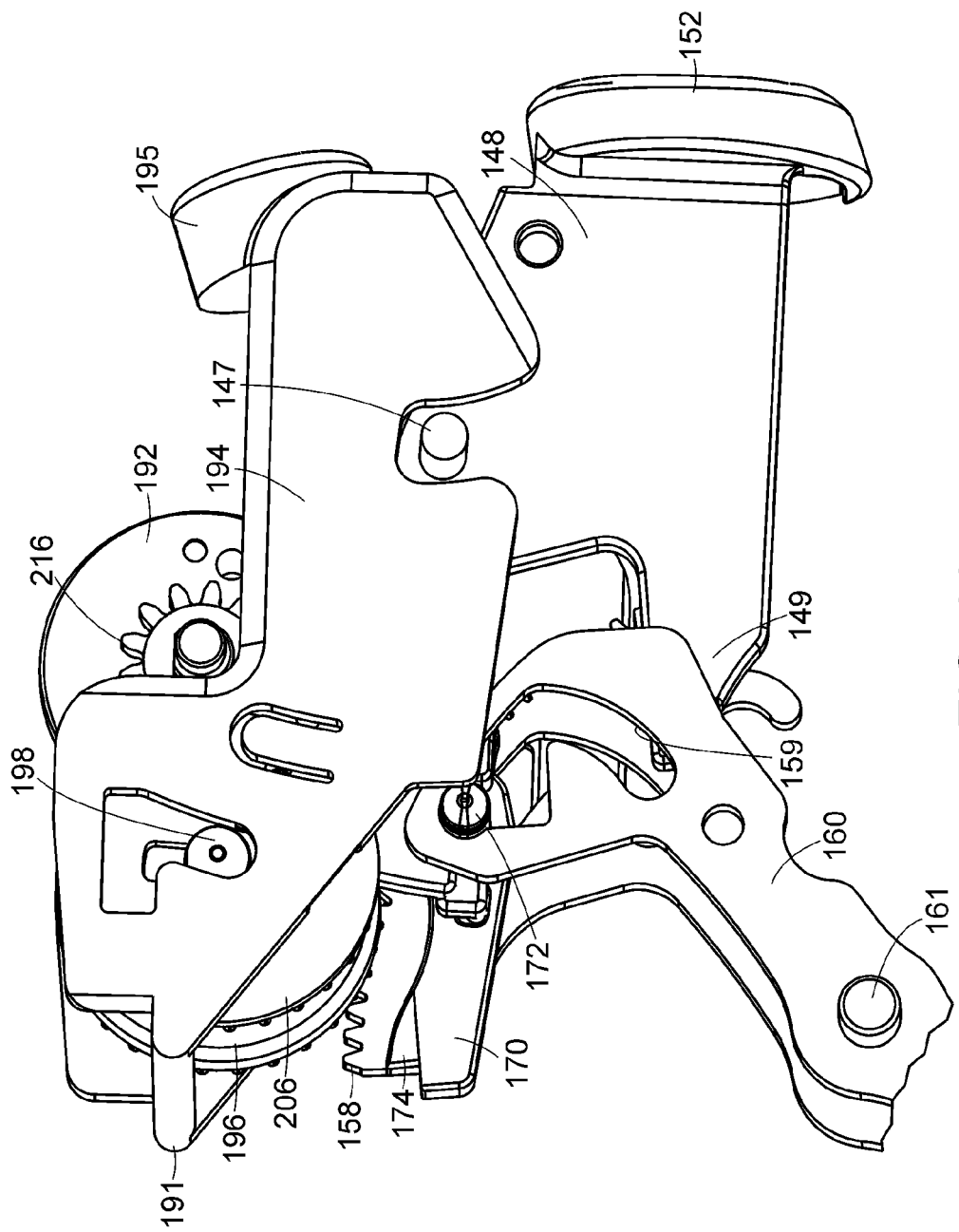
FIG. 29 is a perspective view of a return mechanism of the surgical instrument of claim 1 illustrating the firing trigger in an unactuated position with some components of the surgical instrument removed.

In various embodiments, referring to FIGS. 29-42, firing trigger 160 can be selectively engaged with a return mechanism of surgical instrument 100. In at least one embodiment, when firing trigger 160 is operably engaged with firing member 166 via pawl 170, as described above, an actuation of firing trigger 160 can advance firing member 166 distally and, when firing trigger 160 is operably engaged with firing member 166 via band 190, an actuation of firing trigger 160 can retract firing member 166 proximally. In various embodiments, the return mechanism can be manually actuated to disengage firing trigger 160 from firing member 166 and to operably engage firing trigger 160 with reel 192. In at least one embodiment, the return mechanism can include return carriage 194 which can be pivotably mounted in surgical instrument housing 103 such that return carriage 194 can be pivoted between a first, or unactuated, position as illustrated in FIG. 29 and a second, or actuated, position as illustrated in FIG. 32. In at least one such embodiment, return carriage 194 can include push button portion 195 which, when a force is applied thereto, can be configured to move return carriage 194 from its unactuated position to its actuated position.

Figure 30:
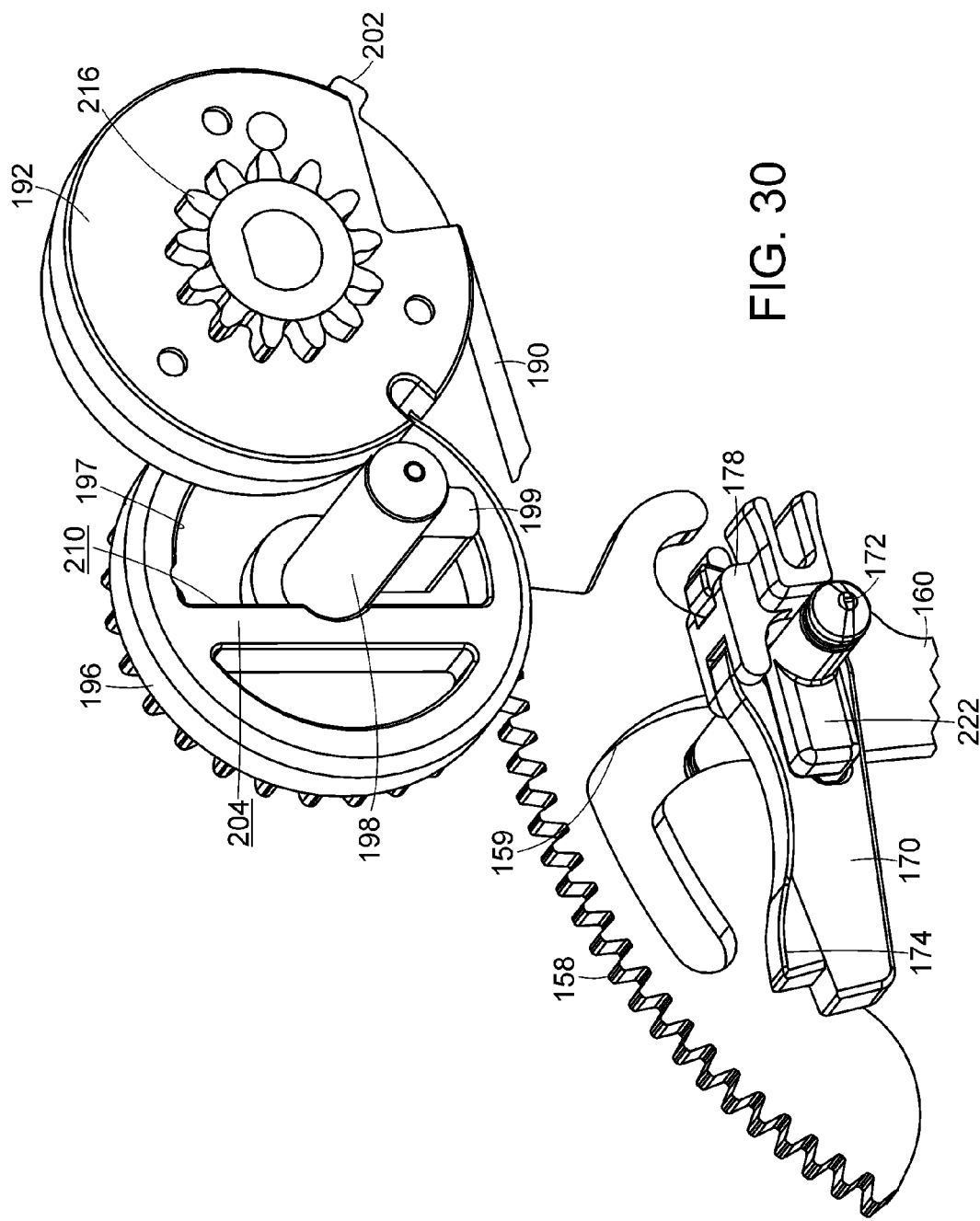
FIG. 30 is a partial perspective view of the return mechanism of FIG. 29 illustrating the firing trigger in an actuated position with some components of the return mechanism removed.
Figure 31:
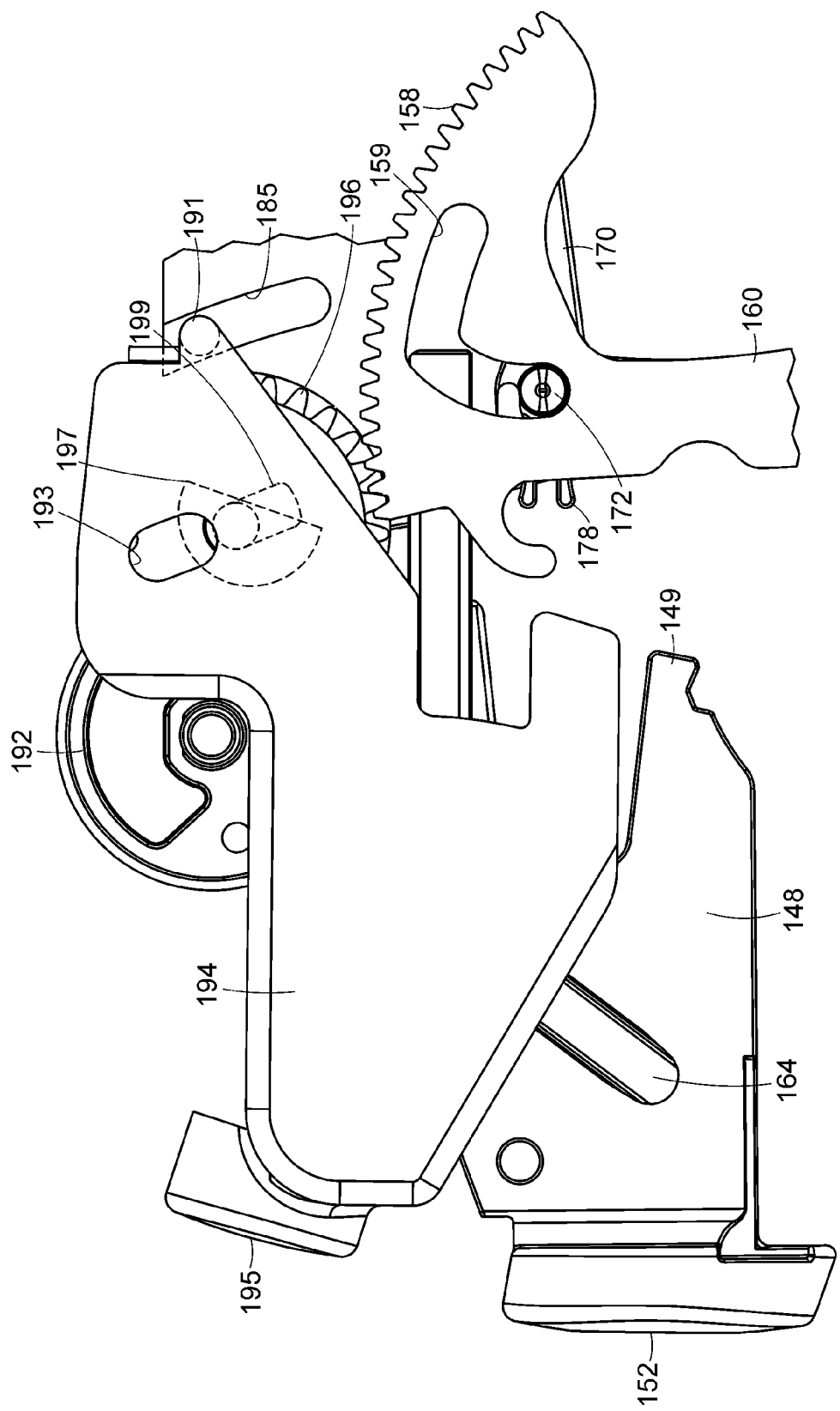
FIG. 31 is an elevational view of the return mechanism of FIG. 29 arranged in the configuration illustrated in FIG. 30.
Figure 32:
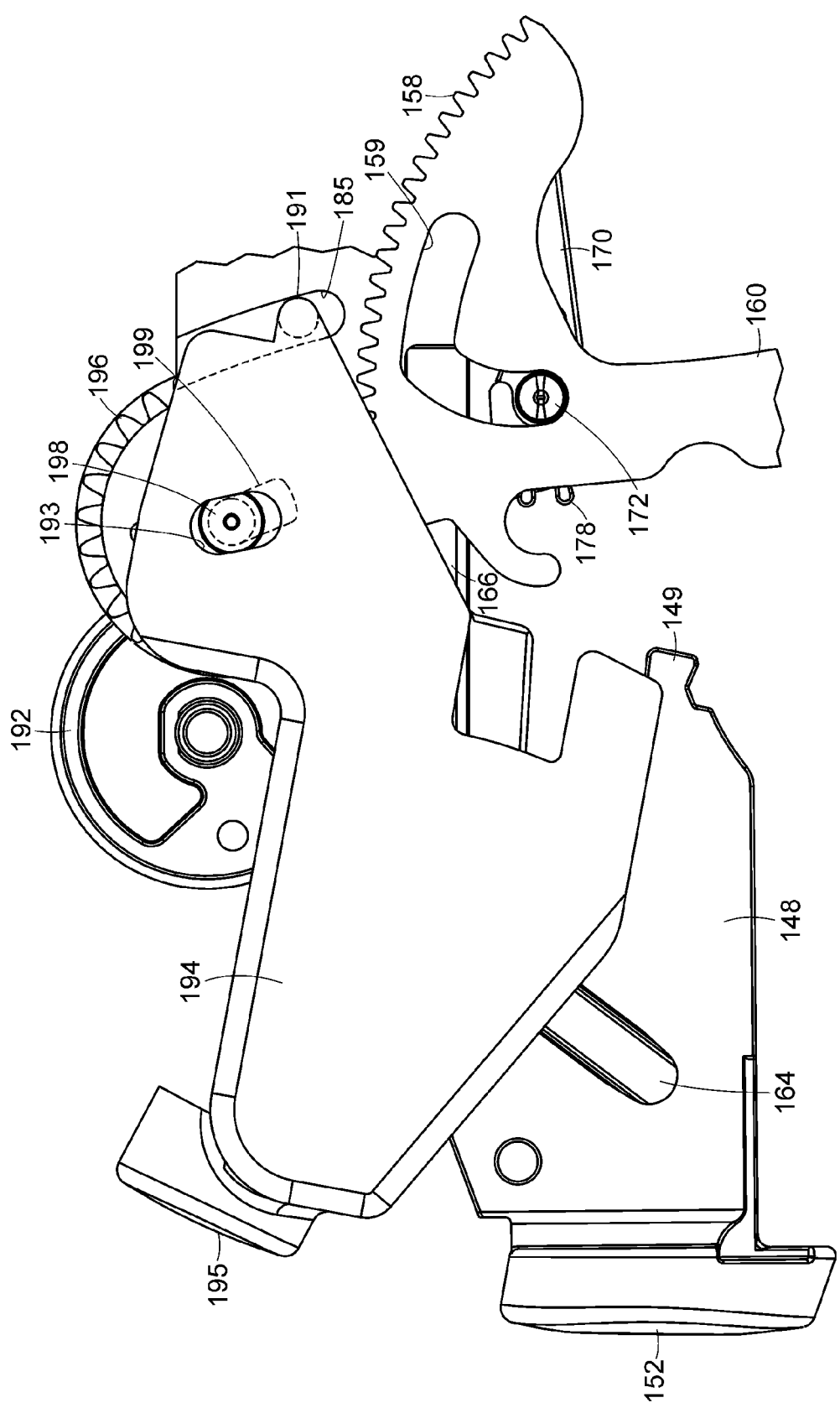
FIG. 32 is an elevational view of the return mechanism of FIG. 29 illustrating a return carriage of the return mechanism in an actuated position.
Figure 33:
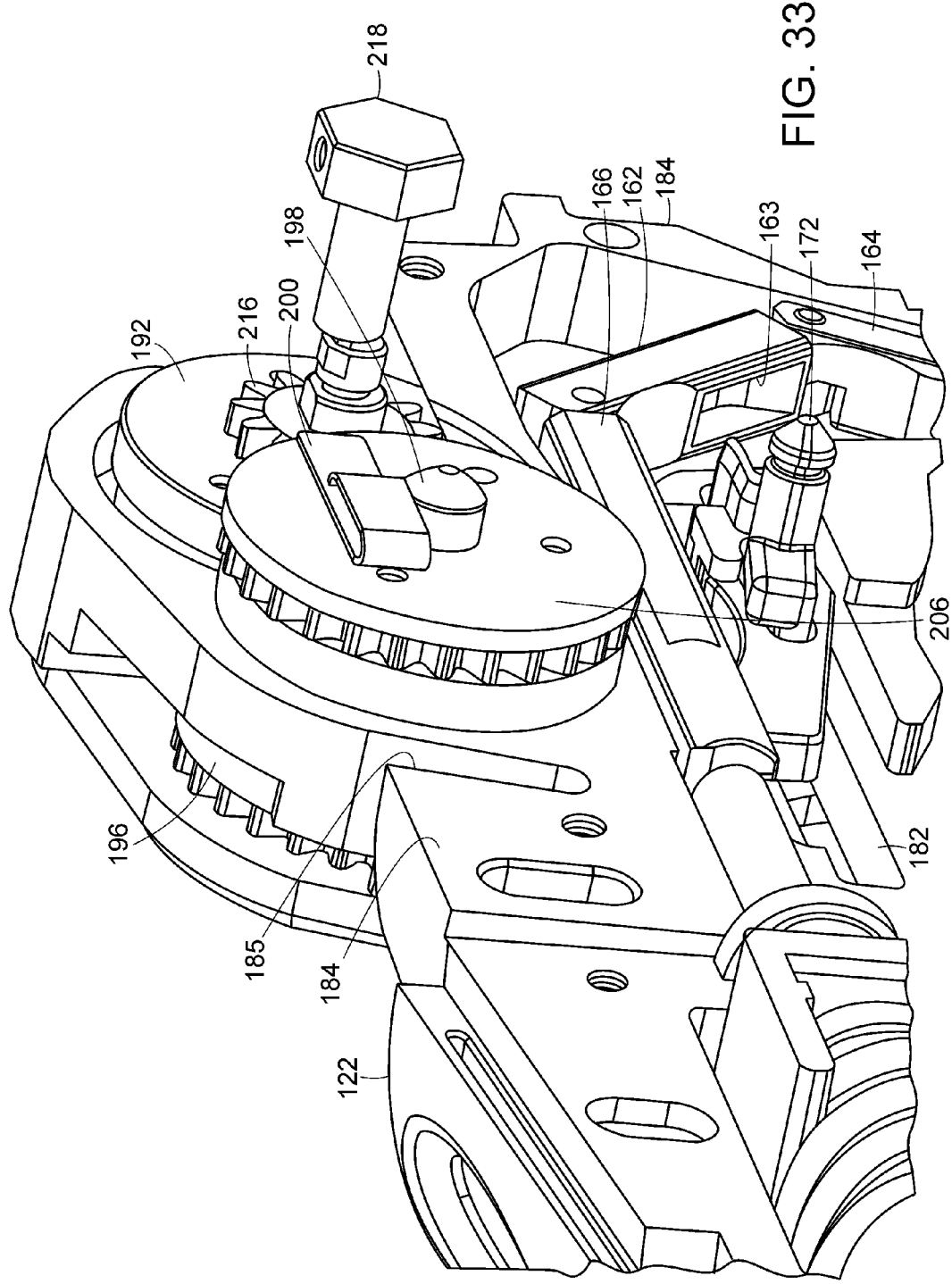
FIG. 33 is a partial perspective view of the return mechanism of FIG. 29 with some components of the return mechanism removed.
Figure 34:
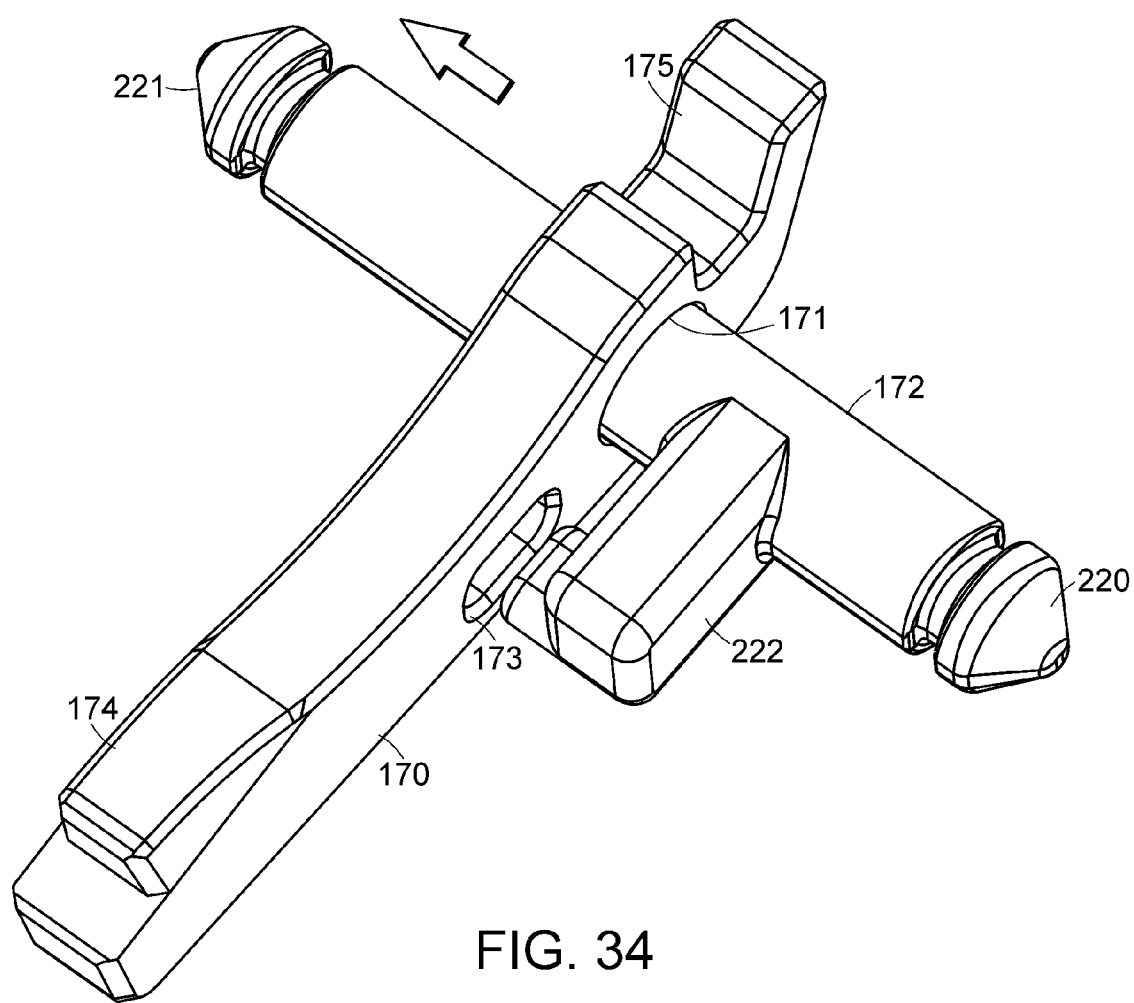
FIG. 34 is a perspective view of the pawl and firing pin of the firing drive of FIG. 19.
Figure 35:
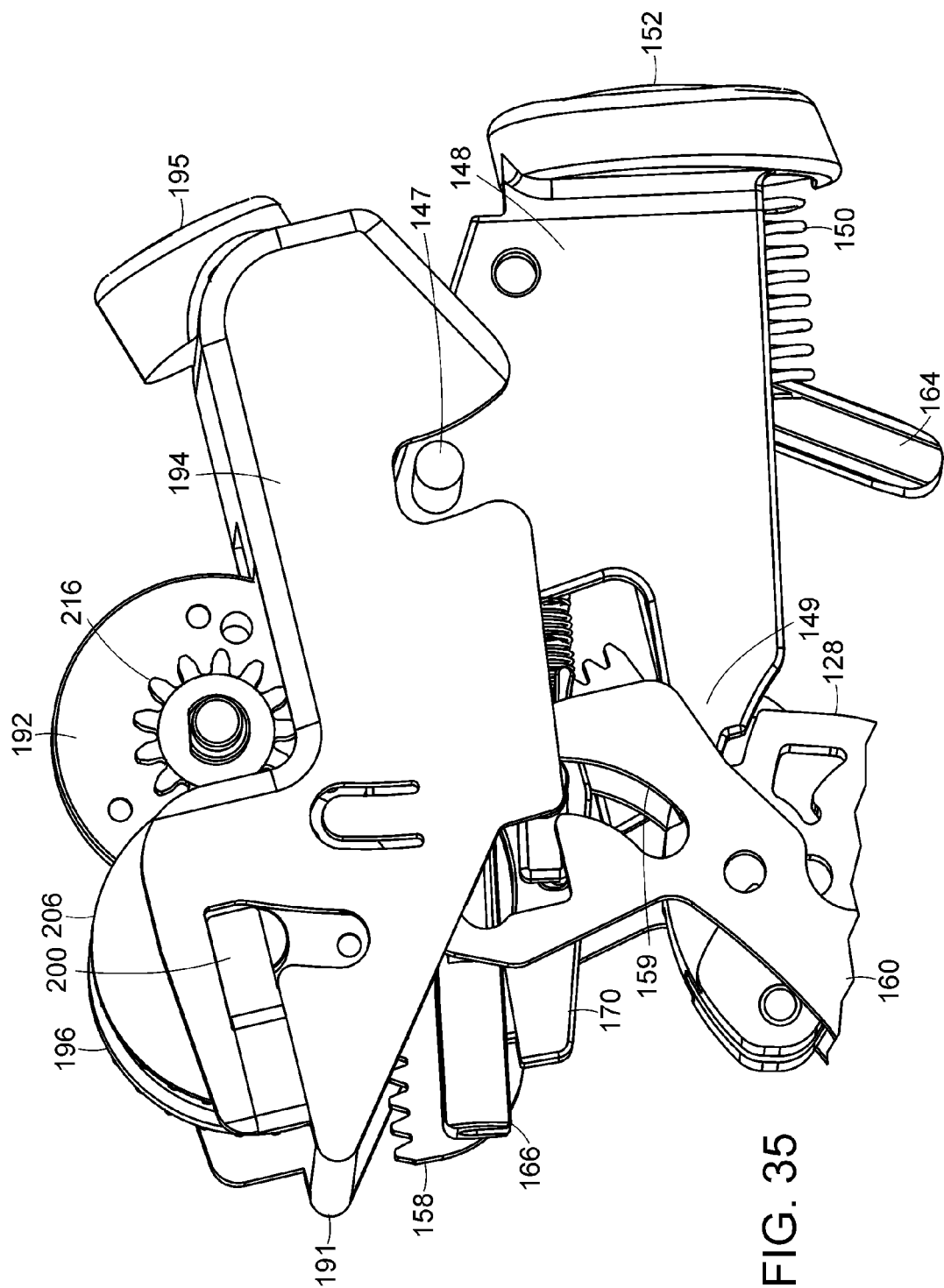
FIG. 35 is a perspective view of the return mechanism of FIG. 29 illustrating the return carriage in an actuated position and the firing trigger returned to its unactuated position.

When return carriage 194 is positioned in its unactuated position illustrated in FIGS. 29-31, firing trigger 160 can be configured to advance firing member 166 as described above and gear portion 158 of trigger 160 can be operatively engaged with trigger gear 196. In various embodiments, gear portion 158 and trigger gear 196 can be operably engaged such that a rotation of trigger 160 about pin 161 can drive trigger gear 196 about an axis defined by return pin 198. In at least one embodiment, when return carriage 194 is in its unactuated position, trigger gear 196 can be configured to rotate freely about return pin 198 such that the rotation of trigger gear 196 is not transmitted, or at least not substantially transmitted, to return pin 198. More particularly, referring to FIG. 30, key 199 of return pin 198 can be biased out of engagement with trigger gear 196 such that the rotation of trigger gear 196 is not transmitted to key gear 206 and reel 192. As a result, an actuation of trigger gear 160 does not rotate, or at least substantially rotate, reel 192 when return carriage 194 is in its unactuated position.

After the cutting member and the staple driver have been advanced within end effector 106, return carriage 194 can be moved into its actuated position. In various embodiments, referring to FIG. 30, reel 192 can include cam member 202 extending therefrom which can contact return carriage 194 and rotate return carriage 194 downwardly. In at least one embodiment, cam member 202 can contact return carriage 194 during the final actuation of trigger 160 which advances the cutting member and staple driver within end effector 106. In at least one such embodiment, cam member 202 can contact return carriage 194 after the third actuation of firing trigger 160. In various embodiments, referring to FIGS. 32-35, when gear carriage 194 is moved into its actuated position, return carriage 194 can be configured to operably engage trigger gear 196 with reel 192. In at least one embodiment, referring to FIGS. 33 and 35, return carriage 194 can include biasing spring 200 where, when return carriage 194 is in its unactuated position, spring 200 can be located in the position illustrated in FIG. 33 and, when return carriage 194 is moved into its actuated position illustrated in FIG. 35, spring 200 can contact return pin 198 and bias return pin 198 toward trigger gear 196. In at least one embodiment, referring to FIG. 31, trigger gear 196 can include D-shaped cavity 197 therein which can, under certain circumstances explained below, receive key 199 extending from return pin 198 and operably engage trigger gear 196 with key gear 206 and reel 192. In various embodiments, the movement of return carriage 194 into its actuated position can be accompanied by an audio and/or tactile feedback to inform the surgeon that the return mechanism of the surgical instrument has been engaged with trigger 160.

Figure 36:
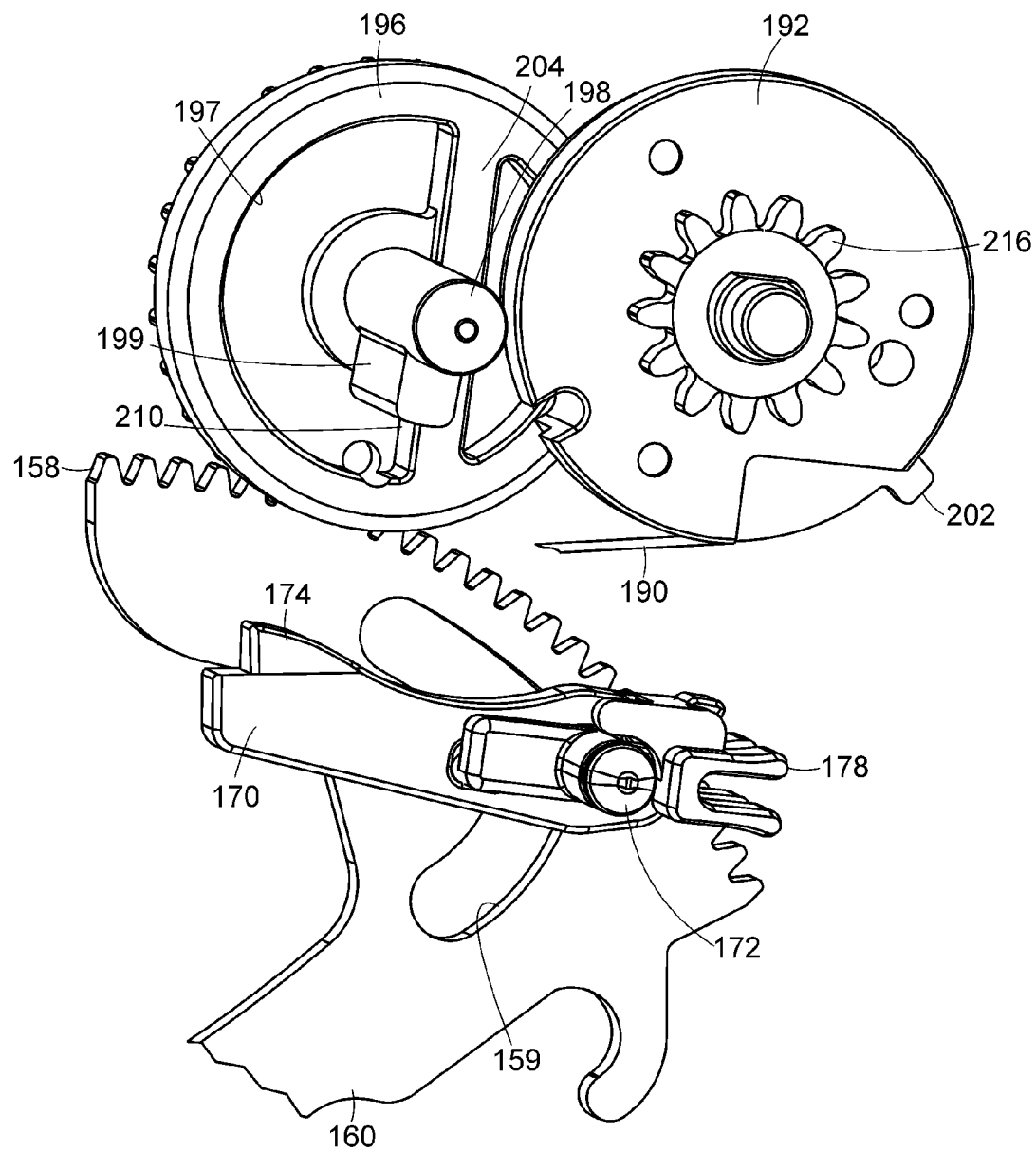
FIG. 36 is a partial perspective view of the return mechanism of FIG. 29 arranged in the configuration illustrated in FIG. 35 illustrating a return pin of the return mechanism operably engaged with the firing trigger.
Figure 37:
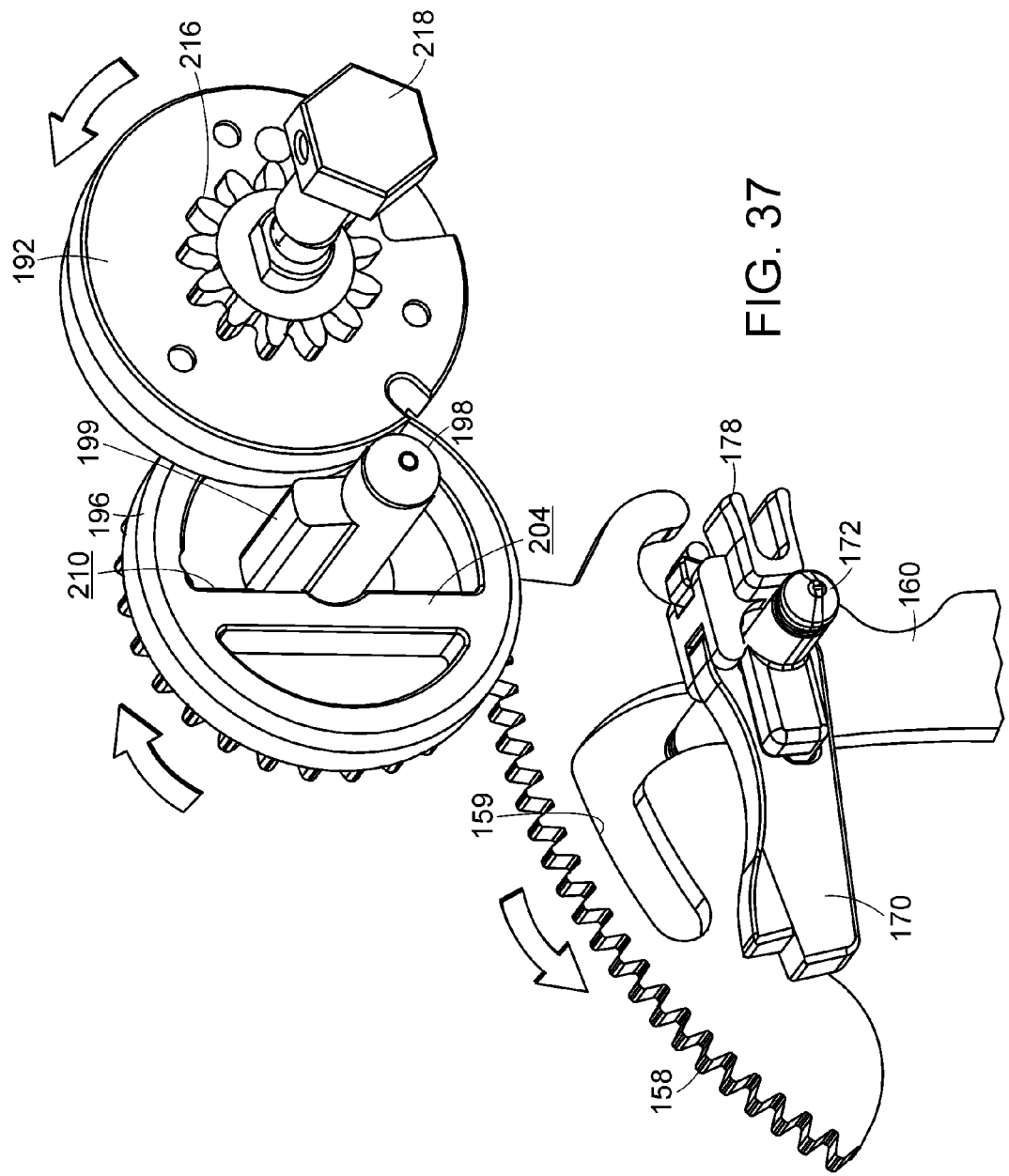
FIG. 37 is a partial perspective view of the return mechanism of FIG. 29 illustrating the firing trigger in an actuated position after rotating the return pin.
Figure 39:
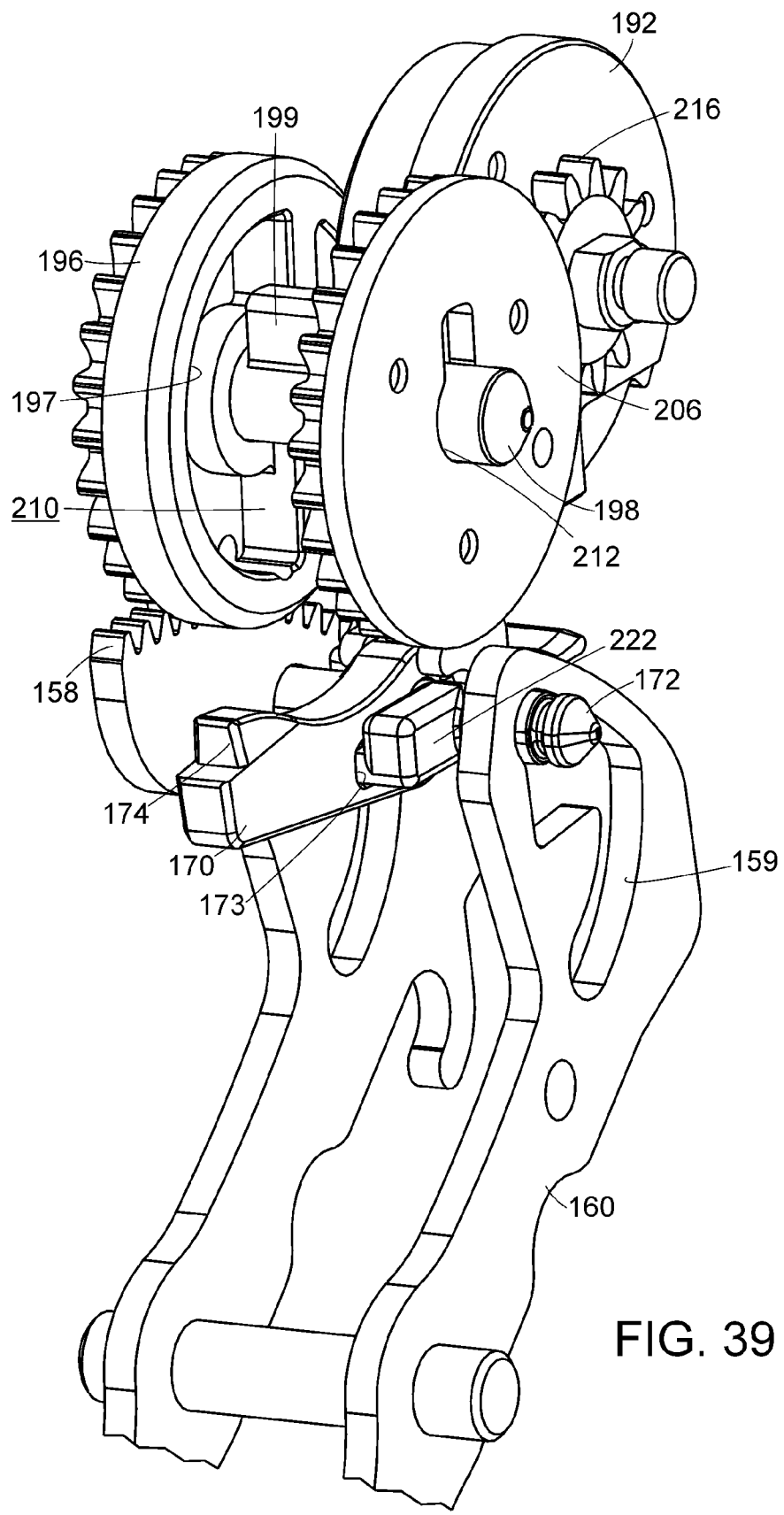
FIG. 39 is a partial perspective view of the return mechanism of FIG. 29 illustrating the firing trigger returned to its unactuated position.
Figure 40:
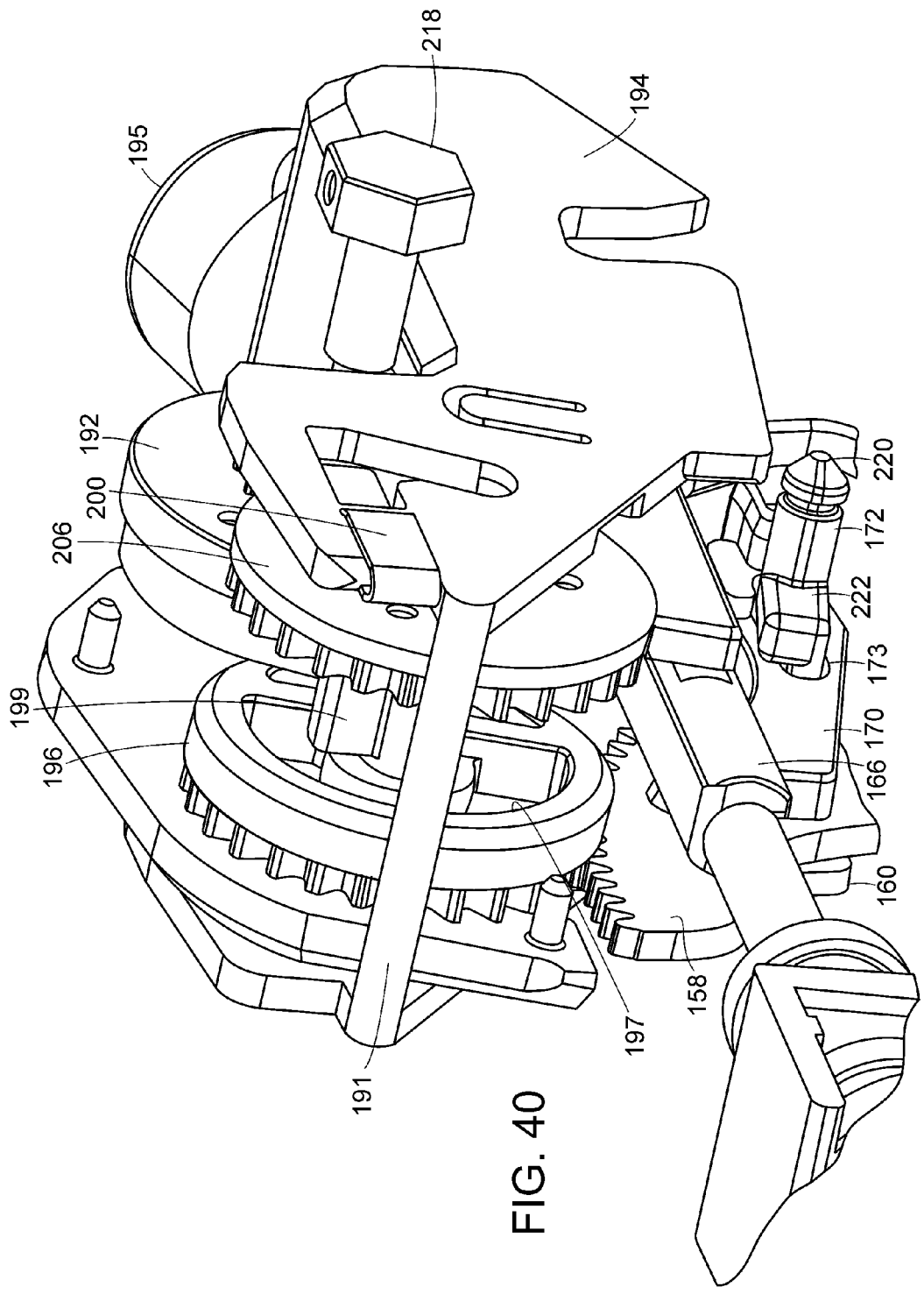
FIG. 40 is a perspective view of the return mechanism of FIG. 29 illustrating the return carriage returned to its unactuated position.
Figure 41:
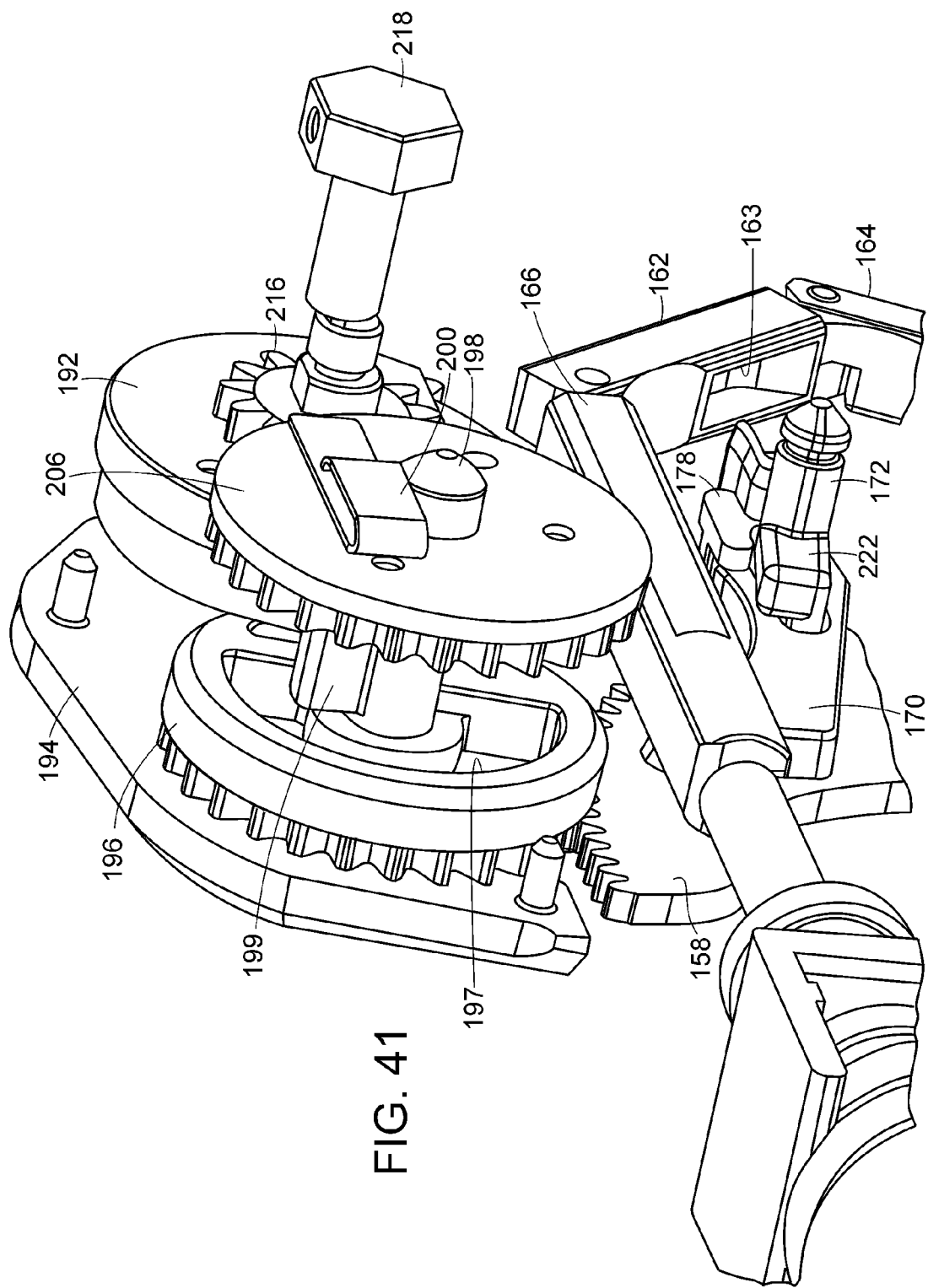
FIG. 41 is a perspective view of the return mechanism of FIG. 29 arranged in the configuration of FIG. 40 illustrating the relative relationship between a biasing spring and the return pin of the return mechanism with some components of the return mechanism removed.
Figure 42:
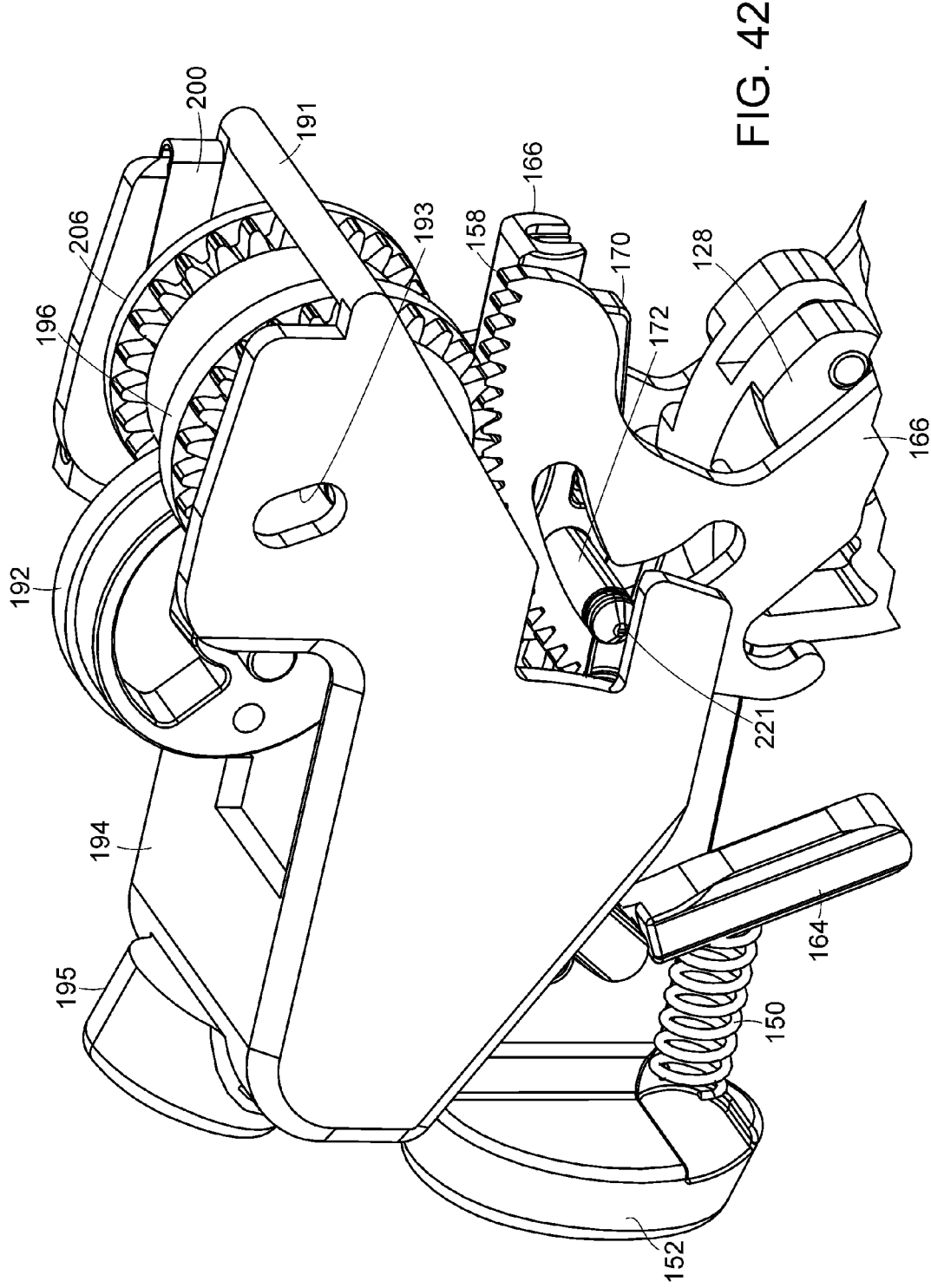
FIG. 42 is a perspective view of the return mechanism of FIG. 29 arranged in the configuration of FIG. 40 illustrating the return carriage operably engaged with the firing pin of the firing drive and the return pin of the return mechanism in order to reset the firing drive and the return mechanism to the their initial configurations.

Further to the above, when return pin 198 is slid toward trigger gear 196, D-shaped cavity 197 can be positioned such that key 199 does not immediately enter cavity 197. On the contrary, referring to FIG. 31, spring 200 can bias return pin 198 such that key 199 initially abuts face 204 of trigger gear 196. After trigger 160 is released and is returned to its unactuated position, however, D-shaped cavity 197 can be rotated and aligned with key 199 such that spring 200 can bias key 199 into cavity 197 as illustrated in FIG. 36. In at least one embodiment, referring to FIG. 31, when return pin 198 is slid toward trigger gear 196, an end of return pin 198 can be received in slot 193 in return carriage 194 as illustrated in FIG. 32. After key 199 has been inserted into cavity 197, a subsequent actuation of trigger 160 can cause drive surface 210 of D-shaped cavity 197 to abut key 199 and rotate return pin 198 to a position illustrated in FIGS. 37 and 38. In effect, an actuation of trigger 160, in at least one embodiment, can rotate key 199 approximately half a revolution such that key 199, which is initially extending substantially downwardly (FIG. 36), can be rotated such that key 199 is extending substantially upwardly (FIG. 37). Thereafter, trigger 160 can be released and trigger gear 194 can be rotated relative to key 199 where key 199 can remain oriented in a substantially upward direction as illustrated in FIGS. 39-41.

Figure 38:
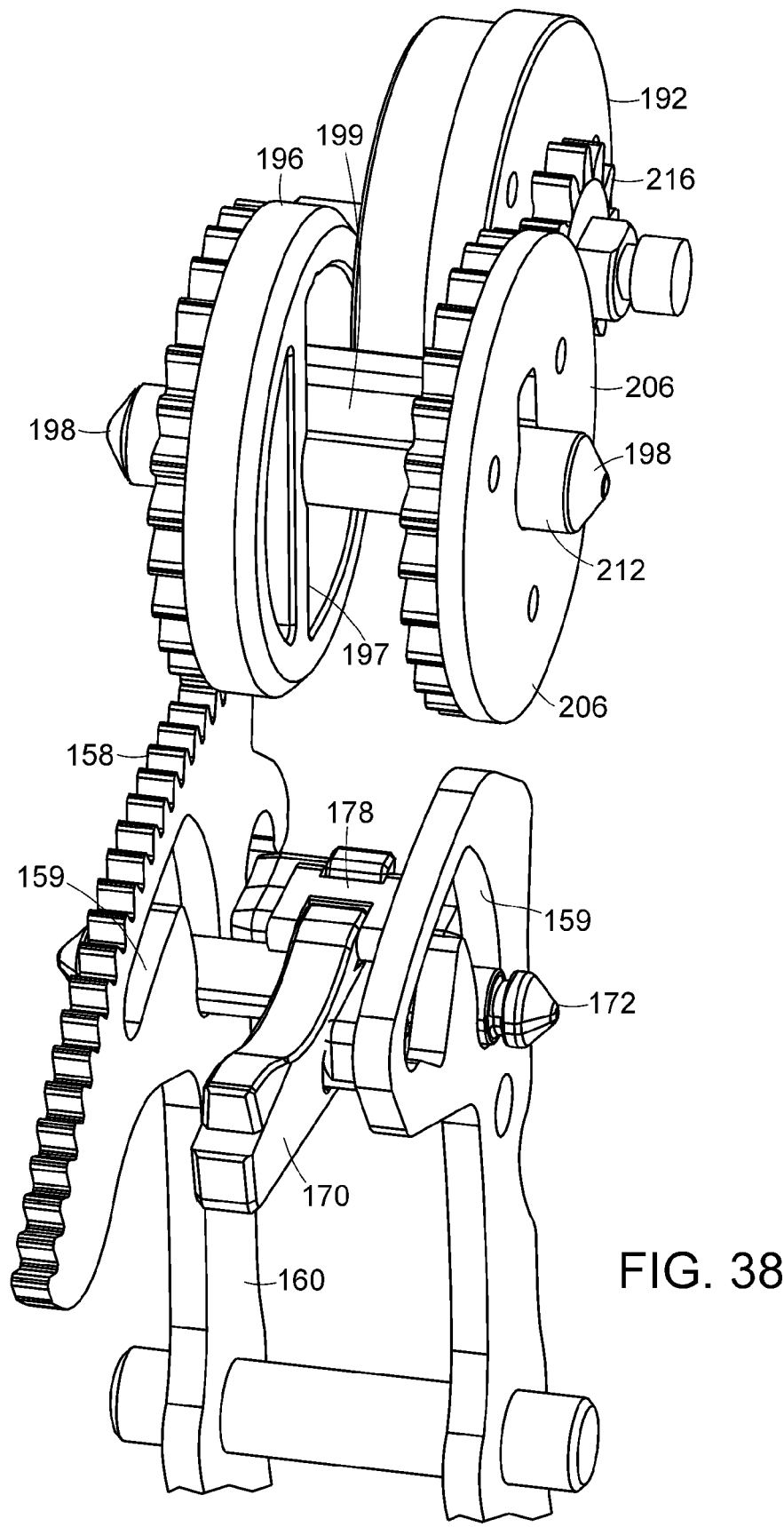
FIG. 38 is an additional perspective view of the return mechanism of FIG. 29 arranged in the configuration illustrated in FIG. 37.

In various embodiments, referring primarily to FIG. 38, key gear 206 can be operably engaged with return pin 198 such that the rotation of return pin 198 can be transmitted to key gear 206. In at least one embodiment, key gear 206 can include key-shaped aperture 212 which can be configured to slidably receive key 199 of return pin 198. In at least one such embodiment, key 199 can be operably engaged with both recess 197 of trigger gear 196 and aperture 212 of key gear 206 when return pin 198 is engaged with trigger gear 196. In various alternative embodiments, key gear 206 can be fixedly mounted to return pin 198. In such embodiments, when return pin 198 is slid relative to trigger gear 196, key gear 206 can also be slid relative to trigger gear 196. In various embodiments, referring generally to FIG. 38, reel 192 can include spur gear 216 mounted thereto, where spur gear 216 can be operatively engaged with key gear 206 such that the rotation of key gear 206 can be transmitted to reel 192. In at least one embodiment, key gear 206, when it is slid toward trigger gear 196 as described above, can be slid into operative engagement with reel 192. In alternative embodiments, spur gear 216 can be configured such that key gear 206 is in operative engagement therewith regardless of whether key gear 206 has been biased toward trigger gear 196.

As a result of the above, when return carriage 194 is positioned in its actuated position illustrated in FIG. 32, an actuation of trigger 160 can rotate reel 192 and wind band 190 around at least a portion thereof. In the event that key 199 cannot be operably engaged with trigger gear 196 when return carriage 194 is actuated, reel 192 can be rotated manually to retract band 190. In at least one such embodiment, referring to FIGS. 33 and 37, bolt, or fastener, 218 can be operatively engaged with reel 192 such that the rotation of bolt 218 can effect rotation of reel 192. In various embodiments, a surgeon can insert bolt 218 through an opening in surgical instrument housing 103 and engage bolt 218 with reel 192. In at least one embodiment, surgical instrument 100 can further include a counting mechanism (not illustrated) which can count the actuations of trigger 160 and, in at least one such embodiment, bolt 218, for example, can be operably engaged with the counting mechanism to rotate reel 192. In various embodiments, as a result, the surgical instrument can include a first, or primary, actuator for winding reel 192 and a second actuator which can be configured to wind reel 192 in lieu of the first actuator.

In various embodiments, as described above, reel 192 can be configured to pull band 190 and retract firing member 166 and firing links 162 and 164 proximally. More particularly, as described above, firing member 166 and firing links 162 and 164 can be retracted relative to pawl 170 in order to reposition firing member 166 and firing links 162 and 164 in their starting positions. In such embodiments, especially in embodiments where pawl 170 is pivotable as described above, the return mechanism of surgical instrument 100 can be further configured to hold pawl 170 out of operative engagement with firing member 166 and firing links 162 and 164 while they are moved relative to pawl 170. More particularly, when return carriage 194 is moved into its actuated position illustrated in FIG. 35, return carriage 194 can be configured to contact an end of firing pin 172 and slide firing pin 172 toward pawl 170 such that firing pin 172 engages pawl 170 and prevents pawl 170 from pivoting upwardly. More particularly, referring to FIG. 34, firing pin 172 can include first end 220 which can include a beveled and/or rounded surface, for example, where, when return carriage 194 contacts first end 220, return carriage 194 can push firing pin 172 toward pawl 170. In at least one embodiment, pawl 170 can include recess 173 which can be configured to receive key 222 extending from firing pin 172 when firing pin 172 is moved toward pawl 170. When key 222 and recess 173 are operatively engaged, firing pin 172 can prevent pawl 170 from pivoting upwardly into engagement with firing member 166 and firing links 162 and 164.

After firing member 166 and firing links 162 and 164 have been retracted, a new staple cartridge 110 can be secured in end effector 106 and surgical instrument 100 can be reset such that it can be used to incise and staple soft tissue once again. In various embodiments, referring to FIGS. 39-42, return carriage 194 can be moved from its actuated position illustrated in FIG. 32 to its unactuated position illustrated in FIG. 40. In at least one embodiment, return carriage 194 can be rotated, or pivoted, upwardly when a force is applied to button portion 195. Alternatively, return carriage 194 can be moved upwardly when, referring to FIG. 29, trigger lock 148 is rotated upwardly to disengage follower portion 149 from closure trigger 128 in order to reopen end effector 106 as described above. More particularly, when a force is applied to button portion 152 of trigger lock 148, trigger lock 148 can be rotated upwardly such that projection 147 extending therefrom can contact return carriage 194 and move return carriage 194 upwardly as well. In either event, referring to FIG. 42, when return carriage 194 is moved upwardly into is unactuated position, return carriage 194 can disengage firing pin 172 from pawl 170 and, in addition, disengage return pin 198 from trigger gear 196. More particularly, return carriage 194 can be configured to abut beveled, or rounded, end 221 of firing pin 172 such that, when return carriage 194 is rotated upwardly, return carriage 194 can slide return pin 172 away from pawl 170 and disengage key 222 from recess 173. Similarly, when return carriage 194 is moved upwardly, a side wall of slot 193 can be configured to contact an end of return pin 198 and slide return pin 198 away from trigger gear 196 to disengage key 199 from D-shaped recess 197. In short, in at least the illustrated embodiment, when button portion 152 of lock member 148 is depressed and return carriage 194 is moved upwardly, the surgical instrument can be reset and can be reused once again.

Although the surgical instruments described above can be reset after the cutting member and staple driver have been completely advanced within end effector 106, button portion 195 of return carriage 194, for example, can be depressed after the cutting member and staple driver have been only partially advanced within end effector 106. In various embodiments, return carriage 194 can further include guide pin 191 extending between opposite sides of return carriage 194. In at least one such embodiment, guide pin 191 can be slidably received within guide slot 185 (FIG. 31) in frame 184 such that slot 185 and pin 191 can define a path for return carriage 194. In various embodiments, guide pin 191 and guide slot 185 can be configured to assure that return carriage 194 engages firing pin 172 and return pin 198 and resets the surgical instrument when return carriage 194 is moved from its actuated position to its unactuated position as described above.

Figure 43:
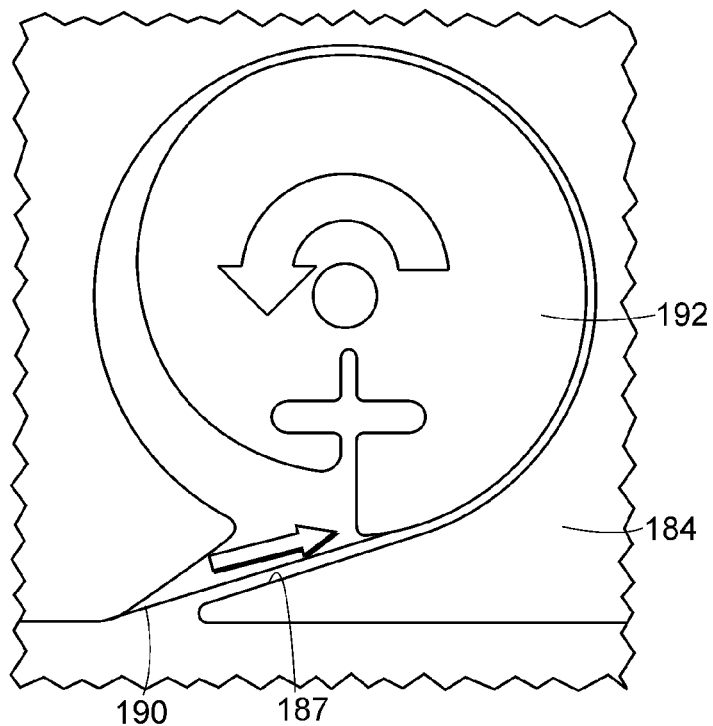
FIG. 43 is a detail view of a reel of the return mechanism of FIG. 29 illustrating the relative relationship between a return band of the return mechanism and the stapler frame of FIG. 26.
Figure 44:
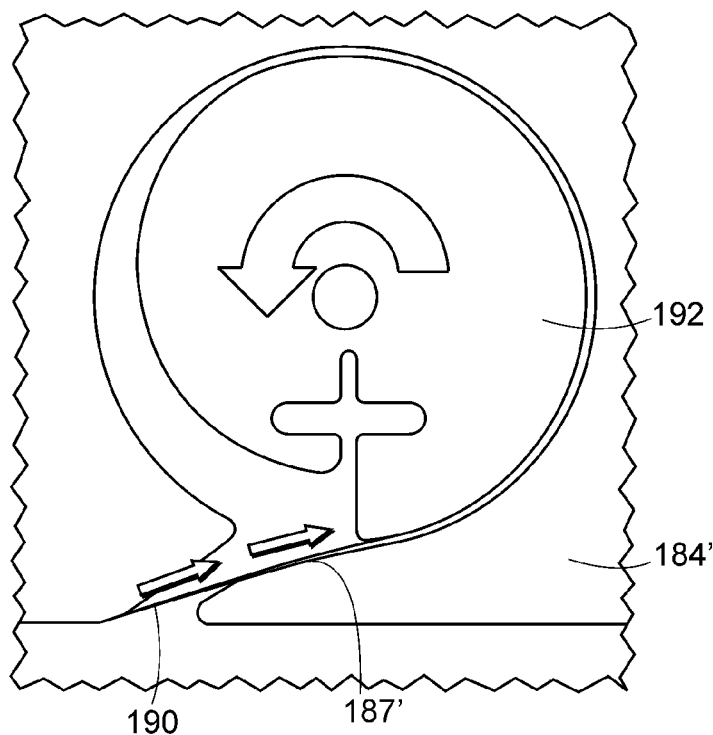
FIG. 44 is a detail view of the reel of FIG. 43 illustrating the relative relationship between the return band and an alternative embodiment of the stapler frame of FIG. 26.
Figure 45:
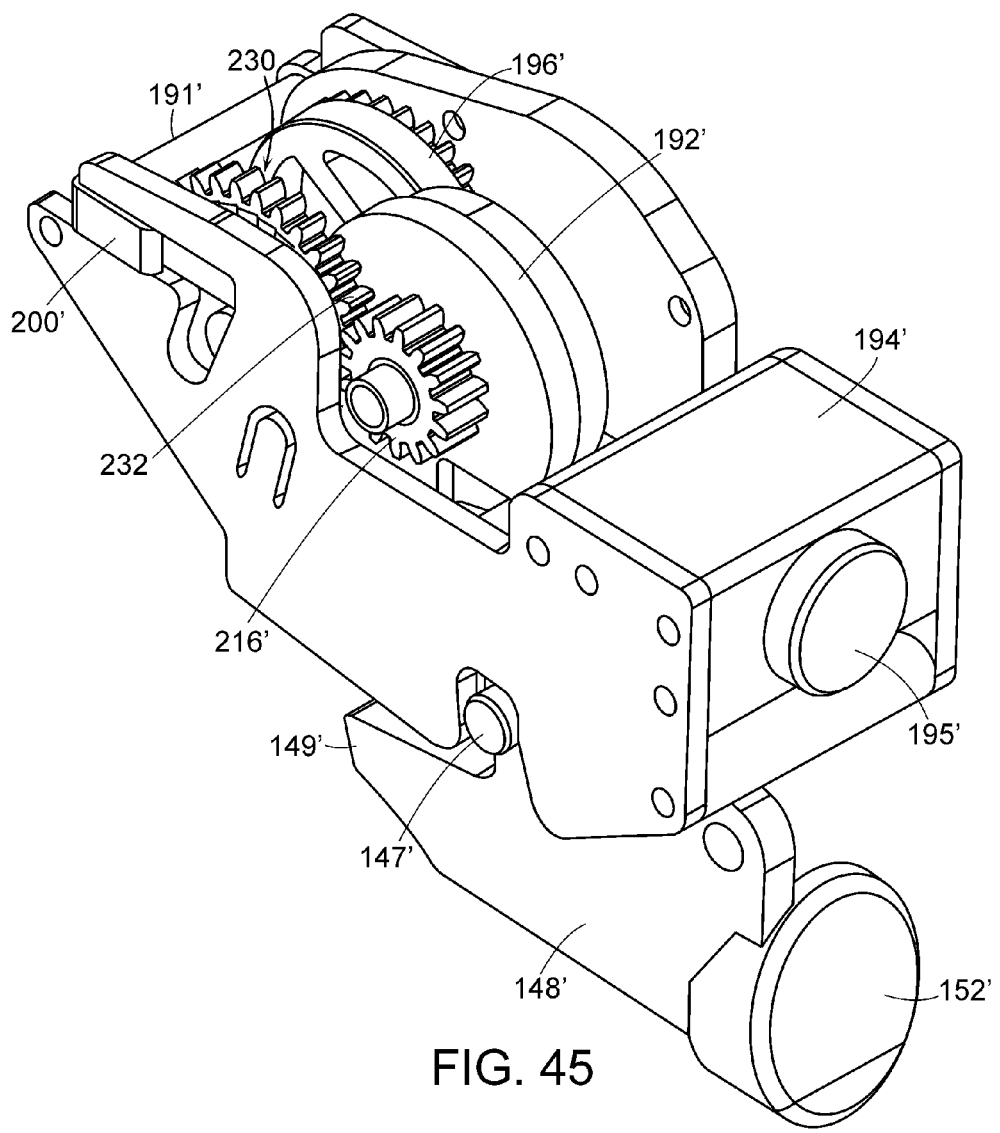
FIG. 45 is a perspective view of a return mechanism of a surgical instrument in accordance with an alternative embodiment of the present invention having an anti-back-up ratchet mechanism.
Figure 46:
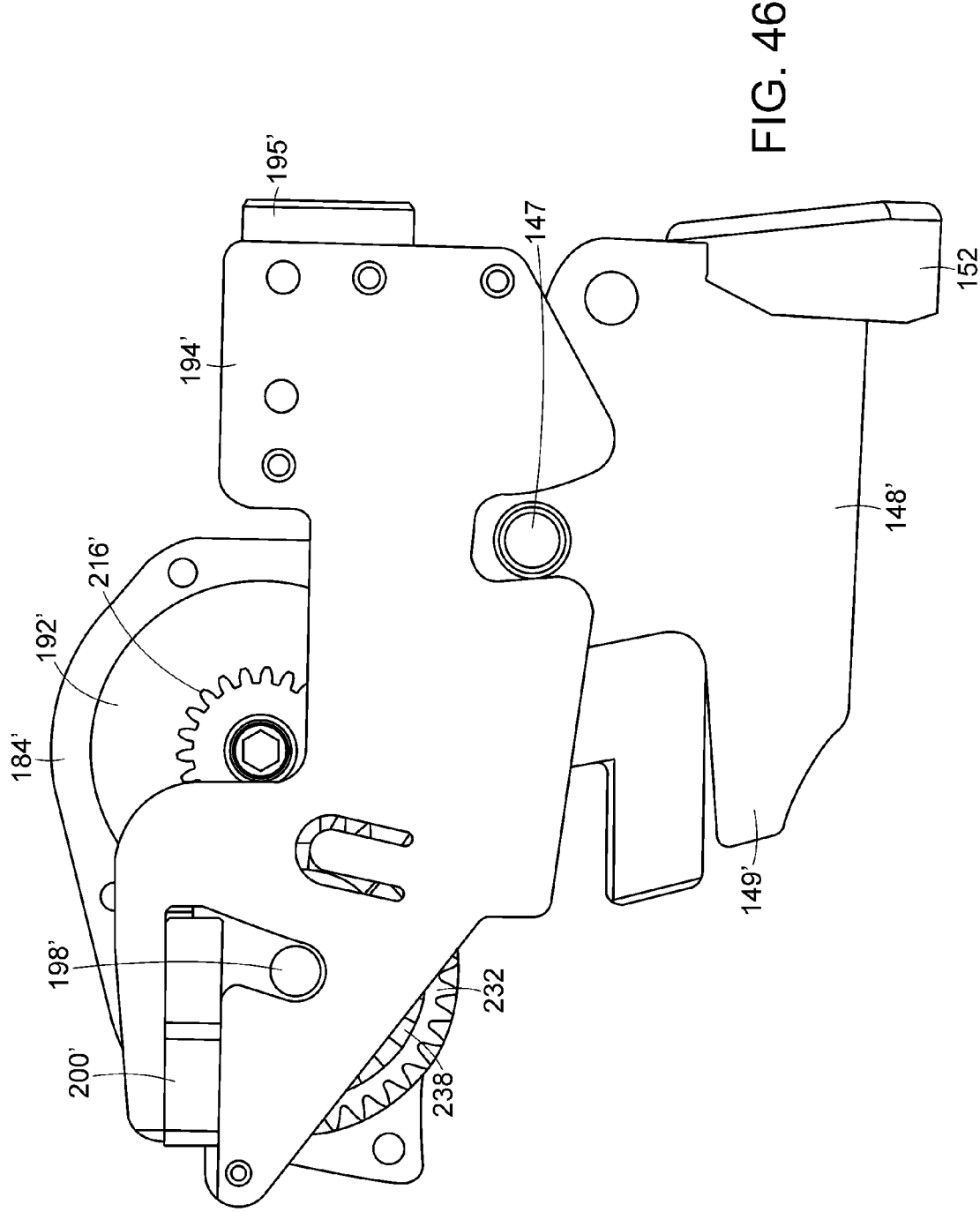
FIG. 46 is an elevational view of the return mechanism of FIG. 45 having a return carriage in an unactuated position.

In various embodiments, surgical instrument 100 can further include a brake for preventing, or at least partially inhibiting, the firing drive from advancing and/or retracting the cutting member and staple driver, for example, within end effector 106. In at least one embodiment, referring to FIG. 43, frame 184 can include brake surface 187 where brake surface 187 can be configured to apply a braking force to band 190. More particularly, when band 190 is pulled proximally and/or distally as described above, frame 184 can be configured such that band 190 slides over brake surface 187 and a friction force is created therebetween. In various embodiments, referring to FIG. 44, brake surface 187' can be configured such that the path of band 190 between firing member 166 and reel 192 is interrupted by brake surface 187' and a significant normal force can be applied to band 190.

In at least one embodiment, band 190 can be engaged with brake surface 187' when band 190 is at rest such that a static friction force between band 190 and brake surface 187' can prevent, at least initially, band 190 from moving relative to brake surface 187' when a pulling force is applied to band 190. When the pulling force applied to band 190 exceeds the static friction force, band 190 can be moved relative to brake surface 187'. Such embodiments may be particularly useful when trigger 160 is actuated more than one time to advance the cutting member and/or staple driver within end effector 106. More particularly, after an actuation of trigger 160, pawl 170 can be retracted relative to firing member 166 as described above and, in various embodiments, the friction force between band 190 and brake surface 187' can prevent, or at least partially inhibit, firing member 166 and/or firing links 162 and 164 from moving proximally, and/or distally, as pawl 170 is retracted. As a result of the above, the alignment between tooth 174 of pawl 170 and the recesses in firing member 166 and firing links 162 and 164 can be maintained when pawl 170 is moved relative thereto.

Similarly, in at least one embodiment, the stiffness of band 190 can also assist in holding firing member 166 and firing links 162 and 164 in position. More particularly, in order for firing member 166 to 'back up', or move proximally, firing member 166 would have to push band 190 proximally and, in effect, wind band 190 around reel 192. In various embodiments, the stiffness of band 190 can be such that a significant force to wind band 190 around reel 192 is required and, as a result, firing member 166 can be held in place. To further increase the force required to wind band 190 around reel 192, referring to FIG. 44, the path of band 190 can be controlled such that is not wound onto reel 192 in a tangential direction. More particularly, if the path of band 190 is such that it is wound onto reel 192 in a non-tangential direction, a portion of the force transmitted through band 190 will be lost thus resulting in a poor mechanical advantage for winding reel 192.

In various embodiments, surgical instrument 100 can include a brake which can be engaged with reel 192, or any other suitable component of the firing drive, to prevent firing member 166 and/or firing links 162 and 164 from being retracted unintentionally, for example. In at least one embodiment, although not illustrated, the brake can be moved between a first position and a second position, where, when the brake is in the first position, the brake can apply a first braking force to band 190, for example. In at least one such embodiment, the brake can apply, when it is in the second position, a second braking force to band 190, for example, which can be greater than or less than the first braking force. In various alternative embodiments, the brake may not be engaged with band 190 or any other portion of the firing drive when the brake is in the second position. In various embodiments, although not illustrated, surgical instrument 100 can include a detent mechanism which can apply a braking force to reel 192 and/or band 190. In at least one such embodiment, the detent mechanism can include a ball detent and a spring member for biasingly engaging the ball detent against reel 192 and/or band 190.

Figure 47:
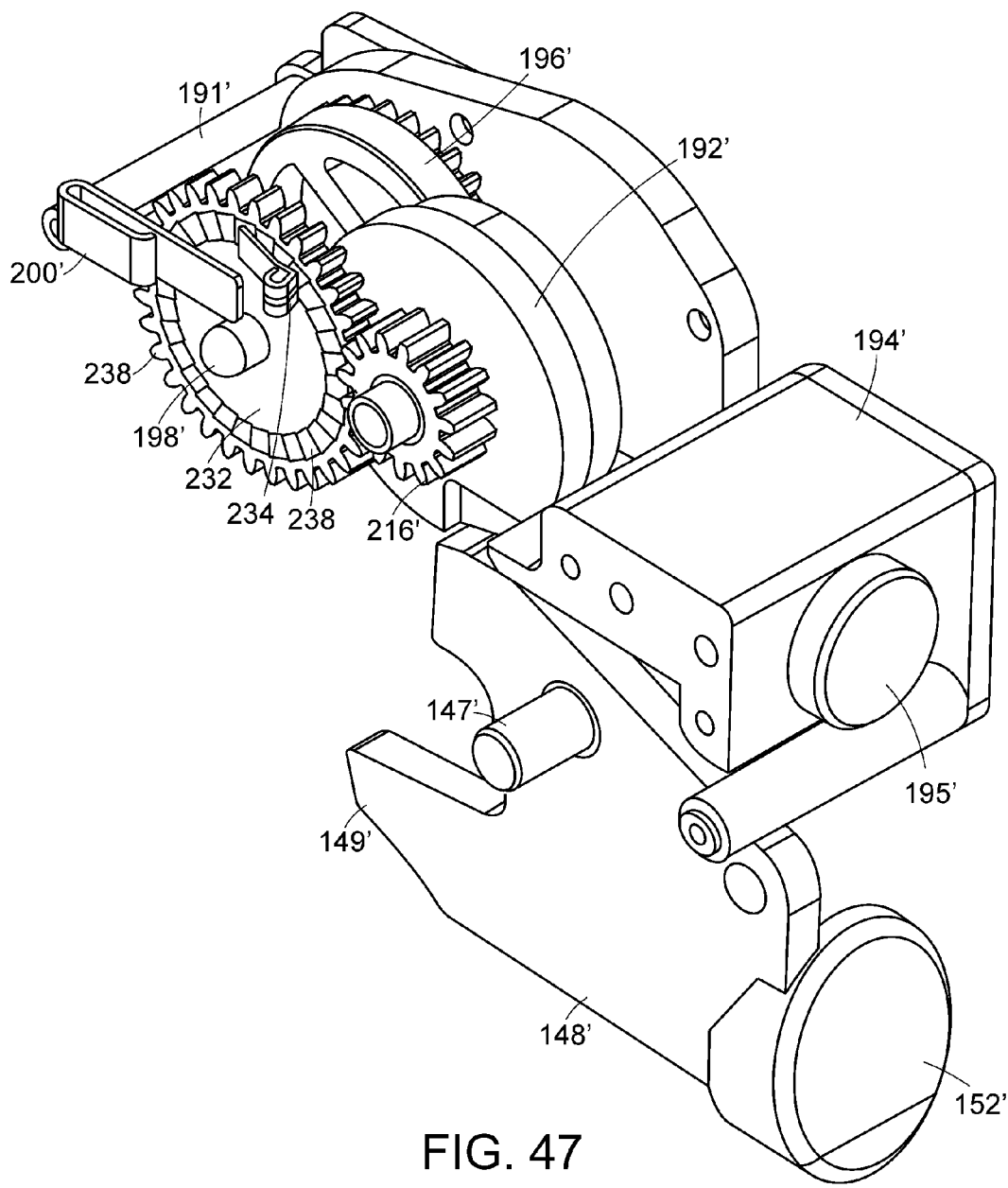
FIG. 47 is a perspective view of the return mechanism of FIG. 45 with some components of the surgical instrument removed.
Figure 48:
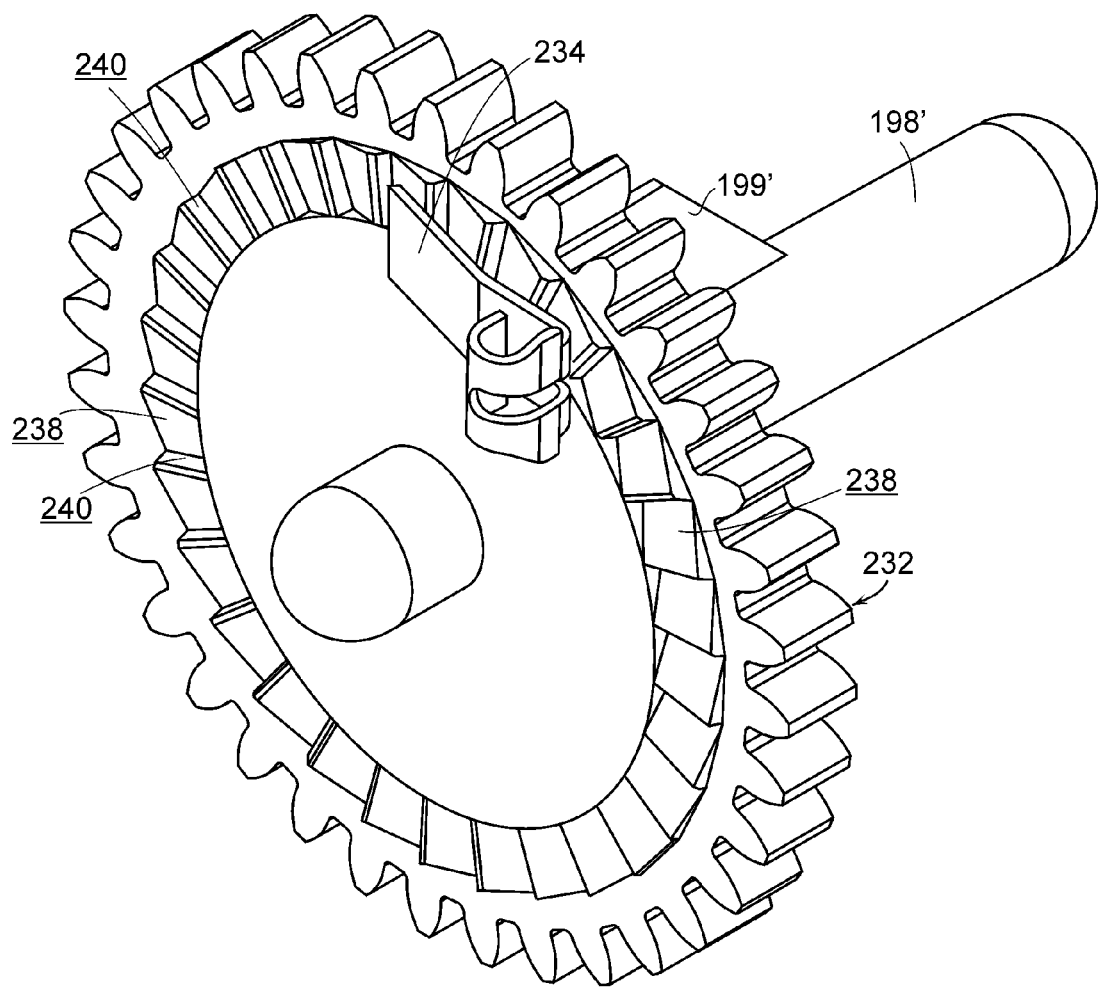
FIG. 48 is a perspective view of a return gear, return pin, and anti-back-up pawl of the ratchet mechanism of FIG. 45.
Figure 49:
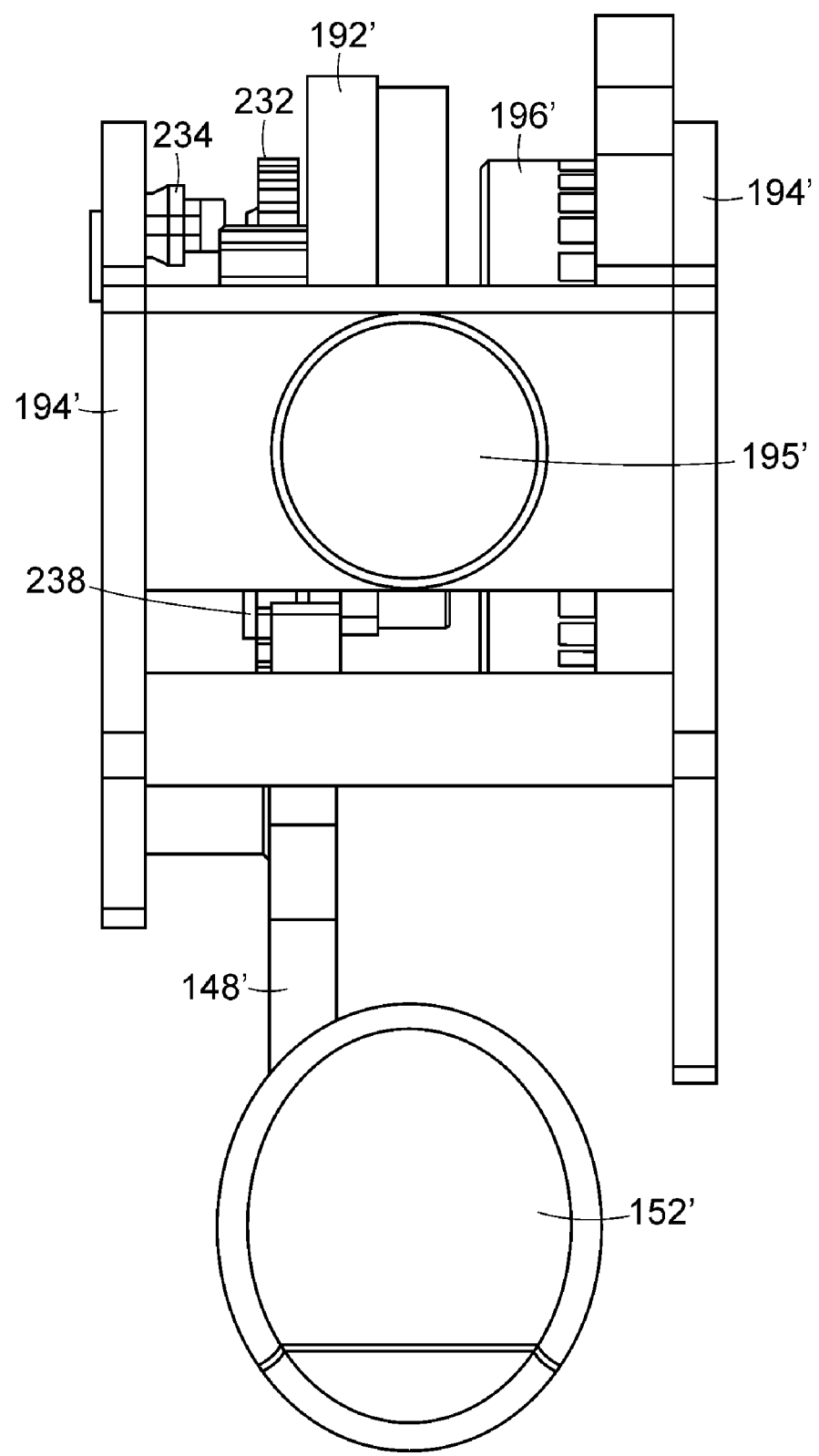
FIG. 49 is another elevational view of the return mechanism of FIG. 45.

In various embodiments, surgical instrument 100 can include a ratchet which can allow reel 192 to turn in a first direction but can, in various circumstances, prevent reel 192 from turning in a direction opposite the first direction. In at least one embodiment, referring to FIGS. 45-49, surgical instrument 100 can include ratchet assembly 230, where ratchet assembly 230 can include ratchet wheel 232 and ratchet pawl 234. In various embodiments, ratchet wheel 232 can operate in substantially the same way as key gear 206 described above except that, referring primarily to FIGS. 47 and 48, ratchet wheel 232 can include ratchet teeth 236 which can, owing to a ratcheting engagement with ratchet pawl 234, prevent ratchet wheel 232 from being turned in a clockwise direction, for example, when return carriage 194' is in its unactuated position (FIG. 47). More particularly, each ratchet tooth 236 can include a flat surface 240 where, referring to FIG. 48, at least one of flat surfaces 240 can abut edge 235 of pawl 234 and thereby prevent ratchet wheel 232 from being rotated in a clockwise direction.

Each ratchet tooth 236 can further include an inclined surface 238, where inclined surfaces 238 can be configured to slide underneath pawl 234 when ratchet wheel 232 is turned in a counter-clockwise direction. As a result of the above, ratchet assembly 230 can allow band 190 to be pulled distally by firing member 166, for example, but prevent, or at least substantially inhibit, band 190 from being moved proximally, at least when return carriage 194 is in its unactuated position. When return carriage 194' is pivoted downwardly into its actuated position, as described above with regard to return carriage 194, ratchet wheel 232 can be slid toward trigger gear 196' and out of operative engagement with ratchet pawl 234. Thereafter, as a result, ratchet wheel 232 can be rotated in either a clockwise or counter-clockwise direction without interference, or at least substantial interference, from ratchet pawl 234. In various alternative embodiments where ratchet wheel 232 is not slid toward trigger gear 196', ratchet pawl 234 can be moved downwardly and out of operative engagement with ratchet teeth 236 when return carriage 194' is moved into its actuated position. In either event, when return carriage 194' is in its actuated position, trigger gear 196' and return pin 198' can rotate ratchet wheel 232 and cam 192' to retract band 190 and firing member 166.

Figure 50:
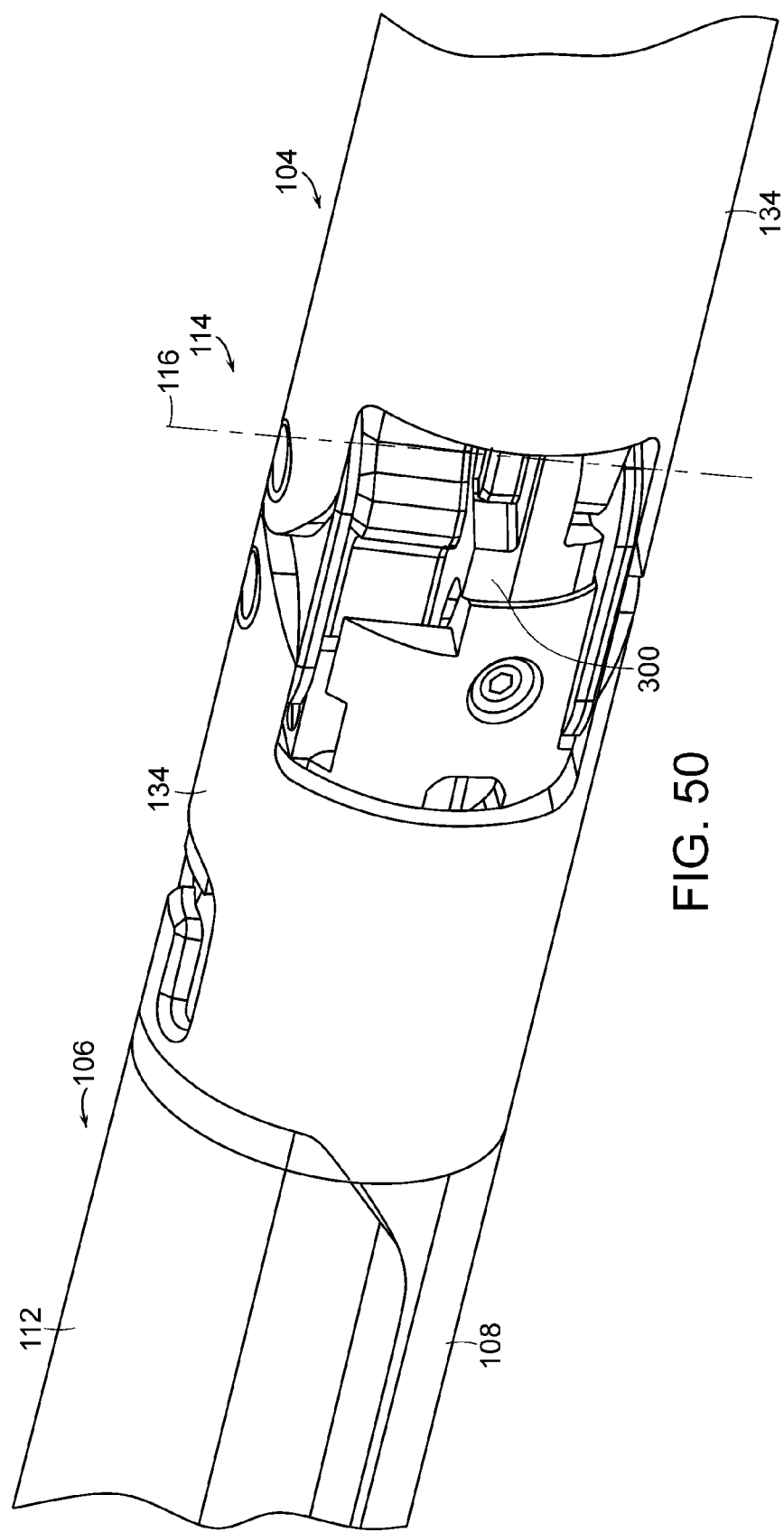
FIG. 50 is a perspective view of the articulation joint of FIG. 5.

In various embodiments, referring to FIG. 50, surgical instrument 100 can include end effector 106 and elongate shaft assembly 104, where end effector 106 and shaft assembly 104 can be pivotably connected by articulation joint 114. As outlined above, articulation joint 114 can allow end effector 106 to be moved, or articulated, relative to shaft assembly 106 about axis 116. In various circumstances, a surgeon can articulate end effector 106 to more easily access a surgical site within a patient's body. More particularly, a surgeon may insert end effector 106 and shaft assembly 104 through a cannula at least partially inserted into the patient's body and, once end effector 106 has passed through the cannula, end effector 106 can be pivoted, or articulated, in order to position end effector 106 relative to soft tissue, for example, in the surgical site that is to be stapled and/or incised. Once end effector 106 has been positioned, the relative relationship between end effector 106 and shaft assembly 104 can be fixed, or locked, by a locking mechanism as described in greater detail further below.

Figure 51:
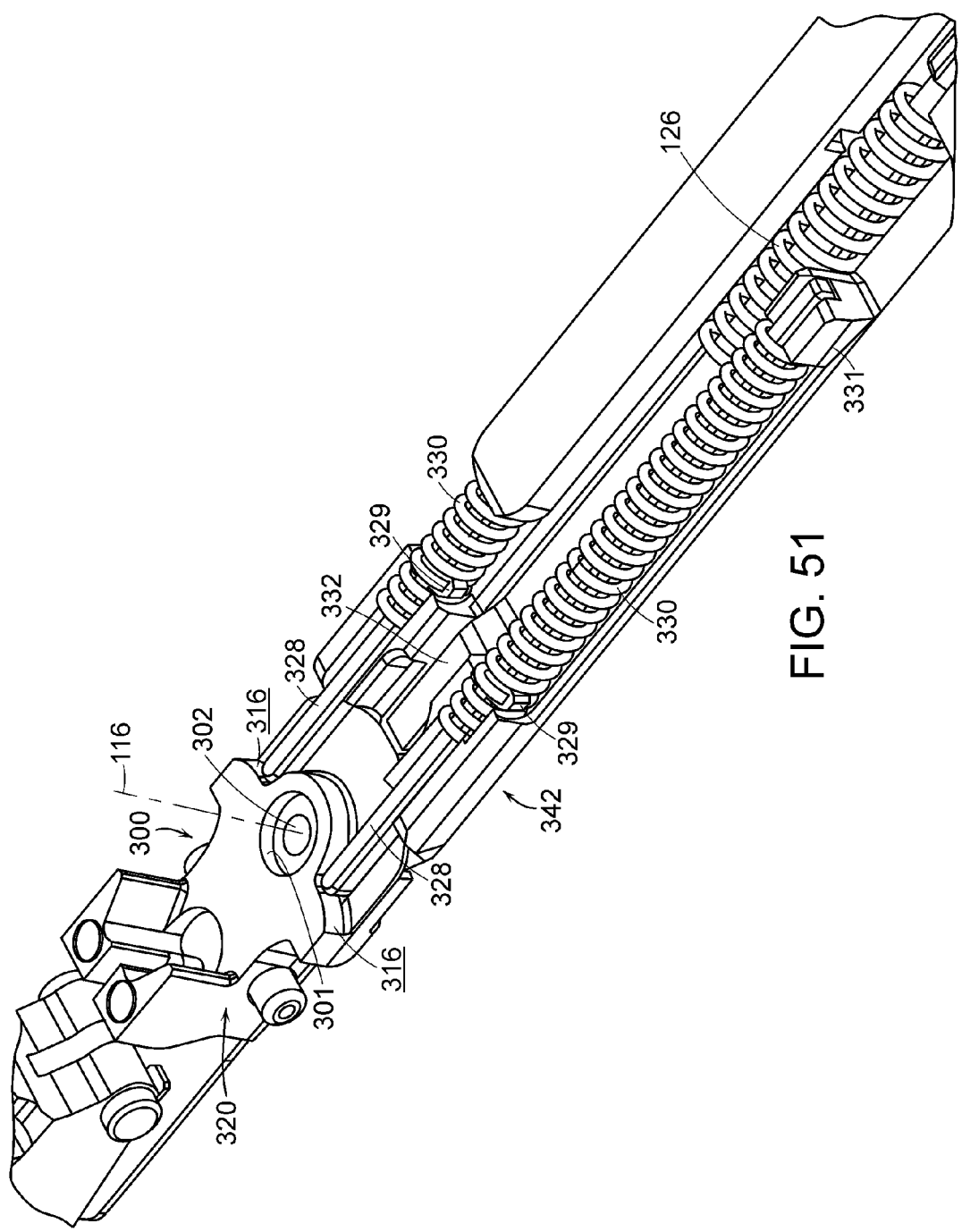
FIG. 51 is a perspective view of the articulation joint of FIG. 5 with some components of the surgical instrument removed.
Figure 52:
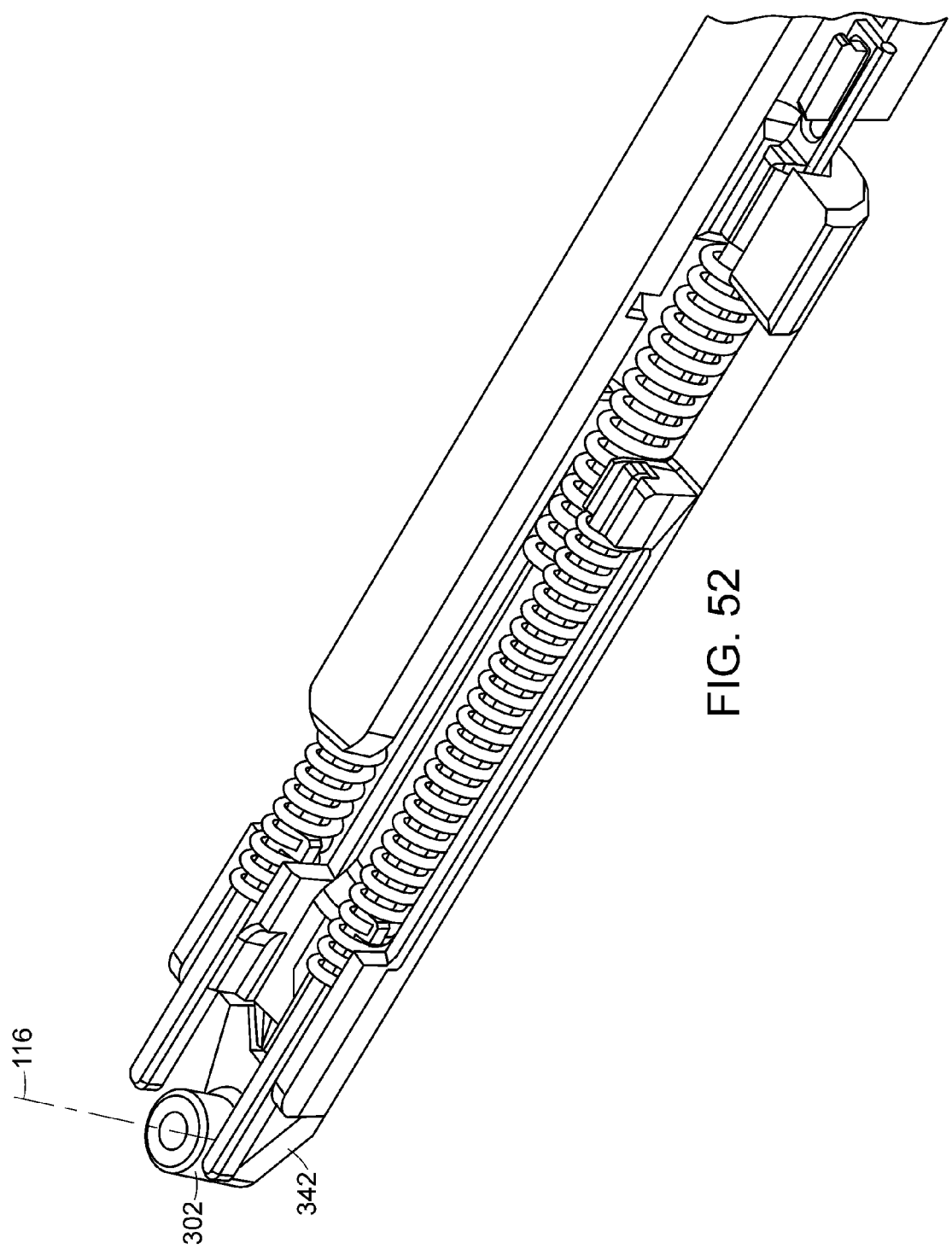
FIG. 52 is a perspective view of the articulation joint of FIG. 5 with additional components of the surgical instrument removed.
Figure 53:
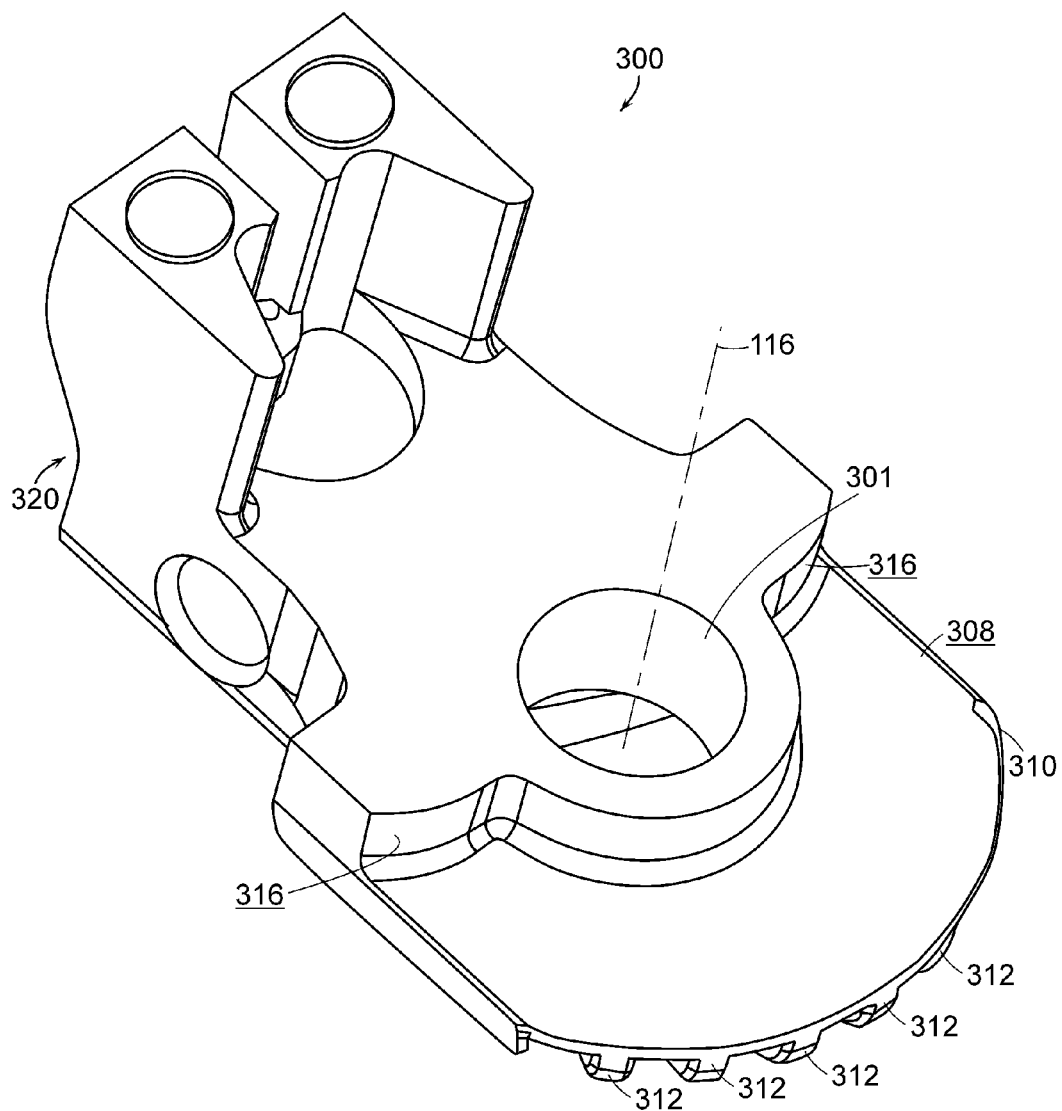
FIG. 53 is a perspective view of a lock member of the end effector of FIG. 3.
Figure 54:
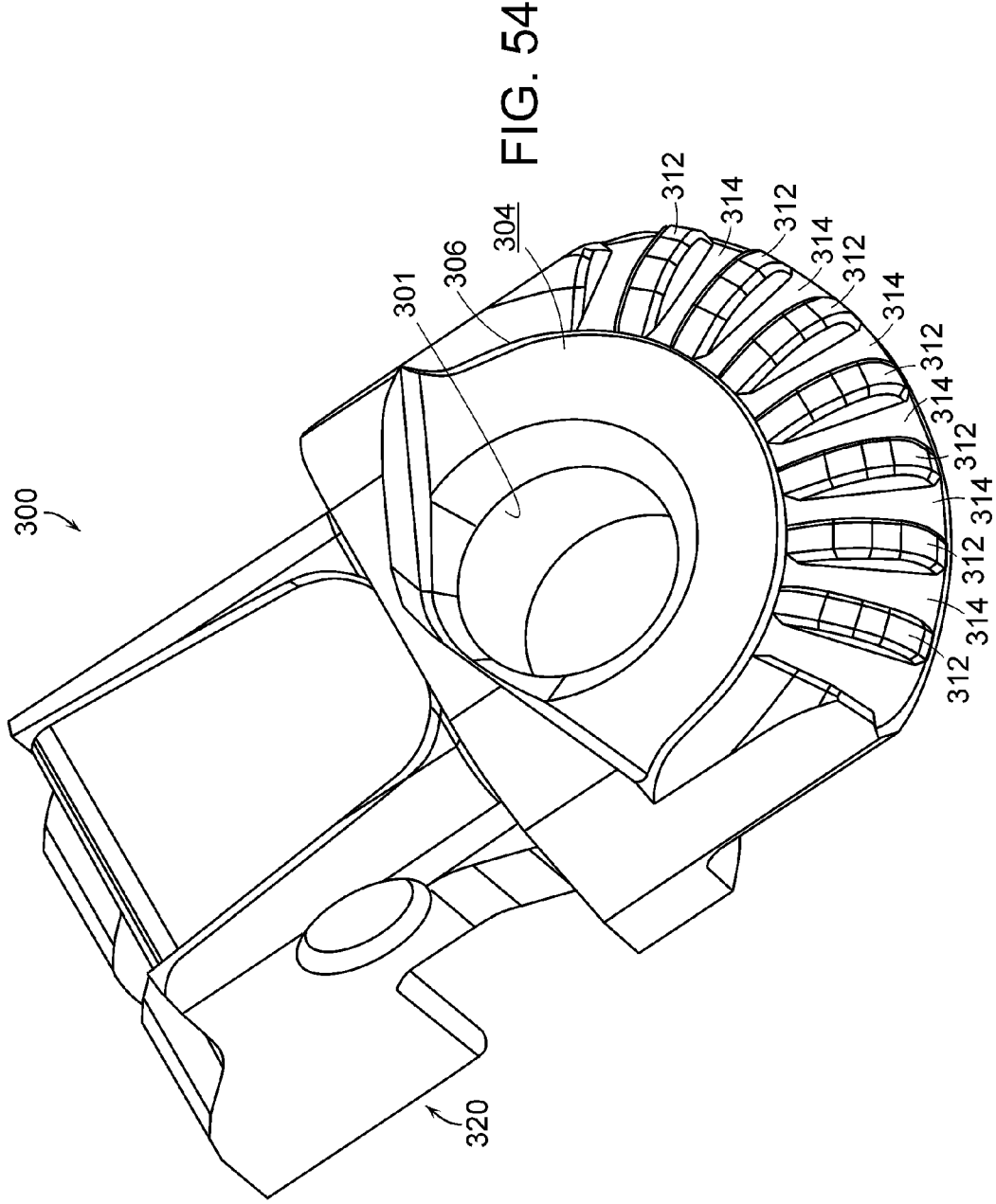
FIG. 54 is another perspective view of the end effector lock member of FIG. 53.
Figure 55:
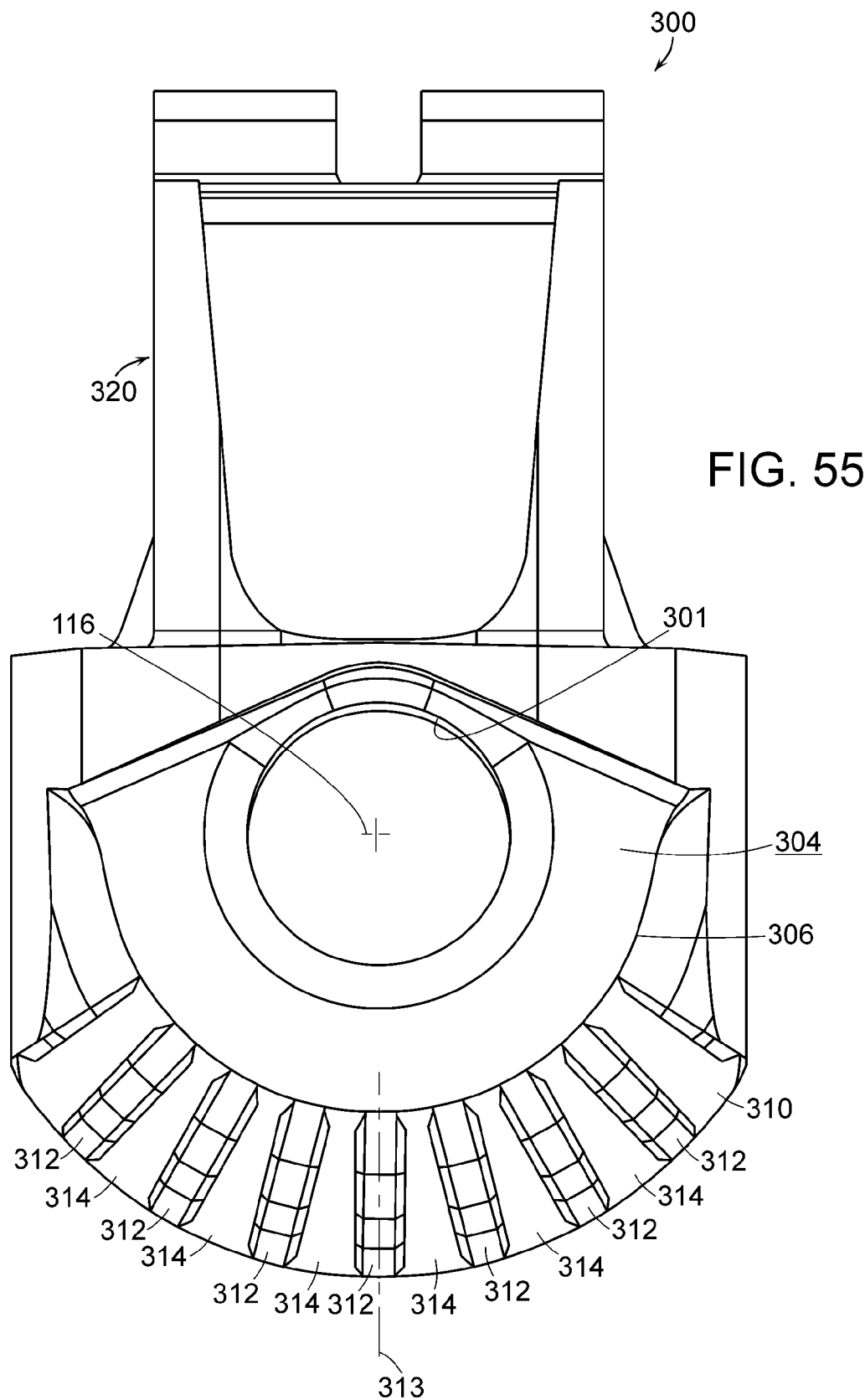
FIG. 55 is a bottom view of the end effector lock member of FIG. 53.
Figure 56:
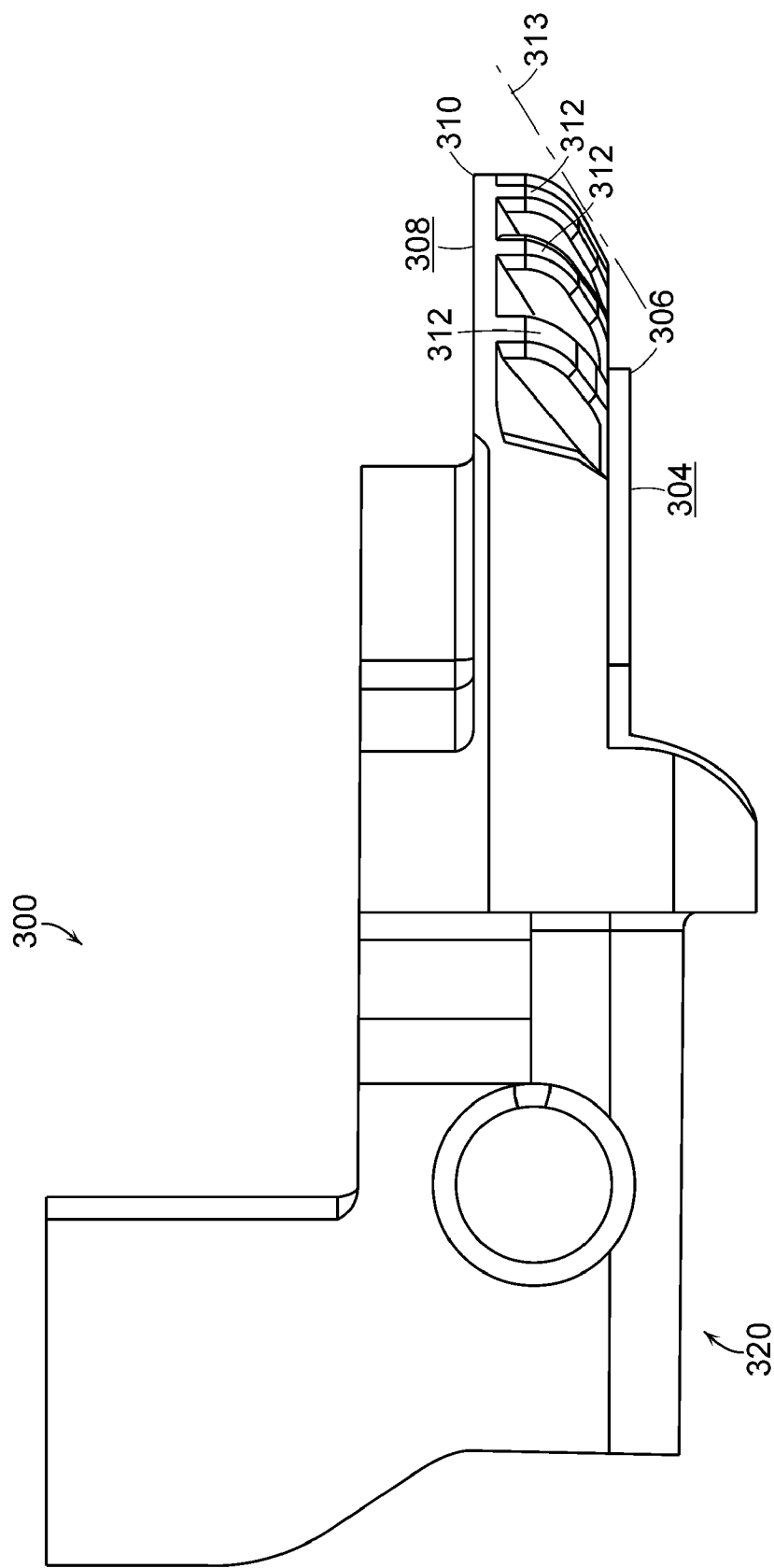
FIG. 56 is an elevational view of the end effector lock member of FIG. 53.

In at least one embodiment, referring to FIGS. 51 and 52, articulation joint 114 can include end effector lock member 300 and pivot 302. In various embodiments, referring to FIGS. 53-56, end effector lock member 300 can include connector portion 320 which can secure lock member 300 to end effector 106 and, referring to FIG. 52, shaft assembly 104 can include pivot connector 342, where pivot connector 342 can include pivot 302 extending therefrom. In various embodiments, lock member 300 can include aperture 301 which can be sized and configured to receive at least a portion of pivot 302 therein. In at least one embodiment, pivot 302 and aperture 301 can be configured such that end effector 106 can rotate freely about axis 116. In other various embodiments, pivot 302 and aperture 301 can be configured such that friction between pivot 302 and aperture 301 can resist, although permit, relative movement between end effector 106 and shaft assembly 104. Although not illustrated, articulation joint 114 can include more than one axis, or pivot, about which end effector 106 can be rotated.

In various embodiments, a surgeon can articulate end effector 106 relative to shaft assembly 104 by pushing end effector 106 against a cavity side wall surrounding a surgical site, for example, and applying a force to shaft assembly 104 such that end effector 106 pivots about axis 116. Thereafter, if the surgeon desires to re-center end effector 106, i.e., orient end effector 106 and shaft assembly 104 along a line, the surgeon can place end effector 106 against a cavity side wall once again, for example, and a apply a force to shaft assembly 104 as described above. In various embodiments, referring to FIGS. 51 and 52, surgical instrument 100 can include a re-centering mechanism which can automatically re-center, or at least substantially re-center, end effector 106 relative to shaft assembly 104. In various embodiments, end effector lock member 300 can include centering surfaces 316 and elongate shaft assembly 104 can include centering shafts 328 and biasing members 330, where biasing members 330 can be configured to bias centering shafts 328 against centering surfaces 316. In at least one such embodiment, centering surfaces 316 can be disposed on substantially opposite sides of axis 116 such that centering shafts 328 can apply a substantially equal torque, or moment, to lock member 300 and, absent an additional motivating force, hold end effector 106 in a substantially centered position. When end effector 106 is articulated by such a motivating force, as described above, lock member 300 can be configured to displace one of centering shafts 328 proximally and compress the biasing member 330 operably engaged therewith. More particularly, the biasing member 330 can be positioned between a guide 331 and at least one projection 329 extending from centering shaft 328 such that, when projection 329 is moved proximally by shaft 328, biasing member 330 is compressed therebetween. After the motivating force is removed, the compressed biasing member 330 can expand and rotate lock member 300 to its center position via centering shaft 328, or to a position where the torque applied by biasing members 330 is substantially balanced. Although biasing member 330 is illustrated as a coil spring, biasing member 330 can include any suitable elastic member.

In various embodiments, a locking mechanism can be used to hold end effector 106 in its articulated position even after the motivating force has been removed. In at least one embodiment, referring to FIGS. 53-56, end effector lock member 300 can include a first portion having first surface 308, a second portion having second surface 304, teeth 312, and recesses 314 defined between teeth 312 where, as described in greater detail further below, teeth 312 and recesses 314 can be configured to be operably engaged with a shaft assembly locking member in order to fix, or lock, the relative relationship between end effector 106 and shaft assembly 104. In various embodiments, teeth 312 and recesses 314 can be positioned intermediate first surface 308 and second surface 304. In at least one embodiment, first surface 308 can extend from aperture 301 to first perimeter 310, and second surface 304 can extend from aperture 301 to second perimeter 306. In various embodiments, first perimeter 310 can define a first plane and second perimeter 306 can define a second plane where teeth 312 and recesses 314 can be positioned intermediate the first and second planes. In embodiments where first perimeter 310 is different than second perimeter 306, teeth 312 can extend at an angle, or bevel, therebetween. In various embodiments, a tooth 312 can intersect first perimeter 310 at a point further away from axis 116 than a point at which the tooth 312 intersects second perimeter 306. In at least one embodiment, at least one of the teeth 312 can define a first axis 313 which can extend between first surface 308 and second surface 304 in a direction which is not perpendicular to first surface 308 and/or axis of rotation 116. In such embodiments, teeth 312 can slide over soft tissue, for example, which is positioned adjacent to articulation joint 114. Stated another way, owing to the angled, or beveled, surfaces of teeth 112, the probability of teeth 112 catching on, or impinging upon, the soft tissue surrounding articulation joint 114 when end effector 106 is articulated can be reduced. In at least one embodiment, teeth 312 may not extend beyond first perimeter 310 such that, in the event that at least a portion of first perimeter 310 is in contact with soft tissue, for example, first perimeter 310 and teeth 312 can, as above, easily slide relative to the soft tissue.

Figure 57:
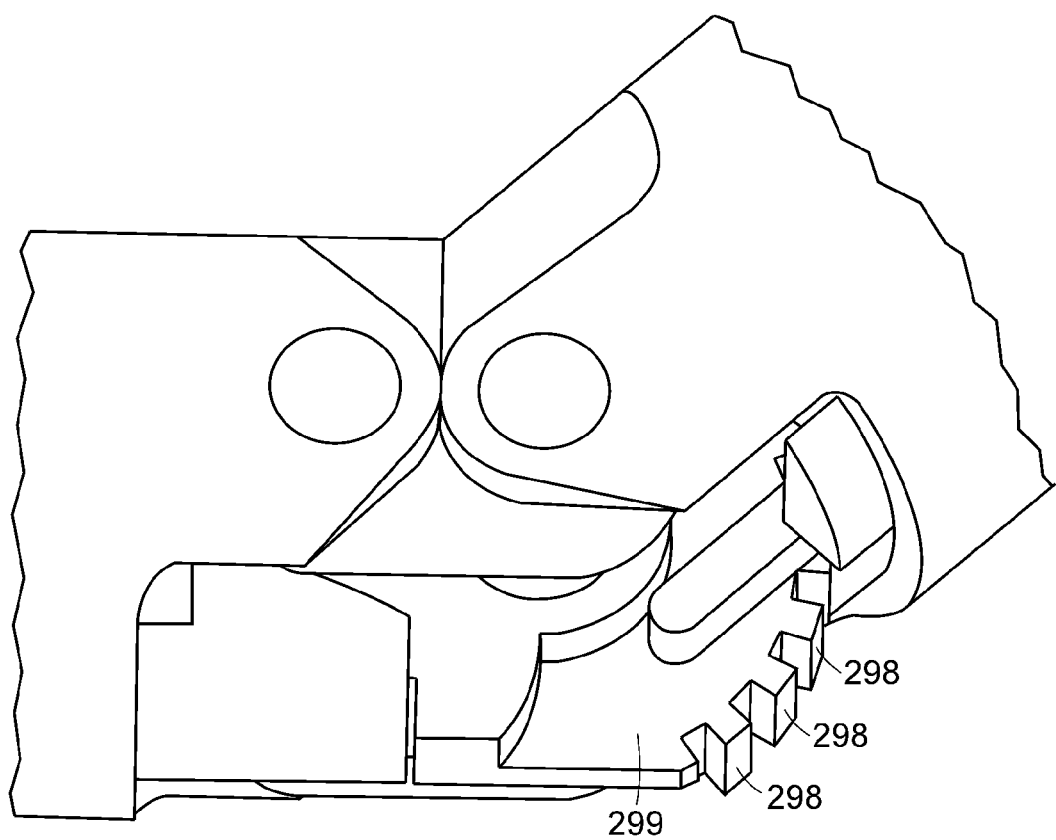
FIG. 57 is a partial perspective view of an articulation joint of a previous surgical instrument.
Figure 58:
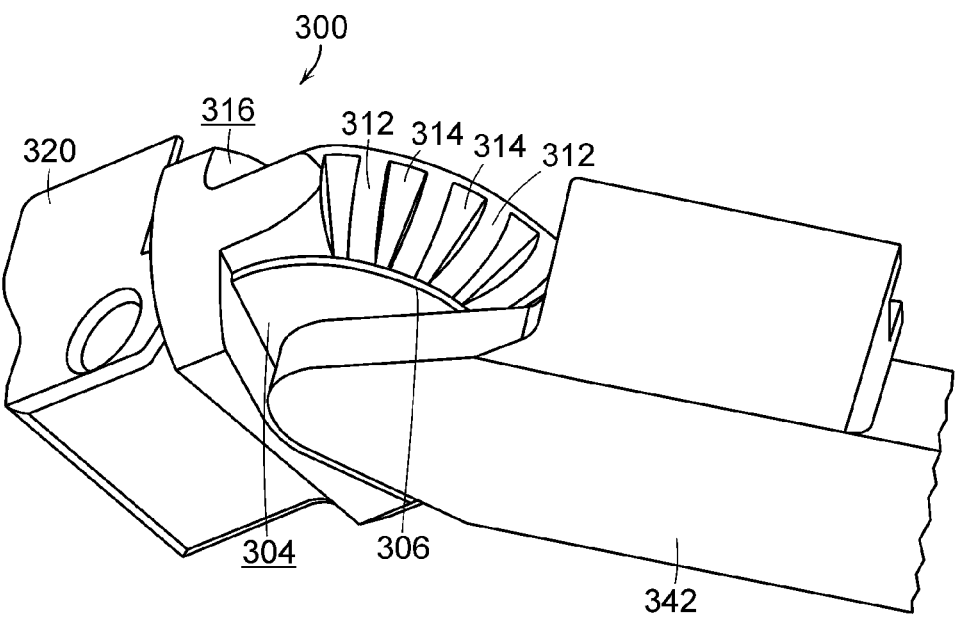
FIG. 58 is a perspective view of the articulation joint of FIG. 5 with some components of the end effector and elongate shaft assembly removed.
Figure 59:
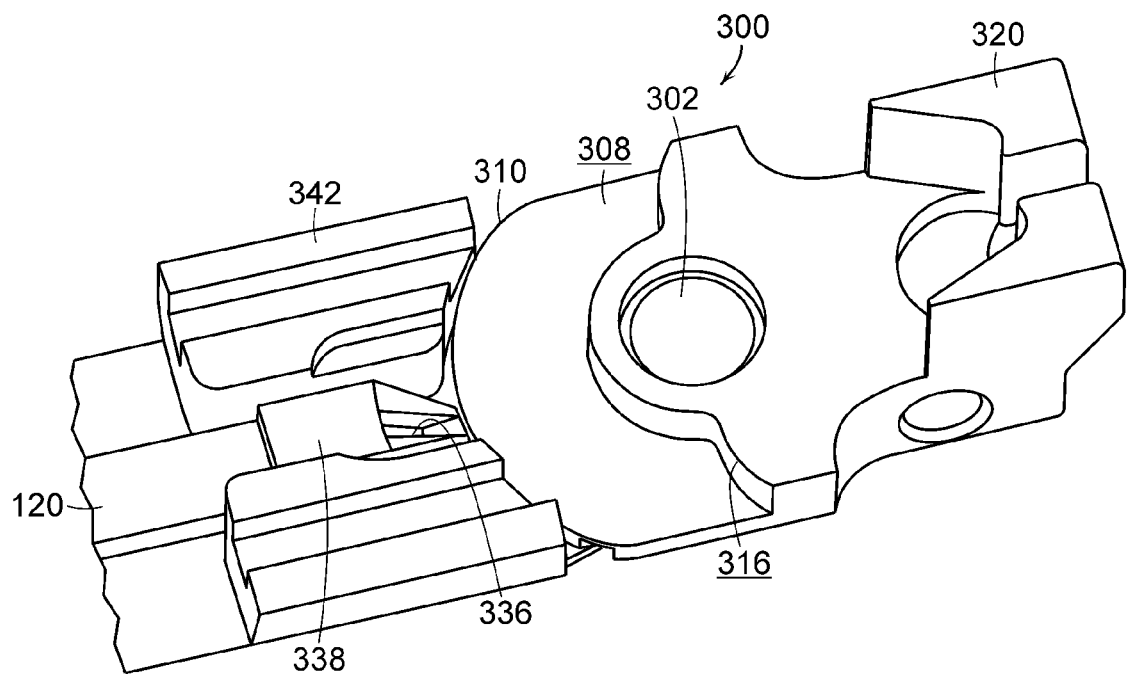
FIG. 59 is another perspective view of the articulation joint of FIG. 5 with some components of the end effector and elongate shaft assembly removed.
Figure 60:
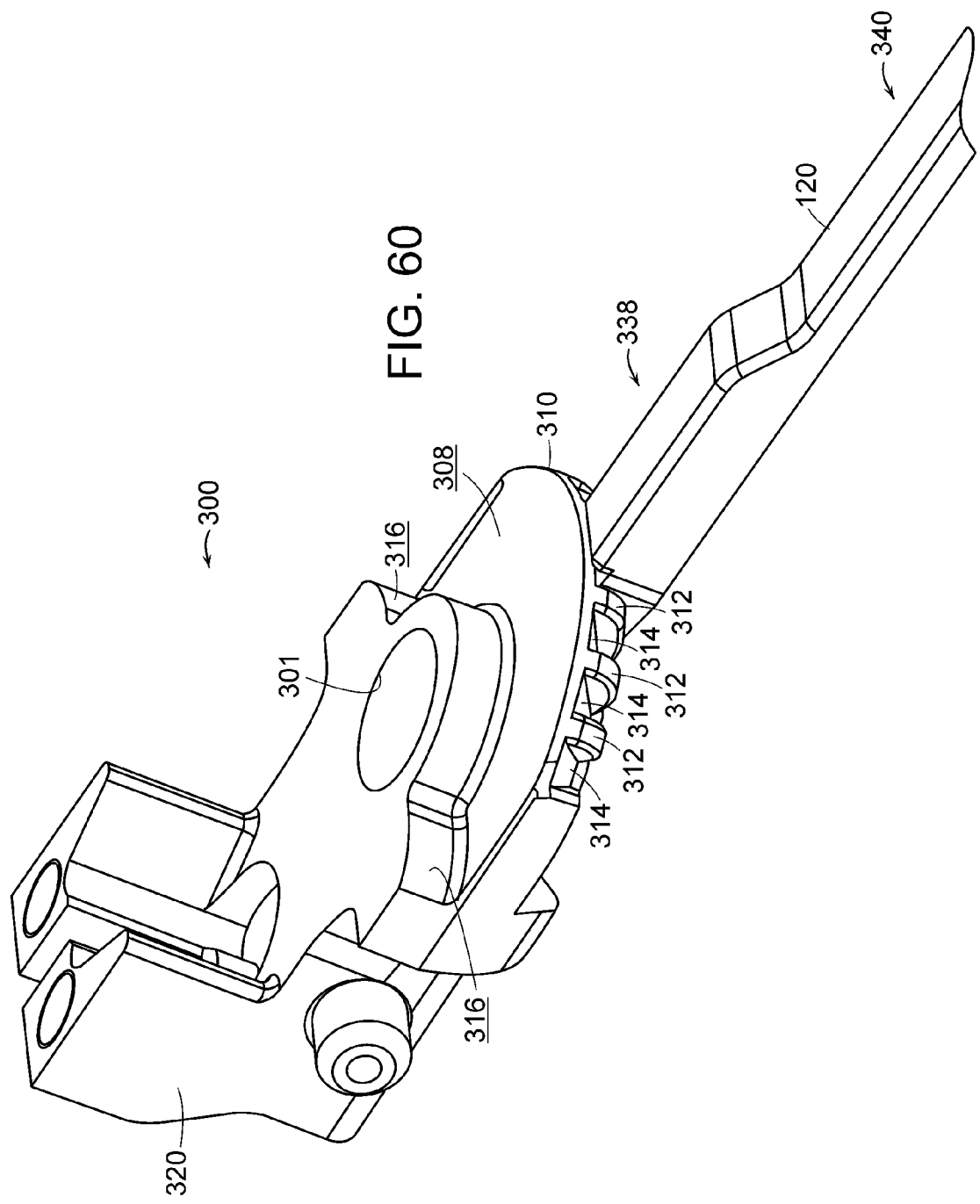
FIG. 60 is a perspective view of the end effector lock member of FIG. 53 operably engaged with a lock member of the elongate shaft assembly.
Figure 61:
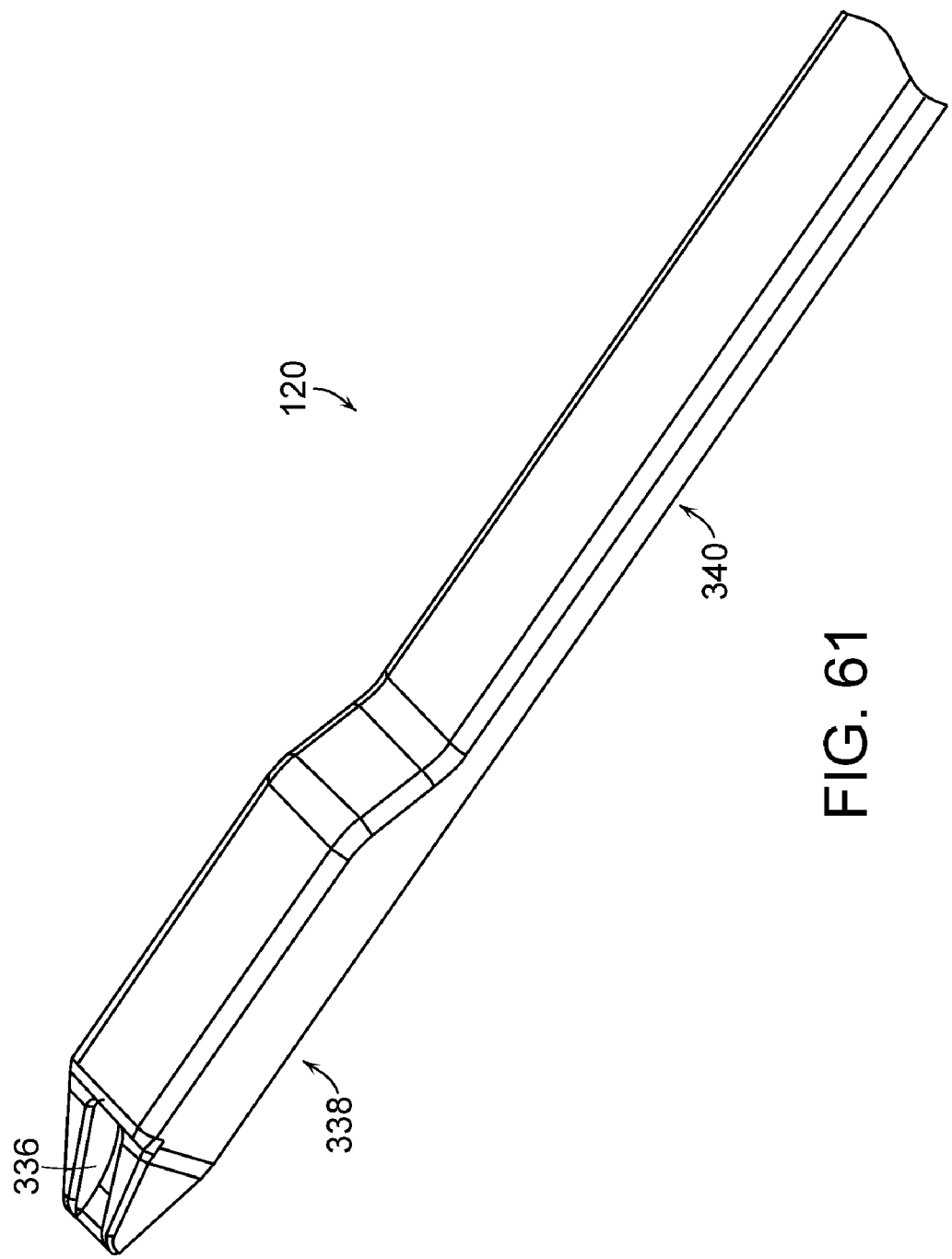
FIG. 61 is a perspective view of the shaft assembly lock member of FIG. 60.
Figure 62:
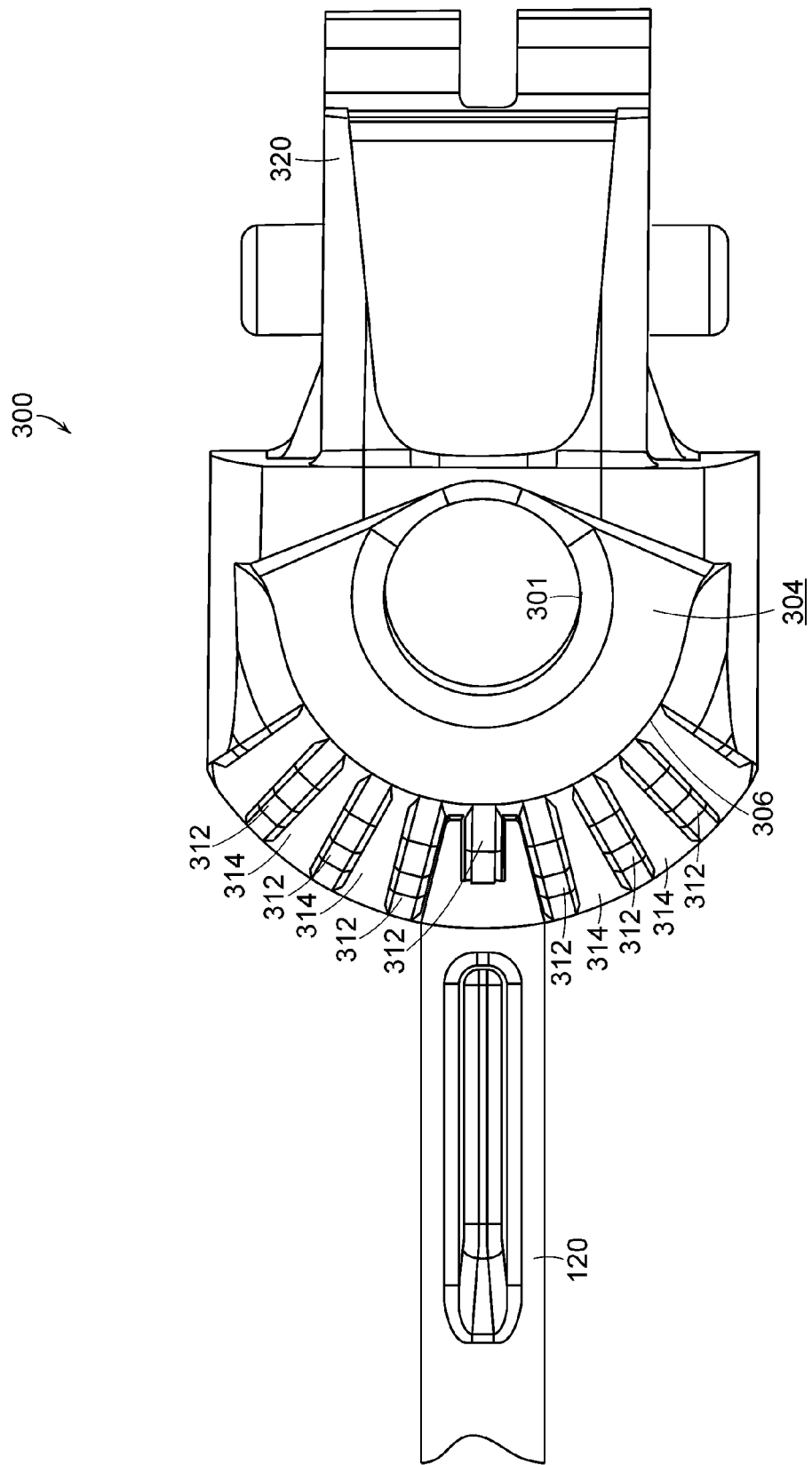
FIG. 62 is a bottom view of end effector lock member of FIG. 53 operably engaged with the shaft assembly lock member of FIG. 60.
Figure 63:
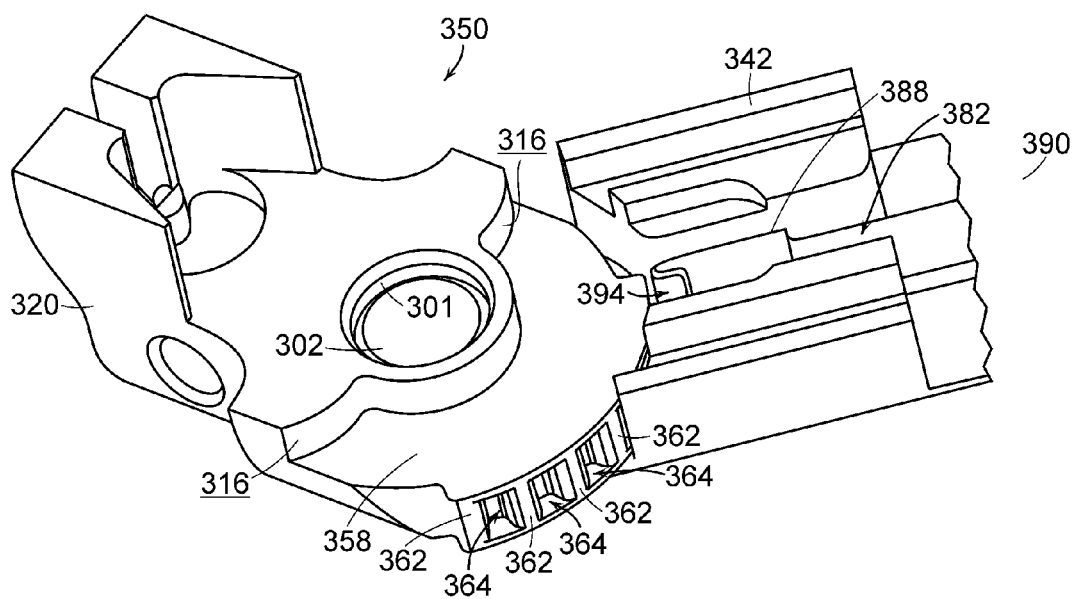
FIG. 63 is a perspective view of an articulation joint of a surgical instrument in accordance with an alternative embodiment of the present invention with some components of the surgical instrument removed.
Figure 64:
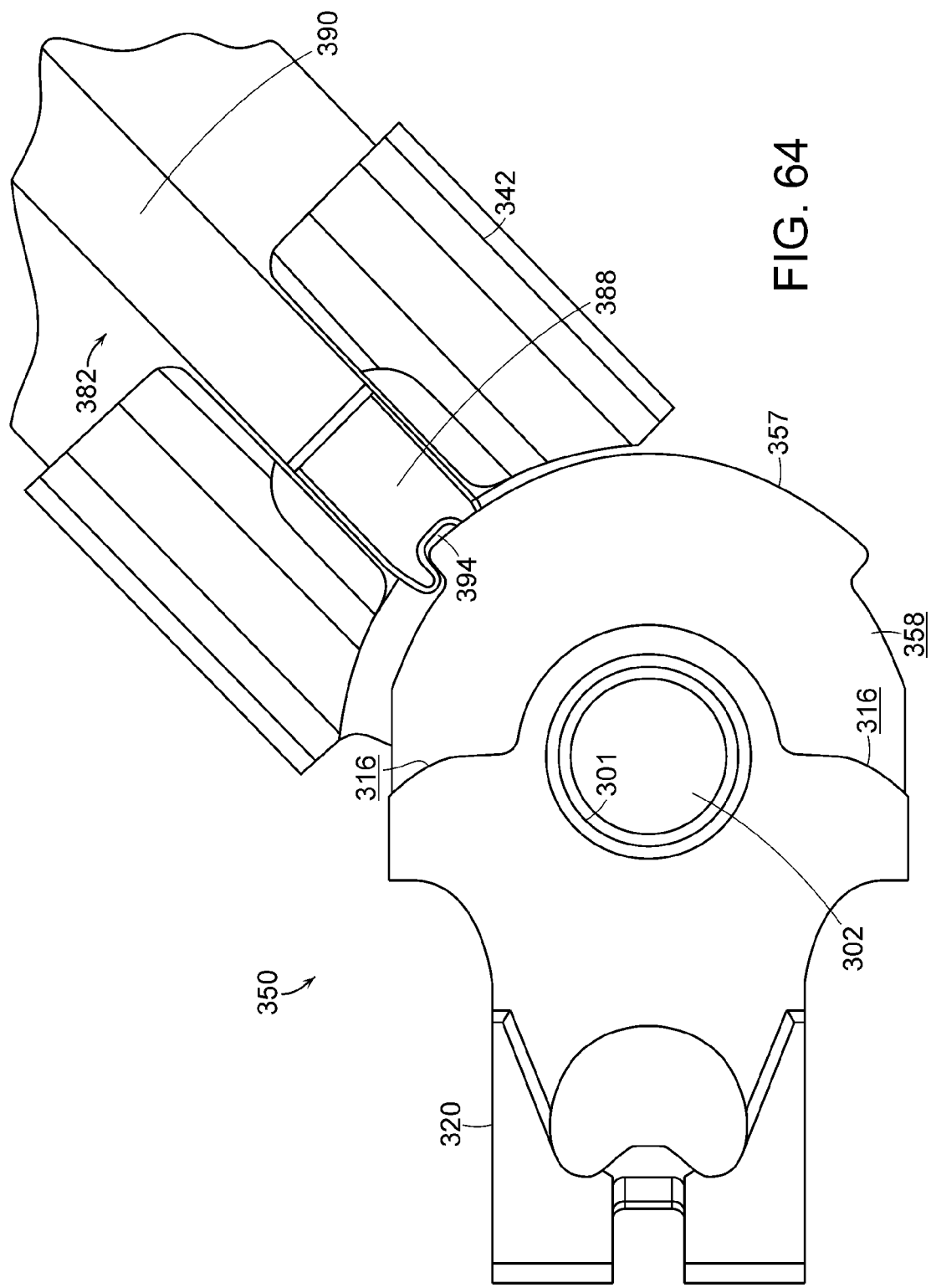
FIG. 64 is a top view of an end effector lock member operably engaged with a shaft assembly lock member of the surgical instrument of FIG. 63.
Figure 65:
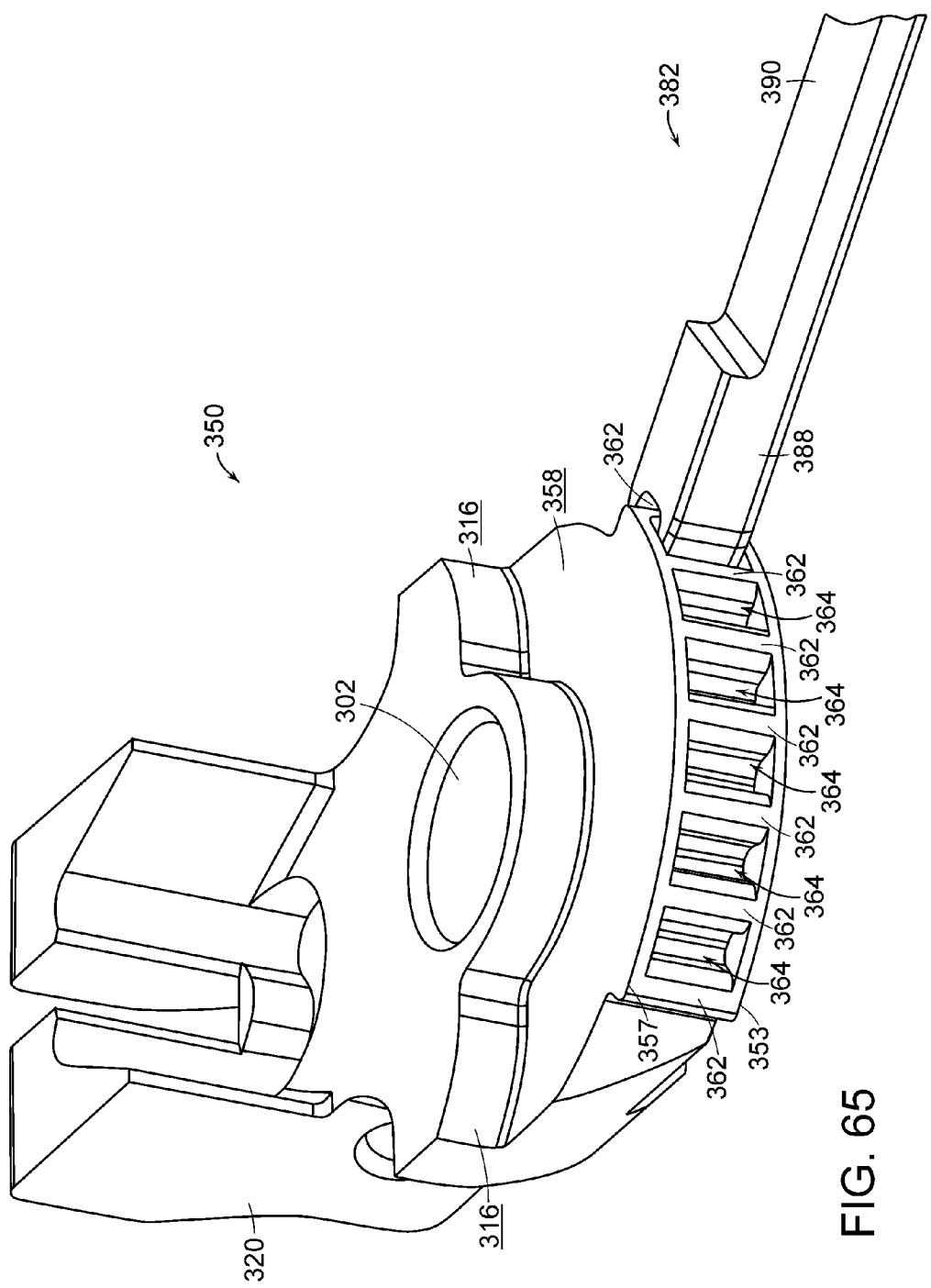
FIG. 65 is a perspective view of the end effector lock member operably engaged with the shaft assembly lock member of FIG. 64.
Figure 66:
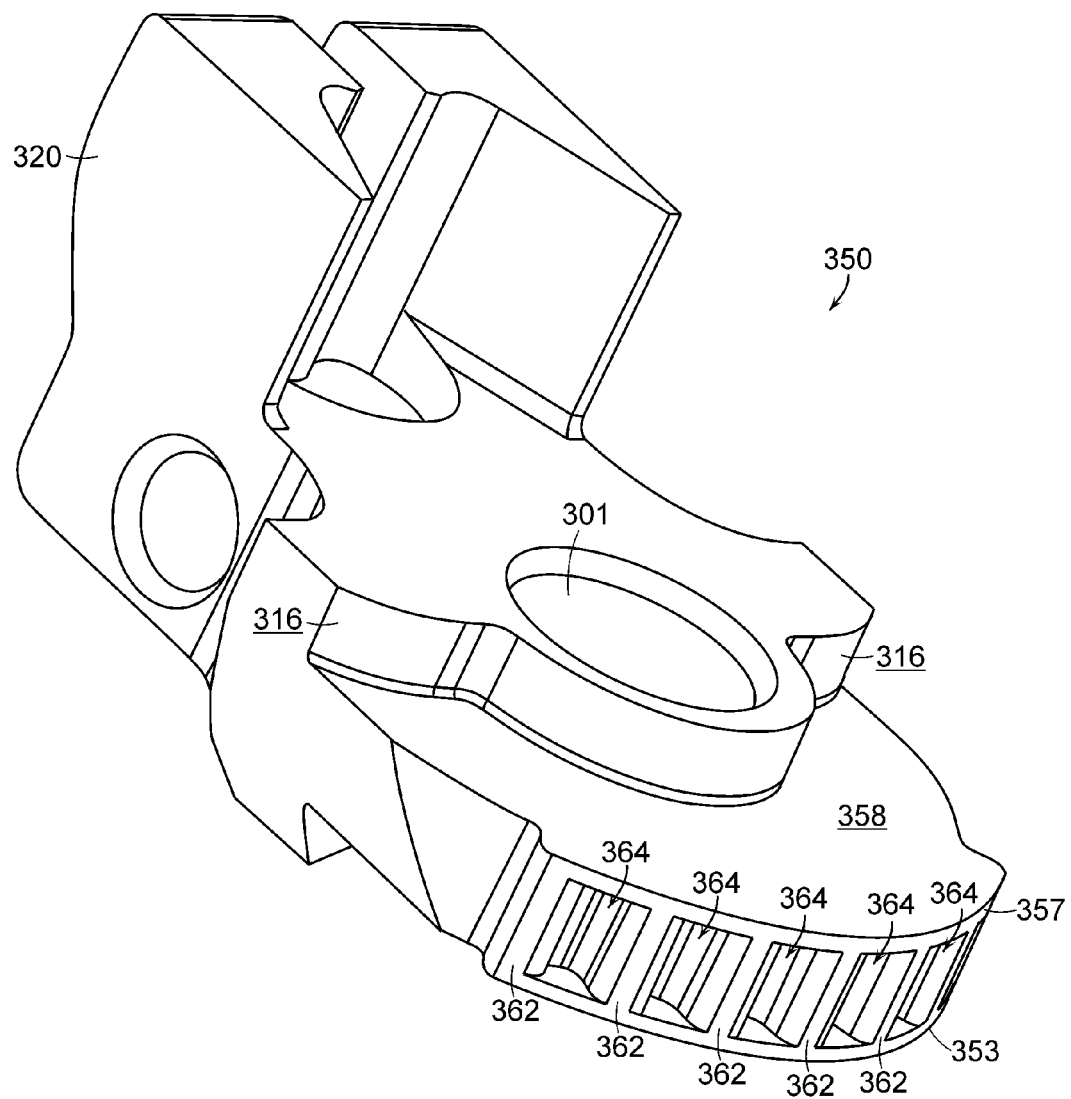
FIG. 66 is a perspective view of the end effector lock member of FIG. 64.
Figure 67:
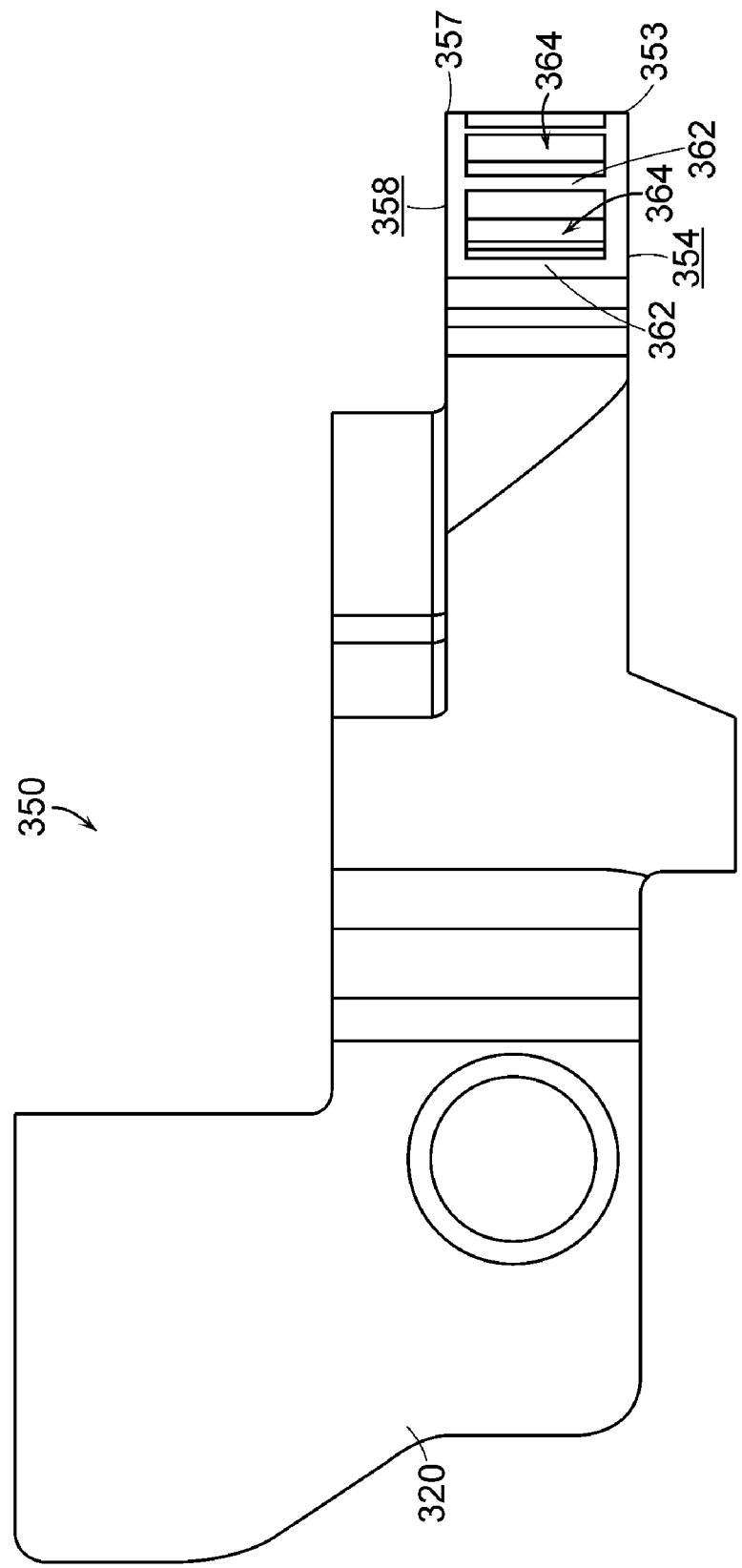
FIG. 67 is an elevational view of the end effector lock member of FIG. 64.

Further to the above, embodiments of the present invention can provide significant advantages over previous surgical instruments. More particularly, referring to FIG. 57, the articulation joints of previous end effectors have included lock members, such as lock member 299, for example, which include teeth 298 that extend outwardly from the perimeter of the lock member. As a result, when the end effector is articulated relative to the shaft assembly of the surgical instrument, teeth 298 can catch on, or impinge upon, the surrounding soft tissue and potentially cause trauma thereto. In various circumstances, tissue can be caught between adjacent teeth 298 such that, when the end effector is articulated, the soft tissue can be pulled into the articulation joint and can be pinched by the relatively moving components of the joint. In embodiments of the present invention in which the teeth of the lock member are angled, or beveled, as outlined above and illustrated in FIG. 58, the soft tissue can more easily flow over the teeth and reduce the possibility that the soft tissue can be pulled into the articulation joint.

As outlined above, referring to FIGS. 59-62, surgical instrument 100 can further include locking member 120 which can be slid relative to end effector 106 and can be operably engaged with end effector 106 to prevent, or at least limit, relative movement between shaft assembly 104 and end effector 106. In at least one embodiment, lock member 120 can be configured to engage at least one of teeth 312 such that end effector 106 is prevented from moving relative to lock member 120. More particularly, lock member 120 can include end portion 338 and shaft portion 340, where end portion 338 can include recess 336 which can be configured to receive a tooth 312 of lock member 300 in a close-fit, or even interference-fit, relationship. In various alternative embodiments, locking portion 338 can be received within at least one of recesses 314 in a close-fit, or interference-fit, relationship similar to the above. In either event, surgical instrument 100 can further include spring 126 which can be configured to bias lock member 120 into engagement with end effector lock member 300. In the event that recess 336 is not aligned with a tooth 312, in at least one embodiment, the biasing force applied to lock member 120 by spring 126 can cause lock member 120 to contact and rotate end effector lock member 300 about axis 116 until one of teeth 312 is aligned with recess 336. In various embodiments, spring 126 can comprise any suitable biasing member including a helical spring, leaf spring, or other biasing material.

In various alternative embodiments, referring to FIGS. 63-67, a surgical instrument can include end effector lock member 350 comprising aperture 301, a first portion including first surface 358, a second portion including second surface 354 (FIG. 67), and connector portion 320. End effector lock member 350 can also comprise teeth 362 and recesses 364 defined between teeth 362 where, in at least one embodiment, teeth 362 and recesses 364 can be positioned intermediate first surface 358 and second surface 354. In various embodiments, referring to FIGS. 65-67, teeth 362 may not extend beyond first perimeter 357 of first surface 358 and/or second perimeter 353 of second surface 354. In at least one such embodiment, teeth 362 may be completely positioned, or contained, between first surface 358 and second surface 354. In at least one alternative embodiment, teeth 362 may partially extend from first perimeter 357 and/or second perimeter 353. In various embodiments, first perimeter 357 and second perimeter 353 can define an outer surface therebetween where recesses 364 can be defined in the outer surface. As a result of the above-described features, end effector lock member 350 can slide relative to soft tissue positioned adjacent to the articulation joint without impinging on the soft tissue. In various embodiments, teeth 362 may be blunted or rounded to further facilitate the relative sliding described above. In at least one embodiment, referring to FIGS. 63-65, a locking mechanism can be configured to engage at least one of teeth 362 and recesses 364 and can include lock member 382 comprising end portion 388 and shaft portion 390. In at least one embodiment, similar to the above, end portion 388 can include recess 394 which can be configured to engage at least one of teeth 362, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
   an elongate shaft;
   a joint;
   an end effector, wherein said end effector is selectively movable relative to said elongate shaft about said joint, said end effector comprising:
      a channel configured to receive a staple cartridge; and
      an anvil movably coupled to said channel;
   a locking mechanism having a locked configuration and an unlocked configuration, wherein, when said locking mechanism is in said locked configuration, said locking mechanism is configured to engage at least one of said elongate shaft and said end effector and at least limit relative movement between said elongate shaft and said end effector, wherein said locking mechanism comprises:
      a lock member moveable relative to said joint, wherein said lock member is configured to engage said end effector when said locking mechanism is in said locked configuration; and
      an actuator, wherein said lock member is operably engaged with said actuator; and
   a closure drive operably engaged with said anvil, wherein said closure drive is movable between a first position and a second position to move said anvil between an open position and a closed position, and wherein, when said closure drive is in said second position, said closure drive is adjacent to said actuator and configured to restrain travel of said actuator and hold said locking mechanism in said locked configuration.

2. The surgical instrument of claim 1, wherein said closure drive is movable into an intermediate position to pivot said anvil into a partially closed position, and wherein, when said closure drive is in said intermediate position, said end effector is movable relative to said elongate shaft.

3. The surgical instrument of claim 1, wherein said closure drive is configured to pivot said anvil into a partially closed position, and wherein, when said anvil is in said partially closed position, said end effector is movable relative to said elongate shaft.

4. The surgical instrument of claim 1, further comprising said staple cartridge.

5. The surgical instrument of claim 1, wherein said closure drive is configured to move said locking mechanism to said locked configuration when said closure drive moves between said first position and said second position.

6. A surgical instrument, comprising:
an elongate shaft;
a joint;
an end effector, wherein said end effector is selectively movable relative to said elongate shaft about said joint, said end effector comprising:
  a channel configured to receive a staple cartridge; and
  an anvil movably coupled to said channel;
a locking mechanism having a locked configuration and an unlocked configuration, wherein, when said locking mechanism is in said locked configuration, said locking mechanism is configured to engage at least one of said elongate shaft and said end effector and at least limit relative movement between said elongate shaft and said end effector; and
a closure drive operably engaged with said anvil, wherein said closure drive is movable between a first position and a second position to move said anvil between an open position and a closed position, and wherein, when said closure drive is in said second position, said closure drive is configured to hold said locking mechanism in said locked configuration;
wherein said locking mechanism comprises:
  a lock member including a first end and a second end, wherein said lock member is slidable relative to said joint, and wherein said first end of said lock member is configured to engage said end effector when said locking mechanism is in said locked configuration; and
  an actuator, wherein said second end of said lock member is operably engaged with said actuator, and wherein said closure drive is configured to abut said actuator when said closure drive is in said second position and prevent said lock member from being slid relative to said joint.

7. The surgical instrument of claim 6, wherein said closure drive includes a trigger and a driver, wherein said trigger is configured to move said driver toward said actuator, wherein said driver is configured to abut said actuator when said closure drive is in said second position, wherein said elongate shaft includes a sheath operably engaged with said anvil and said trigger, and wherein said trigger is configured to move said sheath relative to said end effector and pivot said anvil upon an actuation of said trigger.

8. The surgical instrument of claim 6, further comprising said staple cartridge.

9. The surgical instrument of claim 6, wherein said closure drive is configured to move said locking mechanism to said locked configuration when said closure drive moves between said first position and said second position.

10. A surgical instrument, comprising:
an elongate shaft;
a joint;
an end effector, wherein said end effector is selectively movable relative to said elongate shaft about said joint, said end effector comprising:
  a channel configured to receive a staple cartridge; and
  an anvil movably coupled to said channel;
a locking mechanism having a locked configuration and an unlocked configuration, wherein, when said locking mechanism is in said locked configuration, said locking mechanism is configured to engage at least one of said elongate shaft and said end effector and at least limit relative movement between said elongate shaft and said end effector, wherein said locking mechanism comprises:
  a lock member moveable relative to said joint, wherein said lock member is configured to engage said end effector when said locking mechanism is in said locked configuration; and
  an actuator, wherein said lock member is operably engaged with said actuator; and
a closure drive configured to generate a closing motion, wherein said closure drive includes a driver, wherein said anvil is operably engaged with said driver and is movably responsive to said closing motion, and wherein said driver is adjacent to said actuator and configured to restrain travel of said actuator as a result of said closing motion and prevent said locking mechanism from being configured in said unlocked configuration.

11. The surgical instrument of claim 10, further comprising said staple cartridge.

12. The surgical instrument of claim 10, wherein said driver is configured to move said locking mechanism to said locked configuration as a result of said closing motion.

13. A surgical instrument, comprising:
an elongate shaft;
a joint;
an end effector, wherein said end effector is selectively movable relative to said elongate shaft about said joint, said end effector comprising:
  a channel configured to receive a staple cartridge; and
  an anvil movably coupled to said channel;
a locking mechanism having a locked configuration and an unlocked configuration, wherein, when said locking mechanism is in said locked configuration, said locking mechanism is configured to engage at least one of said elongate shaft and said end effector and at least limit relative movement between said elongate shaft and said end effector; and
a closure drive configured to generate a closing motion, wherein said closure drive includes a driver, wherein said anvil is operably engaged with said driver and is movably responsive to said closing motion, and wherein said driver is configured to engage said locking mechanism as a result of said closing motion and prevent said locking mechanism from being configured in said unlocked configuration;
wherein said locking mechanism comprises:
  a lock member including a first end and a second end, wherein said lock member is slidable relative to said joint, and wherein said first end of said lock member is configured to engage said end effector when said locking mechanism is in said locked configuration; and
  an actuator, wherein said second end of said lock member is operably engaged with said actuator, and wherein said driver is configured to abut said actuator as a result of said closing motion and prevent said lock member from being slid relative to said joint.

14. The surgical instrument of claim 13, wherein said closure drive further includes a trigger, wherein said trigger is configured to move said driver toward said actuator, wherein said elongate shaft assembly includes a sheath operably engaged with said anvil and said trigger, and wherein said trigger is configured to move said sheath relative to said end effector and pivot said anvil upon an actuation of said trigger.

15. The surgical instrument of claim 13, further comprising said staple cartridge.

16. A surgical instrument, comprising:
   a shaft;
   a joint;
   an end effector, wherein said end effector is selectively movable relative to said shaft about said joint, said end effector comprising:
      a first jaw; and
      a second jaw, wherein said first jaw is movable relative to said second jaw;
   a locking mechanism comprising:
      an unlocked configuration in which said end effector is rotatable relative to said shaft about said joint;
      a locked configuration in which said locking mechanism is engaged with said end effector and said end effector is inhibited from rotating relative to said shaft; and
      an actuator configured to place said locking mechanism in at least one of said unlocked configuration and said locked configuration; and
   a closure drive configured to generate a closing motion, wherein said closure drive includes a driver, wherein said first jaw is operably engaged with said driver and is movably responsive to said closing motion, and wherein said driver is adjacent to said actuator and configured to restrain travel of said actuator as a result of said closing motion and retain said locking mechanism in said locked configuration.

17. The surgical instrument of claim 16, wherein said first jaw comprises an anvil, and wherein said second jaw comprises a staple cartridge channel configured to receive a staple cartridge.

18. The surgical instrument of claim 17, further comprising said staple cartridge.

19. The surgical instrument of claim 16, wherein said driver is configured to move said locking mechanism into said locked configuration as a result of said closing motion.

20. The surgical instrument of claim 16, wherein said closure drive further comprises a trigger configured to move said driver between a first position, a second position, and a third position, wherein said first jaw is in an open position when said driver is in said first position, wherein said driver is configured to move said first jaw into a partially closed position when said driver is in said second position, wherein said driver is configured to move said first jaw into a fully closed position when said driver is in said third position, and wherein, when said driver is in said second position, said end effector is movable relative to said shaft.

* * * * *